(12) United States Patent
Hu et al.

(10) Patent No.: US 9,259,358 B2
(45) Date of Patent: *Feb. 16, 2016

(54) REDUCED PRESSURE THERAPY OF THE SACRAL REGION

(71) Applicant: KCI Licensing, Inc., San Antonio, TX (US)

(72) Inventors: Dean Hu, San Leandro, CA (US);
Kenton Fong, Mountain View, CA (US);
Moshe Pinto, Mountain View, CA (US);
Kenneth Wu, San Francisco, CA (US);
Evan Anderson, San Francisco, CA (US); Tony Coxum, San Jose, CA (US);
Brendan Donohoe, Fairfax, CA (US);
Philip Hui, Foster City, CA (US); Craig McGreevy, Walnut Creek, CA (US)

(73) Assignee: KCI Licensing, Inc., San Antonio, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 13/752,206

(22) Filed: Jan. 28, 2013

(65) Prior Publication Data

US 2013/0144231 A1    Jun. 6, 2013

Related U.S. Application Data

(63) Continuation of application No. 12/683,987, filed on Jan. 7, 2010, now Pat. No. 8,361,043.

(60) Provisional application No. 61/143,030, filed on Jan. 7, 2009.

(51) Int. Cl.
*A61M 1/00* (2006.01)
*A61F 13/02* (2006.01)
(Continued)

(52) U.S. Cl.
CPC .......... *A61F 13/0216* (2013.01); *A61F 5/4401* (2013.01); *A61F 13/0203* (2013.01);
(Continued)

(58) Field of Classification Search
CPC ....... A61F 5/4401; A61F 13/00; A61F 13/02; A61M 1/00; A61M 27/00
USPC ................ 604/315, 316, 318, 319
See application file for complete search history.

(56) References Cited

U.S. PATENT DOCUMENTS

| 406,330 A | 7/1889 | Austin |
| 418,469 A | 12/1889 | McKinley |

(Continued)

FOREIGN PATENT DOCUMENTS

| CN | 1438904 A | 8/2003 |
| CN | 2851641 Y | 12/2006 |

(Continued)

OTHER PUBLICATIONS

Non Final Office Action received for U.S. Appl. No. 12/047,739, mailed on Feb. 13, 2012, 12 pages.

(Continued)

*Primary Examiner* — Tatyana Zalukaeva
*Assistant Examiner* — Ilya Treyger

(57) ABSTRACT

Reduced pressure wound therapy is performed on a sacral region of a patient using an adhesive dressing comprising a flexible planar layer and a non-planar fold-sealing region configured to seal to the intergluteal cleft of a patient. The fold-sealing region is located on an outer edge of the adhesive dressing and comprises a tapered configuration.

20 Claims, 34 Drawing Sheets

(51) Int. Cl.
*A61F 5/44* (2006.01)
*A61M 27/00* (2006.01)
*A61F 13/00* (2006.01)
*A61F 13/15* (2006.01)

(52) U.S. Cl.
CPC ............... A61F2013/0054 (2013.01); A61F 2013/00272 (2013.01); A61F 2013/00404 (2013.01); A61F 2013/00574 (2013.01); A61F 2013/15024 (2013.01); A61F 2013/15154 (2013.01)

(56) References Cited

U.S. PATENT DOCUMENTS

| | | | |
|---|---|---|---|
| 617,936 A | 1/1899 | Nicolas | |
| 2,198,666 A | 4/1940 | Gruskin | |
| 2,306,107 A | 12/1942 | Henderson | |
| 2,472,116 A | 6/1949 | Maynes | |
| 2,523,850 A | 9/1950 | Steinberg | |
| 2,660,342 A | 11/1953 | Ruf | |
| 2,863,452 A | 12/1958 | Ogle, Sr. | |
| 3,073,309 A | 1/1963 | Mosier | |
| 3,334,628 A | 8/1967 | Saemann et al. | |
| 3,401,522 A | 9/1968 | Hann et al. | |
| 3,583,399 A | 6/1971 | Ritsky | |
| 3,628,325 A | 12/1971 | Morita | |
| 3,680,560 A | 8/1972 | Pannier, Jr. et al. | |
| 3,750,393 A | 8/1973 | Minto et al. | |
| 3,779,243 A | 12/1973 | Tussey et al. | |
| 3,809,086 A | 5/1974 | Schachet et al. | |
| 3,809,087 A | 5/1974 | Lewis, Jr. | |
| 3,833,030 A | 9/1974 | Waldbauer, Jr. et al. | |
| 3,841,331 A | 10/1974 | Wilder et al. | |
| 3,864,766 A | 2/1975 | Prete, Jr. | |
| 3,958,570 A | 5/1976 | Vogelman et al. | |
| 3,982,546 A | 9/1976 | Friend | |
| 4,041,934 A | 8/1977 | Genese | |
| 4,067,330 A | 1/1978 | Roache | |
| 4,080,970 A | 3/1978 | Miller | |
| 4,124,116 A | 11/1978 | McCabe, Jr. | |
| 4,278,089 A | 7/1981 | Huck et al. | |
| 4,287,819 A | 9/1981 | Emerit | |
| 4,333,456 A | 6/1982 | Webb | |
| 4,333,458 A | 6/1982 | Margulies et al. | |
| 4,382,441 A | 5/1983 | Svedman | |
| 4,404,924 A | 9/1983 | Goldberg et al. | |
| 4,484,919 A * | 11/1984 | Sohn et al. | 604/358 |
| 4,525,167 A | 6/1985 | Goldberg et al. | |
| 4,549,554 A | 10/1985 | Markham | |
| 4,569,674 A | 2/1986 | Phillips et al. | |
| 4,578,060 A | 3/1986 | Huck et al. | |
| 4,648,870 A | 3/1987 | Goldberg et al. | |
| 4,664,128 A | 5/1987 | Lee | |
| 4,743,232 A | 5/1988 | Kruger | |
| 4,747,960 A | 5/1988 | Freeman et al. | |
| 4,758,232 A | 7/1988 | Chak | |
| 4,867,748 A | 9/1989 | Samuelsen | |
| 4,882,377 A | 11/1989 | Sweet et al. | |
| 4,889,250 A | 12/1989 | Beyer | |
| 4,969,880 A | 11/1990 | Zamierowski | |
| 5,018,516 A | 5/1991 | Gilman | |
| 5,071,409 A | 12/1991 | Rosenberg | |
| 5,073,172 A | 12/1991 | Fell | |
| 5,100,396 A | 3/1992 | Zamierowski | |
| 5,107,859 A | 4/1992 | Alcorn et al. | |
| 5,116,310 A | 5/1992 | Seder et al. | |
| 5,116,610 A | 5/1992 | Broaddus | |
| 5,133,821 A | 7/1992 | Jensen | |
| 5,154,697 A * | 10/1992 | Loori | 604/23 |
| 5,157,808 A | 10/1992 | Sterner, Jr. | |
| 5,261,893 A | 11/1993 | Zamierowski | |
| 5,263,922 A | 11/1993 | Sova et al. | |
| 5,266,476 A | 11/1993 | Sussman et al. | |
| 5,284,621 A | 2/1994 | Kaufman | |
| 5,356,372 A | 10/1994 | Donovan et al. | |
| 5,358,494 A | 10/1994 | Svedman | |
| 5,380,295 A | 1/1995 | Vacca | |
| 5,395,345 A | 3/1995 | Gross | |
| 5,527,293 A | 6/1996 | Zamierowski | |
| 5,531,999 A | 7/1996 | Cartmell et al. | |
| 5,584,801 A | 12/1996 | Kuroyanagi et al. | |
| 5,636,643 A | 6/1997 | Argenta et al. | |
| 5,645,081 A | 7/1997 | Argenta et al. | |
| H1687 H * | 10/1997 | Roe et al. | 604/385.21 |
| 5,701,917 A | 12/1997 | Khouri | |
| 5,704,905 A | 1/1998 | Jensen et al. | |
| 5,711,969 A | 1/1998 | Patel et al. | |
| 5,845,641 A | 12/1998 | Pinney et al. | |
| 5,961,497 A | 10/1999 | Larkin | |
| 5,970,979 A | 10/1999 | Christofel et al. | |
| 6,071,267 A | 6/2000 | Zamierowski | |
| 6,142,982 A | 11/2000 | Hunt et al. | |
| 6,174,306 B1 | 1/2001 | Fleischmann | |
| 6,211,426 B1 * | 4/2001 | Abrams | 602/46 |
| 6,235,964 B1 | 5/2001 | Kadash et al. | |
| 6,258,995 B1 | 7/2001 | Gilding et al. | |
| 6,261,276 B1 | 7/2001 | Reitsma | |
| 6,266,859 B1 | 7/2001 | Hernandez | |
| 6,345,623 B1 | 2/2002 | Heaton et al. | |
| 6,368,305 B1 | 4/2002 | Dutton | |
| 6,387,082 B1 | 5/2002 | Freeman | |
| 6,458,109 B1 | 10/2002 | Henley et al. | |
| 6,461,467 B2 | 10/2002 | Blatchford et al. | |
| 6,467,432 B1 | 10/2002 | Lewis et al. | |
| 6,553,998 B2 | 4/2003 | Heaton et al. | |
| 6,685,681 B2 | 2/2004 | Lockwood et al. | |
| 6,695,823 B1 | 2/2004 | Lina et al. | |
| 6,695,824 B2 | 2/2004 | Howard et al. | |
| 6,752,794 B2 | 6/2004 | Lockwood et al. | |
| 6,755,807 B2 | 6/2004 | Risk, Jr. et al. | |
| 6,800,074 B2 | 10/2004 | Henley et al. | |
| 6,814,079 B2 | 11/2004 | Heaton et al. | |
| 6,825,246 B1 | 11/2004 | Fattman | |
| 6,855,135 B2 | 2/2005 | Lockwood et al. | |
| 6,913,573 B1 * | 7/2005 | Viscomi et al. | 600/29 |
| 6,979,324 B2 | 12/2005 | Byobrdi et al. | |
| 6,986,234 B2 | 1/2006 | Liedtke | |
| 7,070,584 B2 | 7/2006 | Johnson et al. | |
| 7,117,869 B2 | 10/2006 | Heaton et al. | |
| 7,198,046 B1 | 4/2007 | Argenta et al. | |
| 7,216,651 B2 | 5/2007 | Argenta et al. | |
| 7,273,054 B2 | 9/2007 | Heaton et al. | |
| 7,316,672 B1 | 1/2008 | Hunt et al. | |
| 7,341,574 B2 | 3/2008 | Schreijag | |
| 7,448,653 B2 | 11/2008 | Jensen et al. | |
| 7,461,158 B2 | 12/2008 | Rider et al. | |
| 7,485,112 B2 | 2/2009 | Karpowicz et al. | |
| 7,520,872 B2 | 4/2009 | Biggie et al. | |
| 7,569,745 B2 | 8/2009 | Sticklen et al. | |
| 7,597,690 B2 | 10/2009 | Tanio et al. | |
| D607,112 S | 12/2009 | Rogers et al. | |
| 7,763,000 B2 | 7/2010 | Risk, Jr. et al. | |
| 7,771,377 B2 | 8/2010 | Stapf et al. | |
| 7,779,625 B2 | 8/2010 | Joshi et al. | |
| 7,794,438 B2 | 9/2010 | Henley et al. | |
| 7,837,673 B2 | 11/2010 | Vogel | |
| 7,863,495 B2 | 1/2011 | Aali | |
| 7,875,761 B2 | 1/2011 | Budig et al. | |
| 7,880,050 B2 | 2/2011 | Robinson et al. | |
| 7,926,856 B2 | 4/2011 | Smutney et al. | |
| 7,928,279 B2 * | 4/2011 | Rosenberg | 602/48 |
| 7,928,281 B2 | 4/2011 | Augustine | |
| 7,942,866 B2 | 5/2011 | Radl et al. | |
| 7,959,624 B2 | 6/2011 | Riesinger | |
| 8,007,491 B2 | 8/2011 | Pinto et al. | |
| 8,128,607 B2 | 3/2012 | Hu et al. | |
| 8,148,595 B2 | 4/2012 | Robinson et al. | |
| 8,162,908 B2 | 4/2012 | Hu et al. | |
| 8,177,764 B2 | 5/2012 | Hu et al. | |
| 8,308,705 B2 | 11/2012 | Lin et al. | |
| 8,337,474 B2 | 12/2012 | Hu et al. | |
| 8,361,043 B2 * | 1/2013 | Hu et al. | 604/319 |
| 8,409,156 B2 | 4/2013 | Kazala, Jr. et al. | |

(56) References Cited

U.S. PATENT DOCUMENTS

| | | |
|---|---|---|
| 2001/0031943 A1 | 10/2001 | Urie |
| 2001/0043943 A1 | 11/2001 | Coffey |
| 2002/0026133 A1 | 2/2002 | Augustine et al. |
| 2002/0150720 A1 | 10/2002 | Howard et al. |
| 2002/0173808 A1 | 11/2002 | Houser et al. |
| 2002/0183702 A1 | 12/2002 | Henley et al. |
| 2002/0198503 A1 | 12/2002 | Risk, Jr. et al. |
| 2003/0050594 A1 | 3/2003 | Zamierowski |
| 2003/0088201 A1 | 5/2003 | Darcey |
| 2003/0120194 A1 | 6/2003 | Stapf |
| 2003/0190339 A1 | 10/2003 | Skover et al. |
| 2004/0249353 A1 | 12/2004 | Risks, Jr. et al. |
| 2004/0261642 A1 | 12/2004 | Hess |
| 2005/0101940 A1 | 5/2005 | Radl et al. |
| 2005/0192544 A1 | 9/2005 | Wolbring et al. |
| 2005/0222527 A1 | 10/2005 | Miller et al. |
| 2005/0261642 A1 | 11/2005 | Weston |
| 2005/0267433 A1 | 12/2005 | Tanio et al. |
| 2006/0253090 A1 | 11/2006 | Bradley et al. |
| 2006/0282028 A1 | 12/2006 | Howard et al. |
| 2007/0027414 A1 | 2/2007 | Hoffman et al. |
| 2007/0066946 A1 | 3/2007 | Haggstrom et al. |
| 2007/0066948 A1 | 3/2007 | Erdman |
| 2007/0219512 A1 | 9/2007 | Heaton et al. |
| 2007/0219532 A1 | 9/2007 | Karpowicz et al. |
| 2007/0233022 A1 | 10/2007 | Henley et al. |
| 2008/0004559 A1 | 1/2008 | Riesinger |
| 2008/0009812 A1 | 1/2008 | Riesinger |
| 2008/0033330 A1 | 2/2008 | Moore |
| 2008/0063615 A1 | 3/2008 | MacDonald et al. |
| 2008/0082059 A1 | 4/2008 | Fink et al. |
| 2008/0086214 A1 | 4/2008 | Hardin et al. |
| 2008/0108977 A1 | 5/2008 | Heaton et al. |
| 2008/0200906 A1 | 8/2008 | Sanders et al. |
| 2008/0234641 A1 | 9/2008 | Locke et al. |
| 2008/0294147 A1 * | 11/2008 | Radl et al. ............ 604/543 |
| 2008/0306448 A1 | 12/2008 | Lee |
| 2008/0306456 A1 | 12/2008 | Riesinger |
| 2009/0012482 A1 | 1/2009 | Pinto et al. |
| 2009/0076467 A1 | 3/2009 | Pinto et al. |
| 2009/0187130 A1 | 7/2009 | Asmus et al. |
| 2009/0221977 A1 | 9/2009 | Blott et al. |
| 2009/0240218 A1 | 9/2009 | Braga et al. |
| 2009/0254066 A1 | 10/2009 | Heaton et al. |
| 2010/0030166 A1 | 2/2010 | Tout et al. |
| 2010/0036333 A1 | 2/2010 | Schenk, III et al. |
| 2010/0042021 A1 | 2/2010 | Hu et al. |
| 2010/0042059 A1 | 2/2010 | Pratt et al. |
| 2010/0100063 A1 | 4/2010 | Joshi et al. |
| 2010/0137775 A1 | 6/2010 | Hu et al. |
| 2010/0145289 A1 | 6/2010 | Lina et al. |
| 2010/0160879 A1 | 6/2010 | Weston |
| 2010/0160901 A1 | 6/2010 | Hu et al. |
| 2010/0168719 A1 | 7/2010 | Chen |
| 2010/0174250 A1 | 7/2010 | Hu et al. |
| 2010/0179493 A1 | 7/2010 | Heagle et al. |
| 2010/0198174 A1 | 8/2010 | Hu et al. |
| 2010/0228205 A1 | 9/2010 | Hu et al. |
| 2010/0262090 A1 | 10/2010 | Riesinger |
| 2010/0262094 A1 | 10/2010 | Walton et al. |
| 2010/0324510 A1 | 12/2010 | Andresen et al. |
| 2011/0106030 A1 | 5/2011 | Scholz |
| 2011/0130691 A1 | 6/2011 | Hu et al. |
| 2011/0137270 A1 | 6/2011 | Hu et al. |
| 2011/0313377 A1 | 12/2011 | Pinto et al. |
| 2012/0016325 A1 | 1/2012 | Pinto et al. |
| 2012/0078207 A1 | 3/2012 | Hu et al. |
| 2013/0006204 A1 | 1/2013 | Hu et al. |
| 2013/0090615 A1 | 4/2013 | Jaeb et al. |
| 2013/0144231 A1 | 6/2013 | Hu et al. |

FOREIGN PATENT DOCUMENTS

| | | | |
|---|---|---|---|
| DE | 19517699 A1 | 11/1996 | |
| DE | 202004017052 U1 | 7/2005 | |
| DE | 202005019670 U1 | 6/2006 | |
| EP | 0360329 A1 | 3/1990 | |
| EP | 2098257 A1 | 9/2009 | |
| FR | 1163907 A | 10/1958 | |
| GB | 2195255 A | 4/1988 | |
| GB | 2306107 A | 4/1997 | |
| GB | 2431351 A | 4/2007 | |
| JP | 55-68370 A | 5/1980 | |
| JP | 59-177055 A | 10/1984 | |
| JP | 4-506760 A | 11/1992 | |
| JP | 11-504833 A | 5/1999 | |
| JP | 2003-284770 A | 10/2003 | |
| JP | 2003-532504 A | 11/2003 | |
| JP | 2007-534403 A | 11/2007 | |
| JP | 2010-506615 A | 3/2010 | |
| SE | WO 2009/002260 A1 * | 12/2008 | |
| WO | 80/02182 A1 | 10/1980 | |
| WO | 91/00718 A1 | 1/1991 | |
| WO | 96/35401 A1 | 11/1996 | |
| WO | 01/85248 A1 | 11/2001 | |
| WO | 03/070135 A2 | 8/2003 | |
| WO | 2004/037334 A1 | 5/2004 | |
| WO | 2005/051461 A1 | 6/2005 | |
| WO | 2005/105179 A1 | 11/2005 | |
| WO | 2006/005939 A1 | 1/2006 | |
| WO | 2006/048240 A1 | 5/2006 | |
| WO | 2007/030601 A2 | 3/2007 | |
| WO | 2007/030601 A3 | 5/2007 | |
| WO | 2007/067685 A2 | 6/2007 | |
| WO | 2007/123451 A1 | 11/2007 | |
| WO | 2008/048527 A2 | 4/2008 | |
| WO | 2008/100446 A2 | 8/2008 | |
| WO | 2008/112304 A1 | 9/2008 | |
| WO | 2008/100446 A3 | 10/2008 | |
| WO | 2007/067685 A3 | 11/2008 | |
| WO | 2009/002260 A1 | 12/2008 | |
| WO | WO 2009/002260 A1 * | 12/2008 | ............ A61F 13/02 |
| WO | 2009/089016 A1 | 7/2009 | |
| WO | 2009/103031 A1 | 8/2009 | |
| WO | 2010/068502 A1 | 6/2010 | |
| WO | 2010/080907 A1 | 7/2010 | |
| WO | 2010/102146 A1 | 9/2010 | |

OTHER PUBLICATIONS

Notice of Allowance received for U.S. Appl. No. 12/234,530, mailed on Jun. 24, 2011, 12 pages.

Non Final Office Action received for U.S. Appl. No. 12/626,426, mailed on Oct. 12, 2011, 15 pages.

Non Final Office Action received for U.S. Appl. No. 12/646,856, mailed on Nov. 2, 2011, 16 pages.

Notice of Allowance received for U.S. Appl. No. 12/760,406, mailed on Dec. 22, 2011, 9 pages.

Notice of Allowance received for U.S. Appl. No. 12/760,409, mailed on Jul. 17, 2012, 16 pages.

Non Final Office Action received for U.S. Appl. No. 13/030,042, mailed on Oct. 31, 2011, 18 pages.

Non-Final Office Action received for U.S. Appl. No. 13/245,735, mailed on Nov. 18, 2011, 14 pages.

Non Final Office Action received for U.S. Appl. No. 13/245,746, mailed on Dec. 23, 2011, 11 pages.

Office Action received for Japanese Patent Application No. 2010-546944, mailed on Jun. 19, 2012, 4 pages.

Notice of Allowance received for U.S. Appl. No. 12/372,661, mailed on Apr. 9, 2012, 5 pages.

Pre-Interview First Office Action received for U.S. Appl. No. 12/372,661, mailed on Dec. 15, 2011, 4 pages.

International Search Report and Written Opinion received for PCT Patent Application No. PCT/US2008/003412, mailed on Jul. 28, 2008, 6 pages.

International Preliminary Report on Patentability received for PCT Patent Application No. PCT/US2008/003412, issued on Sep. 15, 2009, 6 pages.

(56) References Cited

OTHER PUBLICATIONS

International Search Report and Written Opinion received for PCT Patent Application No. PCT/US2009/034158, mailed on May 29, 2009, 13 pages.
International Search Report and Written Opinion received for PCT Patent Application No. PCT/US2009/065959, mailed on Jan. 21, 2010, 11 pages.
International Preliminary Report on Patentability received for PCT Patent Application No. PCT/US2009/065959, mailed on Jun. 9, 2011, 9 pages.
International Search Report and Written Opinion received for PCT Patent Application No. PCT/US2010/026269, mailed on May 4, 2010, 9 pages.
Final Office Action received for U.S. Appl. No. 12/047,739, mailed on Apr. 21, 2010, 16 pages.
Anonymous, "Drain and Suture Line Care for Wounds". The Cleveland Clinic Foundation, located at <http://www.clevelandclinic.org/health/healthinfo/docs/22000/2205.asp?i . . . >, last visited Oct. 15, 2007, 4 pages.
Bagautdinov, N. A., "Variant of External Vacuum Aspiration in the Treatment of Purulent Diseases of Soft Tissues", Current Problems in Modern Clinical Surgery, Cheboksary: Chuvashia State University, 1986, 14 pages.
Chariker et al., "Effective Management of Incisional and Cutaneous Fistulae with Closed Suction Wound Drainage", Contemporary Surgery, vol. 34, Jun. 1989, pp. 59-63.
Davydov et al., "Concepts for Clinical Biological Management of the Wound Process in the Treatment of Purulent Wounds Using Vacuum Therapy", The Kremlin Papers: Perspectives in Wound Care, Feb. 1991, pp. 15-17.
Davydov et al., "The Bacteriological and Cytological Assessment of Vacuum Therapy of Purulent Wounds", The Kremlin Papers: Perspectives in Wound Care, Oct. 1988, pp. 11-14.
Davydov et al., "Vacuum Therapy in the Treatment of Purulent Lactation Mastitis", The Kremlin Papers: Perspectives in Wound Care, Sep. 1986, pp. 5-7.
Herrmann et al., "The Conservative Treatment of Arteriosclerotic Peripheral Vascular Diseases: Passive Vascular Exercises (Pavaex Therapy)", Ann. Surgery, 1934, pp. 750-760.
Kostiuchenok et al., "The Vacuum Effect in the Surgical Treatment of Purulent Wounds", The Kremlin Papers: Perspectives in Wound Care, Sep. 1986, pp. 3-4.
Meyer et al., "Weight-Loaded Syringes as a Simple and Cheap Alternative to Pumps for Vacuum-Enhanced Wound Healing", Plastic and Reconstructive Surgery, vol. 115, No. 7: located at <http://gateway.tx.ovid.com.laneproxy.stanford.edu/gw2/ovidweb.cgi>, last visited on Oct. 15, 2007, Jun. 2005, pp. 2174-2176.
Svedman, P. "A Dressing System Providing Fluid Supply and Suction Drainage Used for Continuous or Intermittent Irrigation", Annals of Plastic Surgery, vol. 17, No. 2, Aug. 1986, pp. 125-133.
Svedman, P., "Irrigation Treatment of Leg Ulcers", The Lancet, Sep. 3, 1983, pp. 532-534.
Ubbink et al., "Topical Negative Pressure for Treating Chronic Wounds", The Cochrane Collaboration, vol. 3, 2009, pp. 1-32.
Urschel et al., "The Effect of Mechanical Stress on Soft and Hard Tissue Repair; a Review", British Journal of Plastic Surgery, vol. 41, 1988, pp. 182-186.
Usupov et al., "Active Wound Drainage", The Kremlin Papers: Perspectives in Wound Care, Apr. 1987, pp. 8-10.
Final Office Action received for U.S. Appl. No. 12/234,530, mailed on Apr. 22, 2010, 16 pages.
Non Final Office Action received for U.S. Appl. No. 12/047,739, mailed on Nov. 27, 2009, 21 pages.
Non Final Office Action received for U.S. Appl. No. 12/234,530, mailed on Oct. 29, 2009, 17 pages.
International Preliminary Report on Patentability received for PCT Patent Application No. PCT/US2009/034158, issued on Aug. 17, 2010, 8 pages.

International Preliminary Report on Patentability received for PCT Patent Application No. PCT/US2010/020368, issued on Jul. 12, 2011, 6 pages.
"Atmosphere—Definition from the Merriam-Webster Online Dictionary", available at <http://www.merriam-webster.com/dictionary/atmosphere>, accessed on Nov. 20, 2009, 2 pages.
Extended European Search Report received for European Patent Application No. 098323710, mailed on Feb. 26, 2013, 8 pages.
Office Action received for European Patent Application No. 09709714.1, mailed on Jan. 26, 2011, 4 pages.
Office Action received for European Patent Application No. 09709714.1, mailed on Mar. 20, 2013, 4 pages.
Non Final Office Action received for U.S. Appl. No. 12/234,530, mailed on Nov. 16, 2010, 14 pages.
Final Office Action received for U.S. Appl. No. 12/626,426, mailed on Aug. 31, 2012, 22 pages.
Final Office Action received for U.S. Appl. No. 12/047,739, mailed on Nov. 7, 2012, 12 pages.
Non Final Office Action received for U.S. Appl. No. 12/646,856, mailed on Feb. 26, 2013, 18 pages.
Non Final Office Action received for U.S. Appl. No. 12/626,426, mailed on Mar. 1, 2013, 9 pages.
Final Office Action received for U.S. Appl. No. 12/717,838, mailed on Apr. 11, 2013, 15 pages.
"Mask—Medical Definition and More from Merriam-Webster", available at <http://www.merriam-webster.com/medical/mask>, accessed on Aug. 25, 2012, 2 pages.
PolyMem QuadraFoam, Case Study, "Huge Sacral Pressure Ulcer Closed in Four Months Using PolyMem Silver and PolyMem Wic Silver Dressings", Presented at 17th Conference of the European Wound Management Association, Poster #135, May 2-4, 2007, Glasgow, Scotland, 2 pages.
Final Office Action received for U.S. Appl. No. 12/646,856 mailed on Jul. 26, 2012, 18 pages.
Final Office Action received for U.S. Appl. No. 12/646,426, mailed on Dec. 12, 2012, 8 pages.
Office Action received for Australian Patent Application No. 2009214439, mailed on May 9, 2013, 3 pages.
Office Action received for Chinese Patent Application No. 200980112984.X, mailed on Dec. 4, 2012, 13 pages (5 pages of English Translation and 8 pages of Official Copy).
Office Action received for Chinese Patent Application No. 200980112984.X, mailed on Aug. 16, 2013, 11 pages (4 pages of English Translation and 7 pages of Office Action).
Non Final Office Action received for U.S. Appl. No. 13/030,042, mailed on May 8, 2013, 19 pages.
Notice of Allowance received for U.S. Appl. No. 13/245,746, mailed on May 29, 2013, 10 pages.
Non Final Office Action received for U.S. Appl. No. 12/047,739, mailed on Jun. 21, 2013, 12 pages.
Non Final Office Action received for U.S. Appl. No. 13/221,734, mailed on Jul. 19, 2013, 9 pages.
Advisory Action received for U.S. Appl. No. 12/717,838, mailed on Jul. 5, 2013, 2 pages.
US 7,186,244, 03/2007, Hunt et al. (withdrawn).
3M Tegaderm Hydrocolloid Dressing, Sacral-6-3/4"×6-3/8", 1 page.
"Adhesive Sacral Dressing, Smith & Nephew", 3 pages.
"EuroMed, Hydrocolloid Health Technologies, Product Catalog", 11 pages.
"Mil—Spec Fasteners", McGraw-Hill Dictionary of Scientific and Technical Terms, 6th edition, 2003, 2 pages.
Verburn, "PolyMem Quadrafoam", New Product Announcement, 4 pages.
Extended European Search Report (includes Supplementary European Search Report and Search Opinion) received for European Patent Application No. 08726845.4, mailed on Jun. 20, 2014, 7 pages.
Intention to Grant received for European Patent Application No. 09709714.1, mailed on Apr. 29, 2014, 8 pages.
Intention to Grant received for European Patent Application No. 09832371.0, mailed on Jun. 2, 2014, 5 pages.
Office Action received for European Patent Application No. 09832371.0, mailed on Oct. 30, 2013, 5 pages.

(56) References Cited

OTHER PUBLICATIONS

Final Office Action received for U.S. Appl. No. 12/047,739, mailed on Feb. 13, 2014, 16 pages.
Final Office Action received for U.S. Appl. No. 12/626,426, mailed on Jan. 3, 2014, 11 pages.
Advisory Action received for U.S. Appl. No. 12/646,856, mailed on Jan. 29, 2014, 3 pages.
Final Office Action received for U.S. Appl. No. 12/646,856, mailed on Nov. 4, 2013, 19 pages.
Notice of Allowance received for U.S. Appl. No. 12/717,838, mailed on Jan. 8, 2014, 10 pages.
Non-Final Office Action received for U.S. Appl. No. 13/020,685, mailed on Feb. 14, 2014, 9 pages.
Final Office Action received for U.S. Appl. No. 13/030,042, mailed on Mar. 14, 2014, 26 pages.
Non-Final Office Action received for U.S. Appl. No. 13/077,857, mailed on Jul. 17, 2014, 12 pages.
Final Office Action received for U.S. Appl. No. 13/221,734 mailed on Feb. 26, 2014, 13 pages.
Non-Final Office Action received for U.S. Appl. No. 13/221,734, mailed on Jun. 19, 2014, 11 pages.
Notice of Allowance received for U.S. Appl. No. 13/615,173, mailed on Sep. 24, 2014, 7 pages.
Office Action received for Australian Patent Application No. 2009214439, issued on Jul. 1, 2014, 4 pages.
Notification to Grant received for Chinese Patent Application No. 200980112984.X, issued on Mar. 19, 2014, 4 pages (2 pages of English Translation and 2 pages of Official Copy).
Office Action received for Japanese Patent Application No. 2010-546944, mailed on Apr. 1, 2013, 5 pages (3 pages of English Translation and 2 pages of Official Copy).
Notice of Allowance received for Japanese Patent Application No. 2010-546944, mailed on Mar. 3, 2014, 3 pages of Official Copy Only, (See Communication under 37 CFR § 1.98(a) (3)).
Office Action received for Japanese Patent Application No. 2011-537745, mailed on Apr. 15, 2014, 4 pages (2 pages of English Translation and 2 pages of Official Copy).
Office Action received for Japanese Patent Application No. 2011-537745, mailed on Dec. 6, 2013, 7 pages (4 pages of English Translation and 3 pages of Official Copy).
Office Action received for Japanese Patent Application No. 2012-229673, mailed on Sep. 17, 2013, 5 pages (3 pages of English Translation and 2 pages of Official Copy).
Office Action received for U.S. Patent Application No. 2012-229673, mailed on May 30, 2014, 4 pages (2 pages of English Translation and 2 pages of Official Copy).
Office Action received for Japanese Patent Application No. 2012-229674, mailed on Nov. 20, 2013, 2 pages of Official Copy Only, (See Communication under 37 CFR § 1.98(a) (3)).
Computer Language Company Inc., "Threaded Connector", Computer Desktop Encyclopedia, 1981, 2 pages.
Extended European Search Report (includes Supplementary European Search Report and Search Opinion) received for European Patent Application No. 14187150.9, mailed on Dec. 10, 2014, 6 pages.
Notice of Acceptance Received for Australian Patent Application No. 2009214439, mailed on Sep. 10, 2014, 2 pages.
Notice of Allowance received for Japanese Patent Application No. 2011-537745, mailed on Dec. 10, 2014, 3 pages (Official Copy only). (See Communication under 37 CFR § 1.98(a) (3)).
Notice of Allowance received for Japanese Patent Application No. 2012-229673, mailed on Dec. 16, 2014, 3 pages (Official Copy only). (See Communication under 37 CFR § 1.98(a) (3)).
Office Action Received for Japanese Patent Application No. 2012-229674, mailed on Nov. 27, 2014, 2 pages (Official Copy only). (See Communication under 37 CFR § 1.98(a) (3)).
Non-Final Office Action received for U.S. Appl. No. 12/626,426, mailed on Dec. 23, 2014, 14 pages.
Notice of Allowance received for U.S. Appl. No. 13/020,685, mailed on Oct. 15, 2014, 9 pages.
Non Final Office Action received for U.S. Appl. No. 12/047,739, mailed on May 15, 2015, 15 pages.
Non-Final Office Action received for U.S. Appl. No. 13/030,042, mailed on Apr. 10, 2015, 27 pages.
Non Final Office Action received for U.S. Appl. No. 13/077,857, mailed on Apr. 24, 2015, 9 pages.
Final Office Action received for U.S. Appl. No. 13/221,734, mailed on Apr. 9, 2015, 9 pages.
Notice of Allowance received for Canadian Patent Application No. 2,715,645, mailed on Mar. 12, 2015, 1 page.
Office Action received for Australian Patent Application No. 2009324913, issued on Feb. 24, 2015, 4 pages.
Wicks, Gill, "A Guide to the Treatment of Pressure Ulcers from Grade 1-Grade 4", Wound Essentials, vol. 2, 2007, 106,108,110,112-113 pages.
International Search Report and Written Opinion received for PCT Patent Application No. PCT/US2010/020368, mailed on Feb. 26, 2010, 7 pages.
International Preliminary Report on Patentability received for PCT Patent Application No. PCT/US2010/026269, mailed on Sep. 15, 2011, 9 pages.
Final Office Action received for U.S. Appl. No. 13/030,042, mailed on Aug. 31, 2012, 21 pages.
Non Final Office Action received for U.S. Appl. No. 12/683,987, mailed on Nov. 5, 2012, 21 pages.
Non Final Office Action received for U.S. Appl. No. 12/717,838, mailed on Jun. 28, 2012, 14 pages.
Notice of Allowance received for U.S. Appl. No. 12/683,987, mailed on Dec. 10, 2012, 7 pages.
Notice of Allowance received for U.S. Appl. No. 13/245,735, mailed on Mar. 7, 2012, 7 pages.
Fletcher, Jacqui, "World Wide Wounds, Dressings: Cutting and Application Guide", May 2007, available at: <http://www.worldwidewounds.com/2007/may/Fletcher/Fletcher-Dressings-Cutting-Guide.html>, 15 pages.
Girolami, Susan, "Bio-Dome™ Technology: The Newest Approach to Negative Pressure Wound Therapy", 1 page.
Gokoo et al., "Evaluation of a Sacral Shaped Transparent Dressing Over Contoured and High Stress Areas", 3M Health Care, 1997, 4 pages.
Gupta et al., "Differentiating Negative Pressure Wound Therapy Devices: An Illustrative Case Series", Wounds, vol. 19, No. 1, Jan. 2007, pp. 1-9.
US 7,186,244, 03/2007, Hunt et al. (withdrawn)

* cited by examiner

FIG. 6A  FIG. 6B

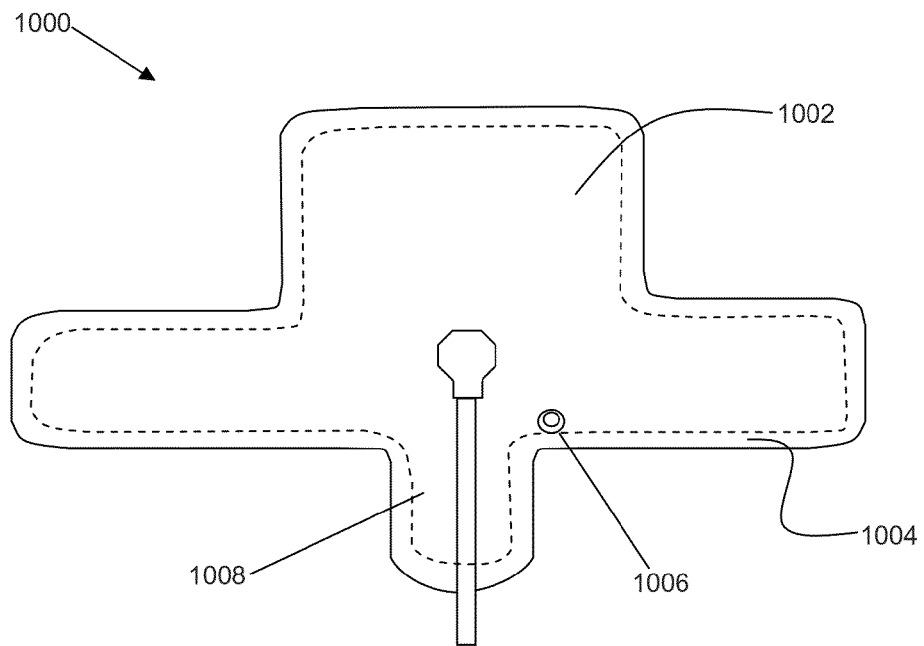
FIG. 10A
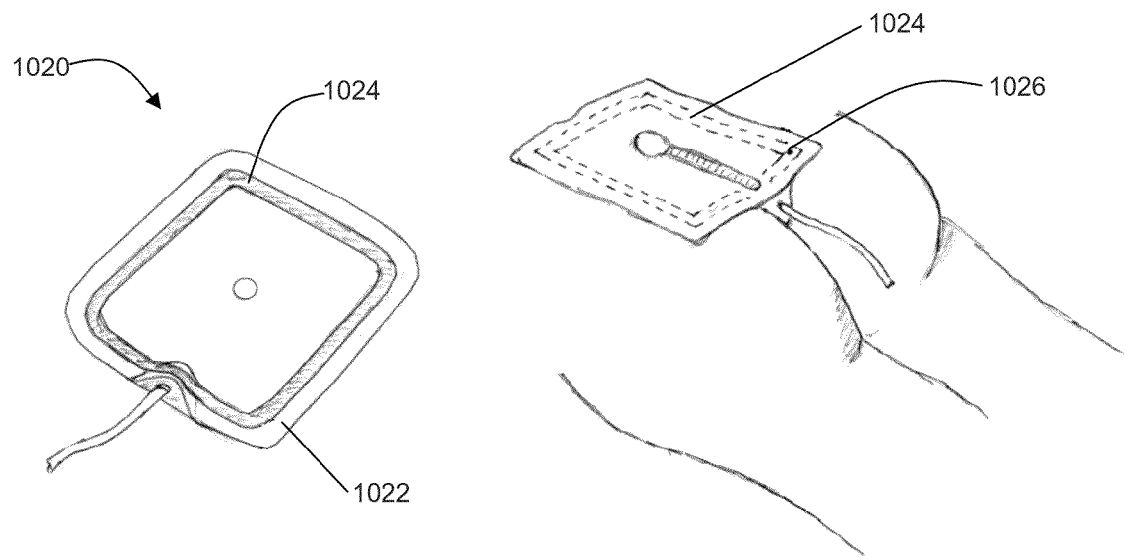
FIG. 10B  FIG. 10C

REDUCED PRESSURE THERAPY OF THE SACRAL REGION

CROSS-REFERENCE TO RELATED APPLICATIONS

This application is a continuation of U.S. application Ser. No. 12/683,987, filed Jan. 7, 2010, now U.S. Pat. No. 8,361,043, issued Jan. 29, 2013, which claims benefit under 35 U.S.C. §119(e) to U.S. Provisional Ser. No. 61/143,030, filed on Jan. 7, 2009, which is hereby incorporated by reference in its entirety.

BACKGROUND

Pressure sores or decubitus ulcers classically result from localized tissue ischemia at pressure points on a patient's skin associated with immobility. However, friction and maceration at the skin site may also be contributing factors. Common locations of decubitus ulcers include the heel, the ankle, the sacral region, the coccygeal region, the ischial region, the knee, and the elbow. Traditional therapy for pressure ulcers has focused on prevention of these ulcers, due to the difficulty of treating the ulcers once they have formed. These treatments include nursing protocols to frequently turn or change the position of bedbound patients, as well as equipment to redistribute focal forces acting on a patient's skin, such as foam boots and fluidized beds. Recently, the delivery of reduced pressure wound therapy (RPWT) has shown promise in the treatment of decubitus ulcers. Typically, RPWT involves creating an enclosed space around a wound and connecting this enclosed space to a reduced pressure source. The creation of the enclosed space is achieved most commonly with an adhesive-coated thin polyurethane film. A conduit, typically a port that may be connected to flexible tubing, from the enclosure created by the adhesive barrier usually is used to connect to the reduced pressure source which facilitates reduced pressure application to the wound site as well as removal of wound exudates. RPWT has been shown to accelerate or promote the healing of a variety of chronic wounds, including diabetic ulcers, venous stasis ulcers, surgical wounds and traumatic wounds.

BRIEF SUMMARY

Disclosed herein are devices and methods for reduced pressure therapy of the sacral region. A dressing system that accommodates the anatomic particularities of the sacral region may be used to provide a substantially airtight seal for RPWT.

One variation of a dressing system may comprise a base layer and a sacral sealing region. The base layer may have a first and second surface, an interior region and an outer perimeter, where an adhesive layer may be located on the second surface of the base layer and substantially along the outer perimeter of the base layer. The sacral sealing region may comprise a non-planar configuration with a peak region that has a generally tapered shape. The tapered shape of the sacral sealing region may extend from the outer perimeter towards the interior region of the base layer, and from the second surface of the base layer to a peak region projecting from the second surface. The sacral sealing region may be integrally formed with the base layer, or may have a sacral sealing structure that may be attached to the base layer. The sacral sealing structure may be attached at the point of manufacture, or may be attached at the point of use.

Some variations of a sacral sealing region may further comprise a cavity. Optionally, a sacral sealing region may comprise a foam located in the cavity. A sacral sealing region may comprise an access valve in communication with the cavity, where the access valve may be located on a first surface of the sacral sealing region.

A device that may be used to create a substantially airtight seal for RPWT may comprise a base layer and an adhesive located on the base layer. The base layer may comprise a first surface, a second surface, an interior region and an outer perimeter, and a non-planar sealing region located about the outer perimeter of the base layer. The adhesive may also be located on at least a portion of the sealing region. The non-planar sealing region may be integrally formed with the base layer, or may be attached to the base layer at the point of manufacture. Some variations of a non-planar sealing region may comprise one or more tapered regions with a taper length and slope, and one or more taper peaks. Tapered regions may have one or more elastic regions configured to change the taper slope when stretched. Certain variations of a non-planar sealing region may further comprise a cavity. These non-planar sealing regions may further comprise a pushing element located in the cavity, where the pushing element is configured to push outwardly against the cavity. In some variations, the pushing elements may comprise a filament that is coupled to a taper peak, and extends along a taper length. Pushing elements may also comprise a sack containing an expandable element, where the expandable element may be a foam or a fluid. The device may also further comprise tubing located within the base layer, tubing directly attached to the first surface or the second surface of the base layer, or even directly attached to both the first and second surface of the base layer.

BRIEF DESCRIPTION OF THE DRAWINGS

FIGS. 6A and 6B are posterior and anterior views of another dressing system comprising a port located on a tissue-contacting side of the dressing.

FIG. 10A is a posterior view of a dressing configured for use with an injectable adhesive. FIG. 10B is an anterior perspective view of another example of a dressing configured for use with an injectable adhesive. FIG. 10C depicts the use of the dressing of FIG. 10B on a patient.

FIG. 18B depicts a RPWT garment with sealable bands. FIGS. 18C and 18D are posterior and side elevational views of another example of a sacral dressing support garment.

DETAILED DESCRIPTION

Figure 1:
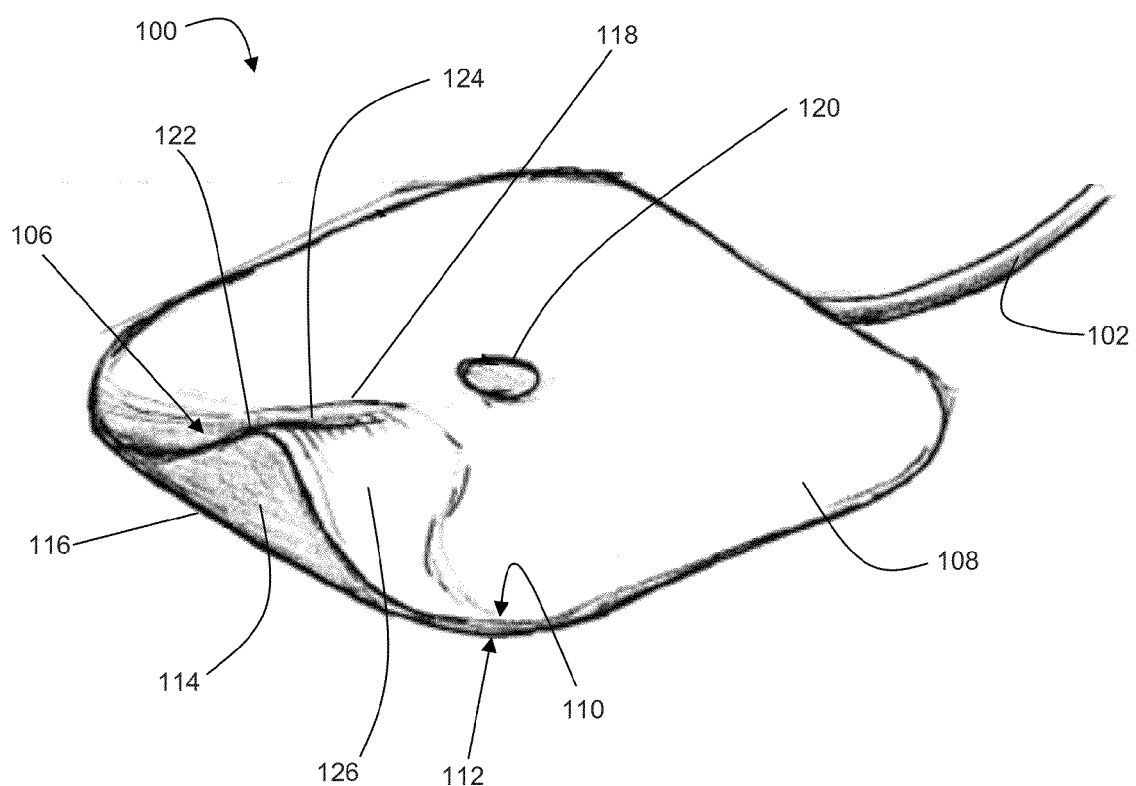
FIG. 1 depicts an anterior perspective view of an example of a dressing system that may be used for RPWT of the sacral region.

Some anatomical regions have contours or geometries that make application of a pre-fabricated planar dressing more challenging, especially for RPWT where a seal between the skin and dressing is used to generate therapeutic vacuum at the wound site. For example, some anatomical regions that have rounded protrusions, one or more curves, protrusions, infolds, creases, indentations, and/or crevices, may affect the formation of an airtight seal between the dressing and the skin surface. Examples of anatomic locations where this may occur are around or between finger and toes, between folds of fatty tissue, the axilla, the groin, the perineal region, the antecubital fossa, the inframammary fold, etc. Many traditional dressings are not adapted to be easily positioned within the abrupt curves and indentations of a skin fold, and are not easily adhered to the skin of a crease or fold to create a sufficiently airtight seal for RPWT.

The complex contours of the sacral region pose a particular challenge to applying a substantially airtight dressing for RPWT. The sacral region comprises gluteal regions and an intergluteal cleft. Other skin folds adjacent to the sacral region include the gluteal creases that separate each gluteal region from the thigh. The anatomical delineations provided by the cleft and creases may vary depending upon elasticity of the skin and/or loss of muscle mass. The intergluteal cleft is located between the two gluteal regions, and generally forms an angular shape, e.g., triangular, where the apex of the angle points into the cleft fold. Due to the narrow width and the steep taper of the cleft, it may be difficult to apply a dressing to the skin within the cleft to create an adequate seal. Additionally, the shape and size of the intergluteal cleft and gluteal regions may vary for different patients. The variability of the skin contours may increase the number of leakage channels of a typical dressing when applied to the skin in these areas.

In addition to challenges due to varied anatomical contours, maintaining a sufficiently airtight seal between a dressing and a folded skin surface for RPWT is subject to other factors that can affect the seal of the dressing. These factors may include mechanical deformation caused by patient movement, accumulation of moisture (e.g., sweat or interstitial fluid), and by the reduced pressure itself. In addition, adhesive films can, upon removal, be traumatic to the delicate peri-wound skin, which may make it difficult to treat smaller satellite wound lesions in these areas.

For example, forming a dressing seal in the sacral region can also be compounded by motion in the region during various activities, for example, bathing or physical therapy for bedridden patients or daily activity for mobile patients. The flexion and movement of tissue in the sacral region, as well as the accumulation of moisture and possibly fecal matter, may also make it difficult for dressings to create an adequate seal. The motion of tissue can further contribute to progressive separation of dressing adhesive surfaces from desired sealing surfaces.

Disclosed herein are dressings that may be used with RPWT of the sacral region and other folded, creased, contoured or clefted regions of the body. The dressing may provide a substantially airtight seal in the sacral region by closely approximating the contours of the sacral region so that the dressing may adhere to the skin surface with fewer leakage channels. Methods of applying dressings to the sacral region to attain an airtight seal are also described herein.

In some examples, the dressing for RPWT may be configured to form an airtight seal around the gluteal region, the gluteal folds, and/or the intergluteal cleft. Since the dimensions and shape of the gluteal region and the intergluteal cleft vary for individual patients, the dressing for RPWT may have different geometries and sizes to accommodate this variety in anatomy. In addition, because the sacral region may be a site of increased moisture accumulation due to sweat, excrement of fecal matter, and reduced exposure to air (e.g., sitting or lying obstruct air flow to the buttocks area), the adhesive of a RPWT dressing may be substantially moisture-resistant, such that the adhesive bond is not significantly or quickly affected by moisture. In other examples, the adhesive may be moisture-absorbent to reduce maceration of the adhered skin, and may also be selected to weaken over time to reduce peri-wound tissue damage when the dressing is removed. The dressing or dressing system may also be configured to reduce pressure points in the sacral region, and may be arranged to treat multiple wound sites. Supportive undergarments and devices may also help the RPWT dressing maintain an adequately airtight seal in the sacral region as the patient assumes any position (e.g., sitting, standing, lying, etc.) or movement (e.g., walking, rolling, bending, etc.).

Generally, dressings for RPWT may comprise a substantially planar structure with an adhesive surface, that acts as an occlusive cover layer or base layer which is then applied over the wound after filling the wound with a contact material such as gauze, foam, or other porous materials. The contact material may reduce dead space in the wound, and may provide cushioning and distribute the reduced pressure throughout the wound bed. The adhesive covering may create a substantially airtight enclosure which encompasses the wound. This enclosure may be in fluid connection with a reduced pressure source. The reduced pressure source may comprise an electric vacuum pump, in-wall suction, or a non-electrically powered suction device. The fluid connection between the vacuum source and the occlusive covering may be provided by a conduit which communicates with an opening in the occlusive covering. In some variations, the conduit may pass through the dressing to be in fluid communication with the wound bed.

In some variations, dressings for RPWT of the sacral region may comprise a planar region for sealing with the skin of the portion of the gluteal region, and a non-planar region that may protrude from the planar region that is adapted to form a sufficiently airtight seal with the skin of the intergluteal cleft. This non-planar region may have one or more pre-formed shapes, such as peaks and/or tapered regions, and may facilitate adhesion to folds or creases in the intergluteal cleft. In some variations, the fold-sealing region is formed from the planar region. For example, the planar region may be pre-folded, pre-creased, and/or scored to form the fold-sealing region, and then heat-set or chemically treated to maintain a non-planar shape. In other variations, the fold-sealing region may be formed with the planar region, for example, by injection molding, liquid injection molding, compression molding, transfer molding, and the like. Fold-sealing regions may also be formed separately from the planar region of the dressing, and attached to the planar region using an airtight mechanism prior to, or during, use. In this variation, fold-sealing regions of different sizes and shapes may be chosen to best accommodate a patient's anatomy, and subsequently attached to the planar portion of the dressing to create an airtight seal along and within the intergluteal cleft. The fold-sealing region and the planar dressing layer may be integrally formed or may be joined together at an airtight interface. In the latter example, the fold-sealing region may be joined to the dressing layer by heat-sealing, radio-frequency welding, laser welding, ultrasonic welding, solvent welding, polymer adhesives, and the like.

Certain variations of a dressing for RPWT may also have fold-sealing regions or structures that incorporate or are configured to accommodate a port or tubing used to connect the wound bed with a reduced pressure source. The port and/or tubing may have a low-profile and be substantially flat, which may help to reduce pressure points introduced by the dressing in the sacral region when the patient is in the sitting or prone position. Commonly utilized conduits, ports, and tubing that may be used to provide reduced pressure therapy at a wound site have been described in pending U.S. patent application Ser. No. 12/626,426, filed on Nov. 25, 2009, which is hereby incorporated by reference in its entirety.

As stated previously, the fold-sealing region may itself be non-planar, e.g., may be three dimensional, with a length, depth, and width. The degree to which the fold-sealing region protrudes from the planar region, i.e. the depth, may be selected in part by the depth of the intergluteal cleft of the patient, and may be sized so that the fold-sealing region adheres to the skin along the contours of the cleft. Additionally, the fold-sealing region may be located at an outer edge of the dressing, such that the width of the fold-sealing region extends along at least a portion of the outer edge. Optionally, the fold-sealing region width may be located along a first edge, and the width may extend between a second and/or third edge. The width and length of fold-sealing region may be selected so that a sufficiently airtight seal may be formed at or near the intergluteal cleft, relative to the location of the sacral or coccygeal wound, or at any other contoured anatomy site adjacent to a skin treatment site.

One example of a dressing (100) for RPWT of the sacral region is shown in FIG. 1, which depicts the skin-contacting surface, i.e., lower surface (110) or anterior surface (relative to the anatomical position of the patient), of the dressing (100) that is opposite of the upper surface (112) or posterior surface (relative to the anatomical position of the patient). The dressing (100) comprises a base layer (108), a port (not shown) that may be in fluid connection with a sacral wound, tubing (102) that may provide a conduit between a reduced pressure source and the wound bed via the port, and a fold-sealing region (106) located on one edge of the base layer (108). Variations of ports and tubing that may be used with a dressing for RPWT have been described in pending application U.S. application Ser. No. 12/626,426, filed on Nov. 25, 2009, which has been previously incorporated by reference in its entirety.

The fold-sealing region may have creases, folds, bends, curves, protrusions, ridges, projections, perforations, and the like, that may help the fold-sealing region closely approximate the skin contours of the intergluteal cleft for the formation of a substantially airtight seal. The fold-sealing region may be pre-configured to protrude from the base layer and may approximate the contour of the skin along the intergluteal cleft. The fold-sealing region (106) further comprises an adhesive region on the skin-contacting surface to create an airtight seal with the skin in the intergluteal cleft. As described previously, the intergluteal cleft may form an angle with an apex within the cleft fold. Similarly, the fold-sealing region may have a tapered or an angular shape, such as a triangular shape, that may facilitate sealing of the dressing along the taper of the intergluteal cleft. In some variations, the fold-sealing region may have a shape with a tapered region that fits into the crease of the intergluteal cleft. For example, the fold-sealing region may be shaped similar to a pyramidal or triangular prism or tent, where a tapered portion of the prism or tent may be configured to fit into the crease of the intergluteal cleft. A fold-sealing region may also be crest-shaped, with a rounded oval portion tapered at one end. The tapered region of the crest may be shaped to fit along the skin surface of the upper portion of the intergluteal cleft and/or the gluteal regions. In some variations, a fold-sealing region may be tapered along a length that is parallel to the longest dimension of the intergluteal cleft, such that the widest portion of the taper is along an outer edge of the dressing, and the narrowest portion of the taper is located towards the center of the dressing. The fold-sealing region may also be configured to be malleable so that it can be stretched and deformed into a trough or depression to fit creases, folds, and clefts in sacral regions that may have different dimensions and geometries. This may help mitigate introduction of additional pressure points to the sacral region, as well as create and maintain an adequately airtight seal. In some variations, the skin contact portion of the fold-sealing region may be made of the same occlusive material as the other portions of the dressing base layer. The fold sealing region may comprise a structure that is integrally formed with the occlusive cover or may be separately formed and attached, or may be formed by folding and attaching a portion of the occlusive cover back onto itself. The fold-sealing structure may be open or closed shape, and may have a solid, hollow, or porous interior. Examples and other variations of the base layer and the fold-sealing region are described below.

Figure 2A:
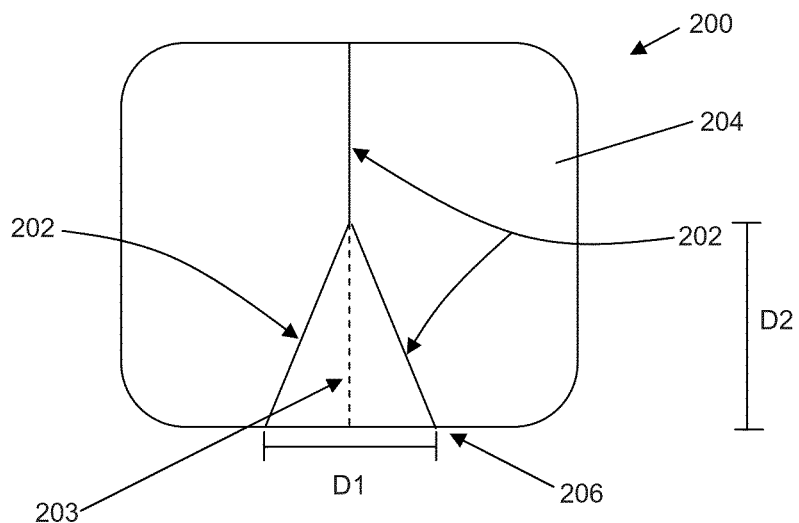
FIG. 2A is a schematic posterior view of a variation of a fold-sealing region of a RPWT dressing.
Figure 2B:
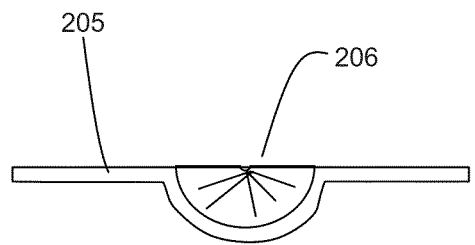
FIG. 2B is an interior elevational view of the dressing in FIG. 2A.

In the example of FIG. 1, the fold-sealing region (106) comprises a closed triangular pyramidal shape having an inferior face (114) located at an outer edge (116) of the dressing (110) and an interior corner or apex (118) located between the base and the interior of the dressing (110), e.g. toward the central vacuum opening (120) of the dressing (110). In some configurations, the inferior face (114) is generally oriented in a plane that is perpendicular to the general plane of the dressing (100), but in other examples, the base face may be generally oriented in a plane that is at a non-perpendicular angle. The region (106) further comprises an anterior apex (122) comprising the point or area of the region (106) that is the greatest distance from the general plane of the dressing (100). The region (106) also comprises an anterior crest (124) between the anterior apex (122) and the interior apex (118), along with a base face (not seen in FIG. 1) that is generally co-planar with the general plane of the dressing (100), and two side faces (126) to each side of the crest (124). The crest may have a linear or non-linear configuration, including generally convex and concave configurations. In other examples, the fold-sealing region may comprise an anterior surface rather than an anterior crest or fold. The interior of the fold-sealing region (106) may be solid, may be porous or may comprise a one or more cavities. The surfaces of the fold-sealing region (106) may comprise the same or different materials as the materials comprising the anterior and posterior FIG. 2A illustrates another example of a dressing (200) for RPWT. As shown there, a base layer (204) has a plurality of pre-configured folds or creases (202), where the creases (202) may form a general Y-shape. Creases and/or folds on the substantially planar base layer (204) may help the substantially two-dimensional base layer (204) accommodate the contour of the sacral region or facilitate initial positioning of the dressing (200) into the intergluteal cleft by folding the dressing along the creases (20). The portion of the base layer that is enclosed in the Y-shaped crease (202) forms a fold-sealing region (206) when the creases are folded. FIG. 2B depicts one example of how a non-planar, pre-formed fold-sealing region (206) may form a seal along a sacral contour (205) that has a curved indentation, e.g., a wound bed. Optionally, the dressing (200) may have a midline crease (203). The fold-sealing region (206) may be sized according to the geometry of a patient's intergluteal cleft. The dimension (D1) may be determined in part by the depth of the intergluteal cleft and may be a multiple of that depth, e.g., dimension (D1) may be approximately less than, equal to or more than twice the depth of a patient's intergluteal cleft or the depth to which the practitioner determines is necessary for the dressing (200) to provide an airtight seal with the skin of the intergluteal cleft of the particular patient in question. The dimension (D2) may be determined in part by the length of the intergluteal cleft. While the fold-sealing region (206) is shown to be formed from the dressing (200), in other variations of a dressing for RPWT for the sacral region, the fold-sealing region may be separately manufactured and then attached to the dressing prior to use.

Figure 2C:
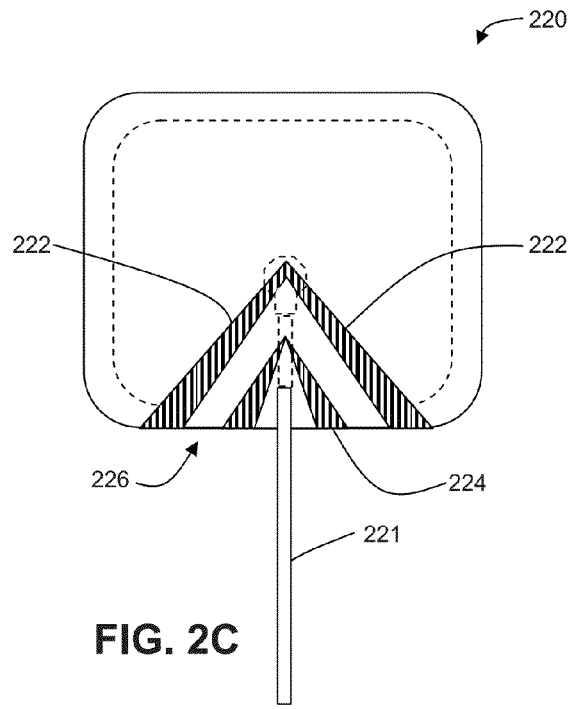
FIG. 2C is a schematic posterior view of another variation of a dressing with a fold-sealing region comprising one or more elastic regions.
Figure 2D:
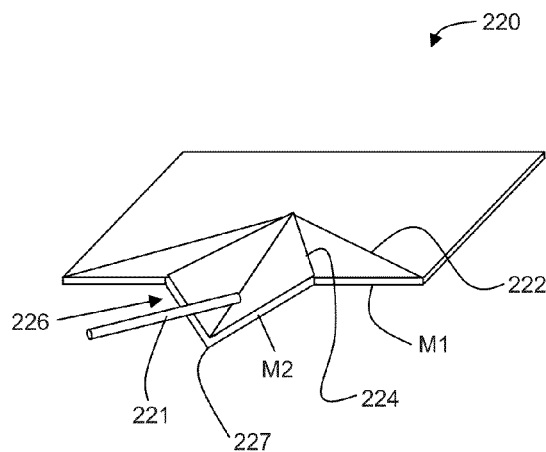
FIG. 2D is a posterior perspective view of the dressing in FIG. 2C and FIG. 2E schematically depicts the dressing of FIG. 2C applied to the sacral region of a patient.
Figure 2E:
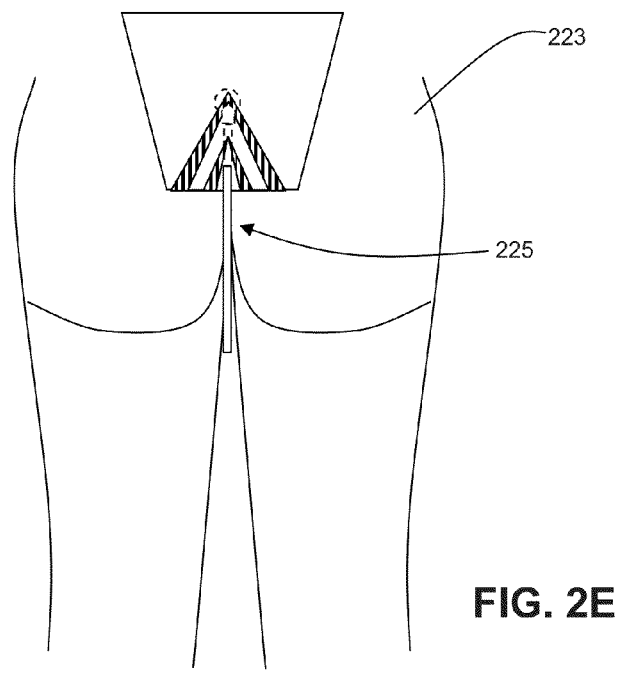
FIGS. 2F and 2G schematically illustrate the dimensions of two examples fold-sealing regions.
FIGS. 2H-2K depict variations of a fold-sealing region comprising a cavity.
FIG. 2L depicts a variation of a dressing with a rounded, bi-lobular geometry and a fold-sealing region comprising a cavity.

Sacral dressings may also comprise highly deformable regions, e.g., elastic or flexible regions, which are more compliant than the bulk of the dressing layer. An elastic region may provide greater conformability to the contours of the sacral region. After being stretched, the one or more elastic regions may be able to return to its un-stretched shape, e.g., may have shape-memory. The stretching may be performed, for example, as the dressing is being applied to the patient, or may occur during patient movements, such as walking, sitting, bending, etc. In some examples, the 100% elastic modulus of the elastic region may be in the range of about 0.1 pound-force (lbf) to about 2 lbf for every 25 mm width of the material comprising the elastic region, wherein the width is transverse to the direction of tension exerted onto the material. In other examples, the 100% elastic modulus may be in the range of about 0.5 lbf to about 1 lbf per 25 mm width, or about 0.3 lbf to about 1.5 lbf per 25 mm width of material. In some variations, these elastic regions may be arranged along creases in the base layer and/or the fold-sealing region. One variation of a dressing with one or more elastic regions is shown in FIG. 2C. Dressing (220) has a first elastic region (222) and a second elastic region (224), where the first elastic region (222) is arranged as a V-shape, and the second elastic region (224) is arranged as a V-shape nested in the V-shape formed by the first elastic region (222). The first and second elastic regions may radiate from the portion of the dressing (220) which is configured to reside along a corner of the intergluteal cleft and extend toward the edges of the dressing (220) to help the dressing to conform to the contours of the intergluteal cleft more easily. The first and second elastic regions may be made of highly elastic dressing substrates and adhesives, such as elastic polyurethanes and acrylic or hydrocolloid adhesives. Alternatively, the dressing (220) may be made of a more elastic material that easily stretches and conforms to fit the contours of the intergluteal cleft. Providing elastic regions to a dressing, and/or making a dressing out of elastic materials may help the dressing to bend and conform to the body during normal body movement to reduce the potential for stress concentrations that may lead to the separation of the dressing from the body. In other variations, the dressing (220) may comprise an elasto-plastic or plastically deforming material which is highly compliant and deformable to conform the contours of the patient anatomy. Tubing (221) may extend from a location that is co-linear with the vertices of the first elastic region (222) and the second elastic region (224), but in other variations the tubing (221) may be located anywhere on the dressing (220) that is in fluid communication with the wound bed. The tubing may comprise materials such as silicone, urethane, polyurethane, polyvinyl chloride (PVC), any of a variety of thermoplastic elastomers (TPEs) such as styrene-ethylene-butylene-styrene (SEBS), for example. The tubing (221) may have a low profile and pass through a cavity portion the fold-sealing region (226) to help reduce pressure points in the sacral region when the patient is in a sitting or prone position. FIG. 2D schematically depicts a perspective view the three-dimensional geometry of the dressing (220) when creased along the first elastic region (222) and the second elastic region (224). The tubing (221)

may extend from the dressing (220) through the fold-sealing region (226). One example of how the dressing (220) may be applied to a patient (223) is shown in FIG. 2E, where the tubing (221) may extend from the dressing along the intergluteal cleft (225), between the two gluteal regions.

Figure 2F:
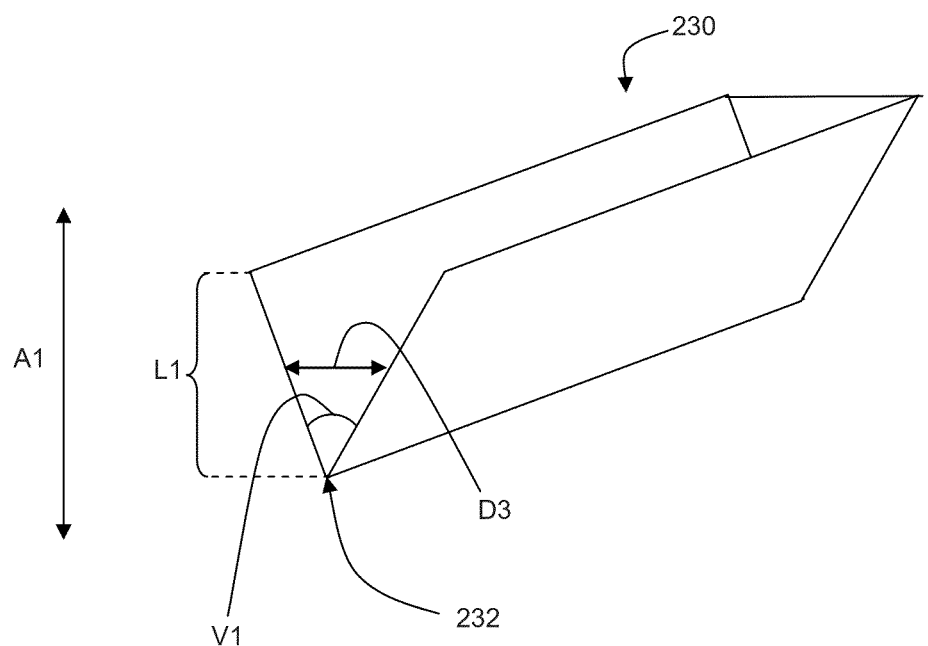
Figure 2G:
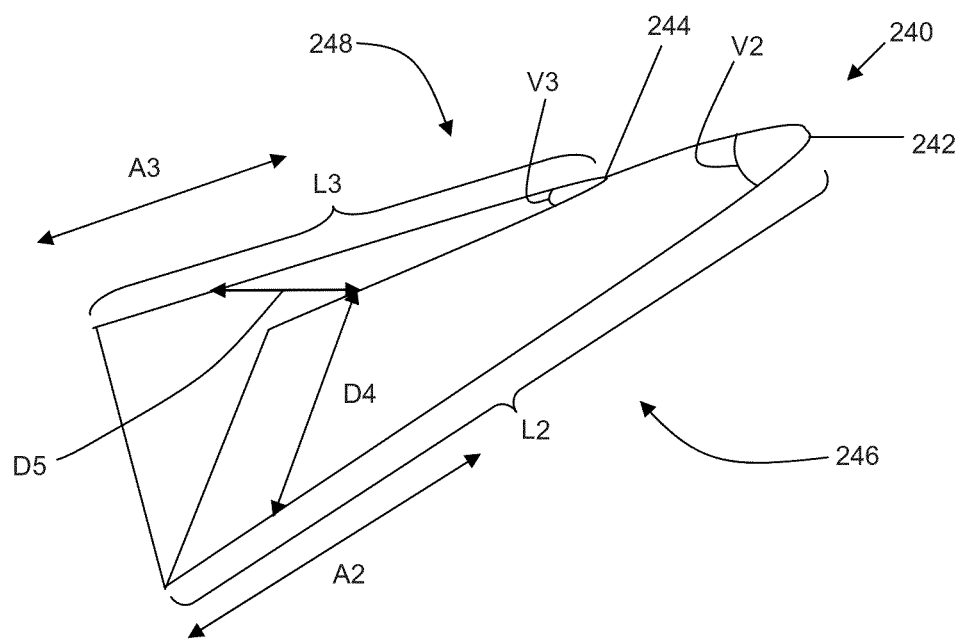

As mentioned previously, the fold-sealing region may be fin-shaped, tent-shaped, crest-shaped, or may be an appropriately shaped ridge, prominence, or other appropriate form factor. The geometry of various fold-sealing regions or structures may be characterized in a variety of ways, as illustrated in FIGS. 2F and 2G. FIG. 2F depicts a variation of a fold-sealing region (230), where the fold-sealing region (230) is tapered such that the dimension (D3) varies along axis (A1), e.g., dimension (D3) generally decreases along a taper length (L1) to a corner or apex (232). The dimension (D3) and the length (L1) may be varied according to the anatomy of the patient. Axis (A1) may be generally perpendicular to the plane in which the rest of the dressing resides. The taper of fold-sealing region (230) may have any length (L1) according to the anatomy of the intergluteal cleft. The length (L1) may be from about 1 centimeter to about 12 centimeters, for example, from about 1 centimeter to about 3 centimeters, or from about 2 centimeters to about 5 centimeters. The largest value of the dimension (D3), i.e., the overall width of the fold-sealing region, may be from about 2 centimeters to about 20 centimeters, for example, from about 3 centimeters to about 5 centimeters, or from about 4 centimeters to about 6 centimeters, or from about 8 centimeters to about 15 centimeters. The dimension (D3) and the length (L1) may be varied according to the anatomy of the patient, for example, larger patients may have larger intergluteal clefts, and obese patients may have a deeper intergluteal cleft. Some variations of a fold-sealing region may have a taper with one or more taper slopes (i.e., the change in dimension (D3) over a length along axis (A1)). For example, a fold-sealing region may have one taper slope along the entire length of the taper, as exemplified in FIG. 2F, or may have two or more taper slopes along the length of the taper, as exemplified in FIG. 2D. The taper of the fold-sealing region (226) in FIG. 2D has a first slope (M1), and a second slope (M2) that is greater than the first slope (M1), as the taper converges at apex (227). The slopes of the tapers may be in the range of about 0.25 to about 1, or about 1 to about 10, or about 5 to about 15, etc. In some variations, the fold-sealing region taper may converge at angle. For example, the fold-sealing region (230) has a taper that converges at the apex (232), where the apex (232) has an angle (V1). The angle (V1) may vary from about 0° to about 180°, sometimes 10° to about 150°, or other times from about 10° to about 90°, and other times from about 20° to about 50°. The various dimensions and geometries of the fold-sealing region may be pre-configured or pre-shaped for a particular dressing, and a practitioner may have a variety of dressings with fold-sealing regions of different widths, depths, and lengths to choose from when preparing a patient for RPWT.

FIG. 2G depicts a variation of a fold-sealing region (240) comprising multiple tapered sections. A first additional taper (246) is formed by varying dimension (D4) along axis (A2), e.g., dimension (D4) generally decreases along length (L2) to an apex (242). A second additional taper (248) is formed by varying (D5) along axis (A3), e.g., dimension (D5) generally decreases along length (L3) to the corner or apex (244). While the first and second additional tapers do not converge in the fold-sealing region (240), in some variations, the first and second additional taper sections may converge, i.e., apices (242) and (244) may be coincident. As described above with regard to the taper in FIG. 2F, the first and second tapers may each have one or more taper ratios, slopes, and angles of convergence. For example, the first additional taper (246) may have any length (L2) according to the anatomy of the intergluteal cleft. The length (L2) may be from about 5 centimeters to about 12 centimeters, for example, from about 4 centimeters to about 6 centimeters, or from 6 centimeters to about 15 centimeters, or from 16 centimeters to about 24 centimeters. The largest value of the dimension (D5), i.e., the width of the fold-sealing region, may be from about 2 centimeters to about 10 centimeters, for example, from about 3 centimeters to about 5 centimeters, or from about 4 centimeters to about 6 centimeters. The largest value of the dimension (D4) may be from about 1 centimeter to about 12 centimeters, from 2 centimeters to about 10 centimeters, or from about 3 centimeters to about 6 centimeters, or from about 4 centimeters to about 8 centimeters. The first additional taper (246) may have one or more taper slopes, where the taper slopes may be from about 0.25 to about 1, or from about 1 to about 10, or from about 5 to about 15, etc. The first additional taper (246) may converge to apex (242) with an angle (V2), where V2 may vary from about 0° to about 180°, sometimes about 10° to about 150°, or other times from about 10° to about 90°, and other times from about 20° to about 50°. The second additional taper (248) may have characteristics similar to, or in the range of the first additional taper (246).

Although the examples in FIGS. 2F and 2G depict configurations that taper distally to a point or line from the base of the fold-sealing region, in other variations, the peak or distalmost region of the fold-sealing region may taper to a surface, e.g. the fold-sealing region may comprise a truncated geometry, such as a frusto-conical shape or a trapezoidal cross-sectional shape. These variations may be further characterized by the ratio of the largest value of dimension (D3) to the smallest value of dimension (D3) about the peak or distalmost region. In some specific examples, this ratio may be in the range of about 4:3 to about 20:1, sometimes about 2:1 to about 10:1, and other times about 3:1 to about 8:1. In variations where the peak region comprises a surface, this distalmost surface may be generally parallel or non-parallel with respect to the base layer of the dressing. The skew angle between the plane of the base layer and the plane of the distalmost surface, if present, may be in the range of about 1° to about 45° or more, sometimes about 5° to about 30°, and other times about 10° to about 25°.

While corners or apices (232), (242), and (244) are shown to be acute angles, i.e. pointed, in other variations, one or more may be rounded or blunt. Fold-sealing regions that may be used to create a sufficiently airtight seal in the intergluteal cleft region for RPWT may have one or more of the tapers described above, with any number of taper ratios, taper slopes and/or apical convergence angles, in any combination that is suitable for forming a seal with the skin along the unique anatomical contours in the intergluteal cleft region of each patient. The taper ratio, taper slope and the angle of the apex of any of the tapers previously described may be adjusted (e.g., stretched, molded, etc.) as the dressing is positioned in the sacral region near and into the intergluteal cleft. The fold-sealing region may also be configured to interface with positioning aids that may help to attach the fold-sealing region to the skin within the intergluteal cleft. Examples of positioning aids may include suture threads, inflatable members, surgical spreaders, etc. Fold-sealing regions may also be configured accommodate one or more conduits that form a connection between a low pressure source and the wound bed.

Figure 2H:
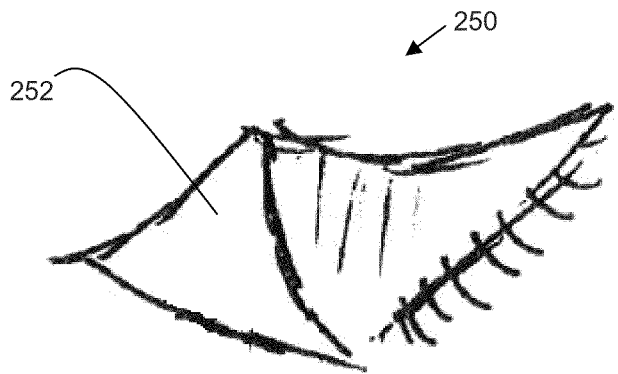

The anatomically shaped fold-sealing regions described above may enclose a cavity, an example of which is shown in FIG. 2H. As depicted there, the fold-sealing region cavity (252) of fold-sealing region (250) may be hollow. In some variations, to facilitate insertion of the fold-sealing region into a fold or cleft, a spatula or other instrument with a flat edge may be used to push the fold-sealing region deeper. In other variations, a line or ribbon that extends along the length of the fold-sealing region to help insert the fold-sealing region into the cleft, as well as to help press the adhesive portions of the fold-sealing region to the skin in the cleft. For example, the line or ribbon may be tensioned and pulled against the posterior surface of the dressing, along the contours of the intergluteal cleft, to facilitate sealing of the dressing to the cleft. The suture may be removed after an airtight seal has been attained, or may be retained with the dressing to facilitate adjusting the position of the dressing in the event that it is shifted during the treatment.

Figure 2I:
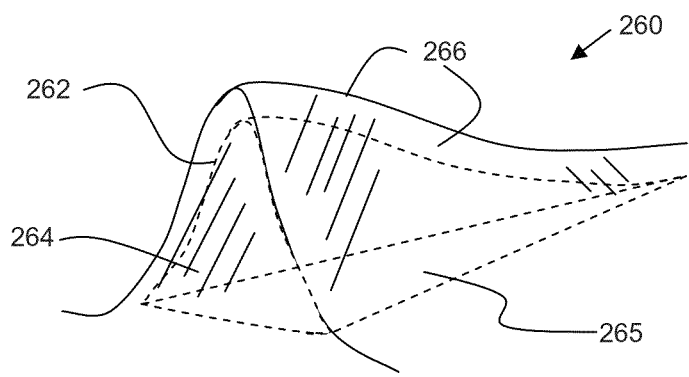

Other variations of attachment feature may contain an inflatable cavity that may help the dressing form a substantially airtight seal in the intergluteal cleft. FIG. 2I depicts one variation of a fold-sealing region (260) that comprises an airtight cavity (262), and a deformable material (264) within the airtight cavity (262). The airtight cavity (262) may generally conform to the shape of the fold-sealing region, and the deformable material (264) contained therein may occupy the majority of the volume of the airtight cavity (262). Adjusting the volume of the airtight cavity may also adjust the dimensions of the fold-sealing region, e.g., increase the depth, length, and/or width of the fold-sealing region. The airtight cavity (262) and the deformable material (264) be formed in a wedge shape that may help to distribute pressure and press down the adhesive portion (266) against the crevice skin when loaded (e.g., loaded by sitting or lying down). The airtight cavity (262) and the deformable material (264) may be a material that is sufficiently conformable as to accommodate different anatomies as well as to mitigate introduction of additional pressure points. For example, the airtight cavity (262) may be made of a polyurethane, a vinyl, silicone, thermoplastic elastomer or other suitable material, and the deformable material may be a urethane foam, a gel, gas, liquid, semi-solid or other fluid material such as a viscous silicone. The cavity may also be filled with particles having any of a variety of shapes, sizes, elastic properties, including solid or hollow microspheres, foam beads or buckwheat, for example. In some instances, the particles may be suspended in a gel or liquid medium. Some variations of a fold-sealing region may have a base region (265). The base region (265) may substantially co-planar with the dressing base layer, or may bulge inwardly or outwardly from the plane of the dressing base layer. Likewise, other faces of the fold-sealing region may also bulge inward or outward. In other variations, the airtight seal is constructed such that it comprises an aperture through which the reduced pressure delivery tubing is directed, thereby reducing potential patient contact pressure points caused by the reduced pressure delivery tubing.

Figure 2J:
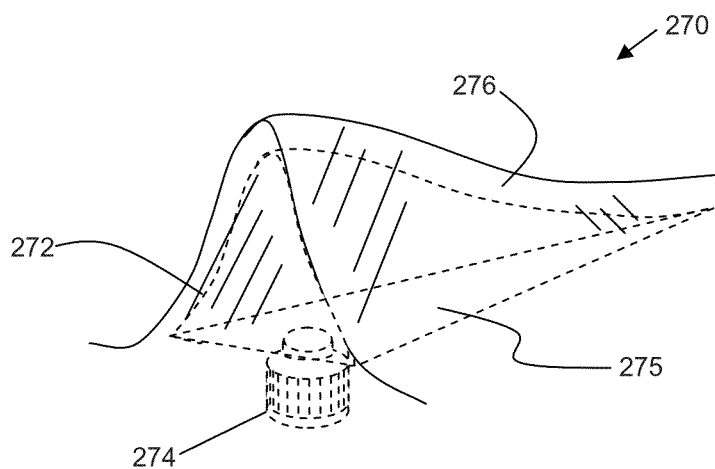
Figure 2K:
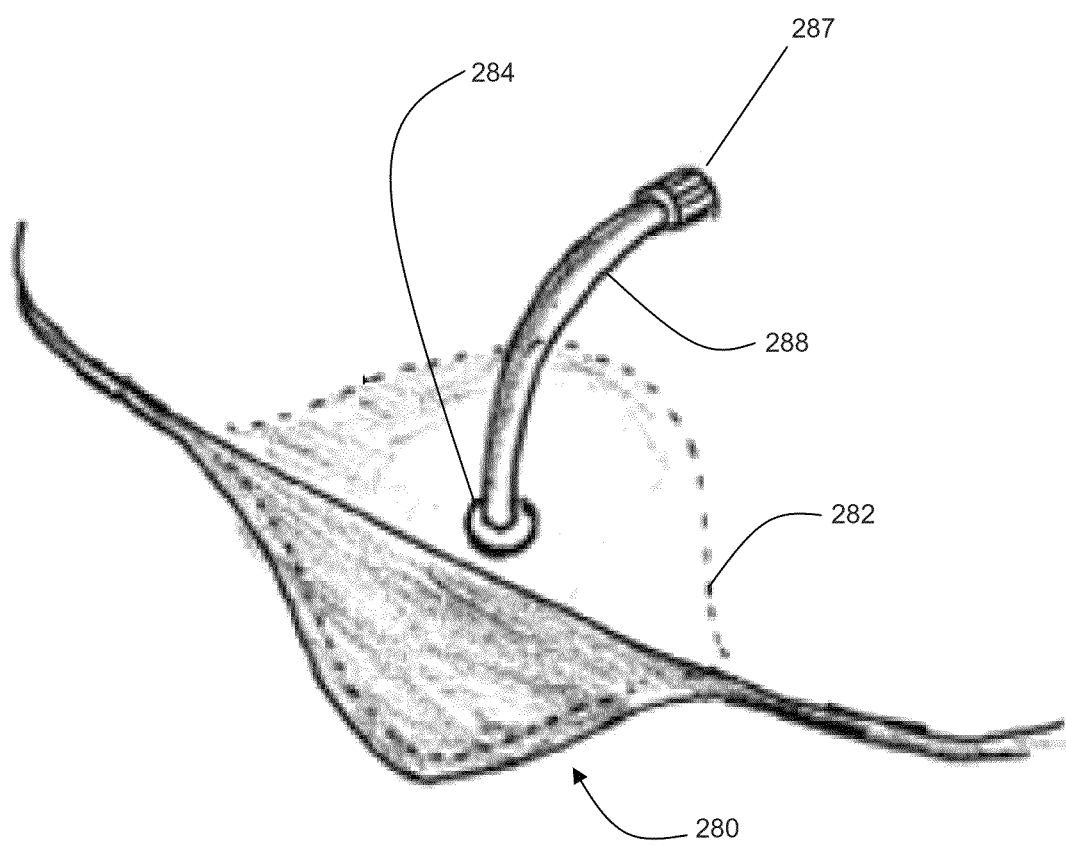
Figure 2L:
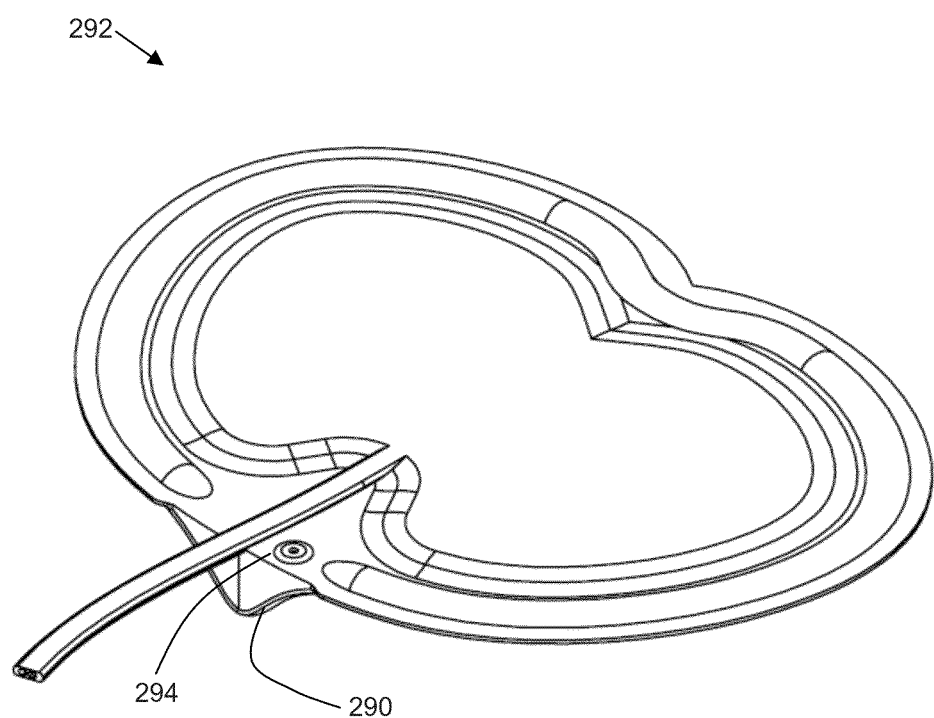

Some variations of a fold-sealing region may comprise a port on the base region, where the port may provide communication to the cavity in the fold-sealing region cavity. The port may be located on the base or the inferior face of the fold-sealing region. The port may be used to introduce and/or withdraw the deformable material described above. FIG. 2J depicts another variation of a fold-sealing region (270) comprising an inflatable cavity (272), a port (274) along a base region (275), and an adhesive portion (276). The inflatable cavity (272) may be expanded by injecting any of the materials described above, and/or a gas, such as helium or nitrogen or ambient air, via the port (274). The pressure of the gas within the airtight volume can be selected to ensure an appropriate fit to the anatomy of the patient, and may then be reduced after the appropriate fit has been attained. The volume of the inflatable cavity (272) may be adjustable to allow inflation or deflation to accommodate individual intergluteal cleft sizes. The inflation and/or deflation of the cavity may be performed any time during the application of the dressing to the treatment site, or even during treatment to accommodate anatomical changes related to increased or reduced swelling, erythema, infection, delamination or other phenomena. In some variations, the cavity may be deflated to some degree if the treatment site develops signs of excessive pressure due prolonged incumbency on the inflated dressing. The cavity may be inflated before, during, or after a) positioning in a skin fold, b) adhesion to the skin, c) removal of the release liner, d) during treatment, and/or e) during removal of the dressing from the skin site. As described above, the inflation and/or deflation of the cavity may be temporarily increased and then decreased. In some variations, the pressure may be temporarily increased to a range of about 2.0 atmospheres to 3.0 atmospheres (e.g., about 1500 mmHg to about 2500 mmHg), and then reduced to be more physiologically compatible, e.g., about 0.1 atmospheres or less (e.g., about 100 mmHg or less). For example, the pressure within the cavity may be increased temporarily during positioning of the dressing, forming an airtight seal, etc., and may be reduced during RPWT. In some variations, the dressing may be manufactured such that there is an initial pressure within the cavity of the fold-sealing region, for example, the cavity may be pre-filled to have a pressure of about 0.1 atmospheres or less (e.g., 100 mmHg or less). Alternatively or additionally, the cavity may be inflated at the point-of-use, as described above. The port (274) may be an opening that is configured to be closed by suitable cap, e.g., friction-fit, snap-fit, screw-fit cap. The port (274) may also be a one-way flow mechanism, for example, a one-way valve, such as a duckbill valve, a slit valve, a spring valve, an umbrella valve or any other suitable one-way valve known in the art. The size and shape of the port (274) may allow inflation of the cavity (272) by a small catheter, tube or other suitable conduit. FIG. 2K depicts one variation of a fold-sealing region (280) comprising an inflatable cavity (282) and a cavity opening (284), where the cavity opening (284) is attached to a tubular portion (288) with an end portion (287). Optionally, a one-way valve as described above may be provided in the inlet (284), tubular portion (288) and/or end portion (287). The end portion (287) may be configured to interface with any tubing or syringes used in the art, for example, by friction-fit, snap-fit, screw-fit, Luer-Lok®, etc. Another variation of a rounded dressing (292) with an inflatable fold-sealing region (290) is shown in FIG. 2L. As shown there, the fold-sealing region port (294) may be a one-way valve as described above, which may not have additional tubing protruding therefrom. This may help to maintain the low-profile of the dressing (292) to limit localized pressures on the sacral region when the patient is in a position that places weight on the dressing (292).

In some examples, the fold-sealing regions may comprise a collapsed or compressed configuration to facilitate its positioning in the skin fold or cleft. In some examples, the fold-sealing region may comprise an inflatable and/or deformable component may be compressed as it is inserted into the cleft, and then expanded to urge the fold-sealing region to adhere to the skin in the intergluteal cleft. Expansion of the inflatable and/or deformable component may also help seat the fold-sealing region at the desired location in the sacral region. Once the dressing has been positioned at the desired location, the inflatable and/or deformable component may remain expanded to maintain that position, as well as to maintain the seal between the fold-sealing region and the skin in the cleft.

Alternatively or optionally, the inflatable and/or deformable component may be collapsed and withdrawn once an initial seal is created between the fold-sealing region and the cleft. The inflatable and/or deformable component may also allow the user to adjust the size of the fold-sealing region by regulating the expansion of the fold-sealing region as the dressing is applied to the patient. For example, the user may inject more or less fluid into the cavity of the fold-sealing region as suitable for creating a substantially airtight seal to the skin in the intergluteal cleft.

Figure 3A:
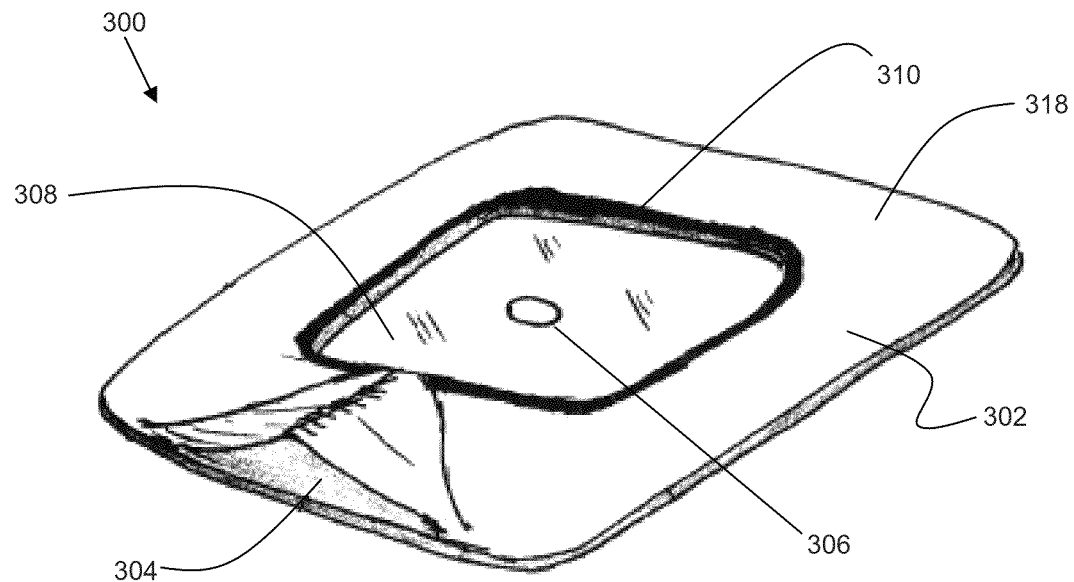
FIG. 3A illustrates an anterior perspective view of a protective layer of a multi-layer dressing system.
Figure 3B:
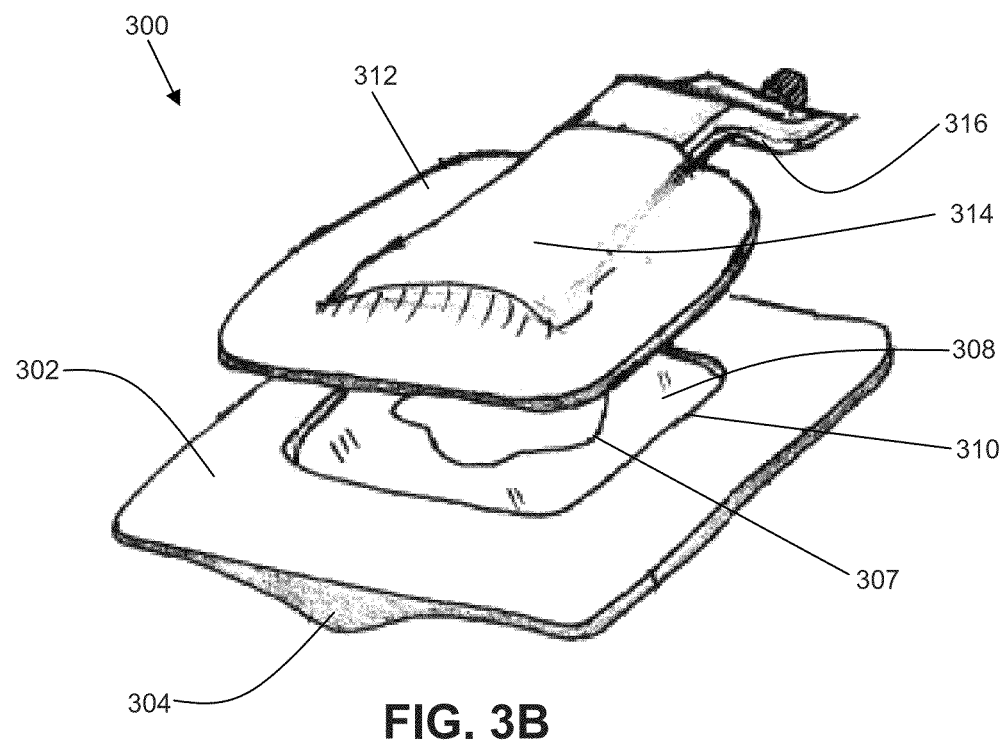
FIG. 3B is a posterior perspective view of an occlusive layer being applied to the protective layer of FIG. 3A.

Some variations of a dressing for RPWT may have multiple layers to help create a robust airtight seal with the peri-wound skin, or to permit removal or separation of a portion of the dressing system without disturbing the adhesive seal between the skin and the dressing system. One variation of a two-layer dressing is shown in FIGS. 3A and 3B. Dressings for RPWT may have any number of layers, where each layer may have a different function. For example, layers of a dressing may serve to deliver therapeutic agents, provide moisture, wick away moisture, adhere to the skin, interface with a port or tubing to a reduced pressure source, allow breathability, protect the wound from the external environment, etc. The dressing (300) shown in FIGS. 3A and 3B comprises a protective cover layer or sheet (302) comprising an adhesive applied to one side to attach to the peri-wound skin and a sealant layer (312) which may comprise tubing (316), and is configured to releasably attach to the upper surface (318) of the protective layer (302). In use, the protective layer (302) may be adhered to the peri-wound skin surface and together with the sealant layer (312) provides an occlusive cover for RPWT. To resist damage to the peri-wound skin when accessing the treatment site, the sealant layer (312) may be separated from the protective layer (302) while the protective layer (302) remains adhered to the peri-wound skin.

The upper surface of the protective layer and/or the adhesive on the sealant layer (312) may be configured to separate from each other when peeled apart while the adhesive between the protective layer (302) and the skin resists inadvertent separation when the sealant layer (312) is peeled off. In some variations, the adhesive on the protective layer and the sealant layer may be the same adhesive, but the surface properties on the upper surface of the protective layer may facilitate peel-off of the sealant layer, which may be similar to the surface of a release liner. In other examples, the t-peel force or blunt probe tack force of the protective layer adhesive may be greater than the t-peel or blunt probe tack force of the sealant layer.

The adhesive properties of the protective layer (302) may be uniform or non-uniform over the lower surface of the protective layer (302), e.g., stronger adhesives may be applied in certain regions, certain regions may lack adhesives, and/or may comprise increased thicknesses or densities of adhesives may be applied in some areas, such as the peripheral edges than at the center. Adhesive agents that may be used to attach the protective layer (302) to the peri-wound site include but are not limited to polyurethane materials, hydrocolloid or hydrogel materials, silicone, pressure-sensitive adhesives, acrylic adhesives, and the like. Adhesive agents may also be activated by moisture, UV, heat, etc. The adhesive portions of the fold-sealing region may be configured to have a gradient in adhesive strength or adhesive thickness, e.g., increased adhesive strength at the locations that form a seal with the skin of the intergluteal cleft, to help ensure maintenance of adhesion in high flexion areas. Other examples of adhesives that may be used are described in pending application Ser. No. 12/626,426, filed on Nov. 25, 2009, which has been previously incorporated by reference in its entirety. In some variations, an antiperspirant material or a moisture absorbent material may be provided to control moisture accumulation in the adhesive portion.

In one example, a polyurethane dressing with hydrocolloid adhesive from EuroMed (Orangeburg, N.Y.) may be used (product number CS20742). In this particular example, dressing comprises the following characteristics: a probe tack in the range of about 200 grams to 600 grams, e.g., about 251 grams to 564 grams or 323 grams, a liner Z-release force in the range of about 0.5 Newtons to about 3 Newtons, e.g., about 0.14 Newtons or less than 2 Newtons, a 100% modulus in the range of about 1.5 Newtons to about 5 Newtons, e.g., about 2 Newtons to about 4.5 Newtons or 2.9 Newtons, an elongation to break parameter in the range of about 90 Newtons to about 300 Newtons, e.g., greater than 100 Newtons or 168 Newtons, a release from plate parameter in the range of about 3 Newtons to about 15 Newtons, e.g., from about 5 Newtons to about 13 Newtons or 7 Newtons, a water absorption (over 24 hours) parameter in the range from about 125 mg/cm$^2$ to about 500 mg/cm$^2$, e.g., greater than 150 mg/cm$^2$ or 387 mg/cm$^2$, a thickness (adhesive and backing layer) in the range of about 0.2 millimeters to about 0.3 millimeter, about 0.2 millimeters to about 2 millimeters, e.g., from about 0.42 millimeters to about 0.62 millimeters or 0.49 millimeters, a length in the range from about 10 centimeters to about 20 centimeters, e.g., about 14.8 centimeters to about 15.2 centimeters or 15 centimeters, and a width in the range from about 10 centimeters to about 20 centimeters, e.g., about 14.8 centimeters to about 15.2 centimeters or 15.2 centimeters. Variations of the dressing may be permeable, semi-permeable, or impermeable to gas and/or liquid. Descriptions of various sheets, base layers, configurations, types, dimensions, and materials may be also found in pending application Ser. No. 12/626,426, filed on Nov. 25, 2009, which has been previously incorporated by reference in its entirety.

Adhesive portions of a dressing for RPWT at the sacral region may be covered by release liners to preserve adhesive properties until ready for adherence, and/or carrier elements or additional liners to maintain the shape of the dressing during application. In some variations, a carrier element and/or release liner may also have sufficient rigidity to support the shape of the dressing while it is applied to the skin, and may have release handles or liners to reduce inadvertent adherence to the user or the patient. In some variations, the carrier element may have a release liner that may be removed prior to applying the dressing. Carrier elements and release liners may have any suitable shape, such as a triangular, rectangular, or round shape, according to the shape of the fold-sealing region. Additionally, release liners may have break lines in different locations on the dressing to help facilitate the application of the dressing so that an airtight seal may be formed. For example, a break line may be located on a central apex and/or tapered edge of a fold-sealing region, e.g., along the midline (203), with a handle on each side of the break line. This configuration may allow the user to apply the adhesive portion to the skin in the deepest portion of the intergluteal cleft first by peeling the two handles away from each other, e.g., in generally opposite directions. As the handles are peeled away from the break line and/or from each other, the adhesive portion of the fold-sealing region may be exposed and gradually smoothed outward, e.g., away from the intergluteal cleft. The direction in which the handles are peeled away may be along the intergluteal cleft, or perpendicular to the cleft. Generally, one handle or release liner may be peeled at a time, or multiple release liners may be peeled substantially simultaneously. Pressing and/or smoothing the adhesive layer against the skin surface as the release liner is peeled may help reduce the occurrence of leak channels in the dressing, and provide a substantially airtight seal. The dressing adhesive may also be temperature sensitive such that the dressing may be repositioned multiple times until positioned in the desired manner at which time heat activation of the adhesive. For example, application of external heat can facilitate sufficient adhesive flow to allow the adhesive to achieve more intimate contact with the skin surface. Heat-activated flow might occur with constituent adhesive materials with glass transition temperatures above body temperature (37° C.). Heat-activated adhesion might also arise due to temperature-sensitive bond manipulation that opens up molecular chains for adhesion to the skin surface. In further examples, the dressing adhesive may be re-heated after the dressing has been applied to the skin to permit repositioning or removal of the dressing, or to re-adhere a portion of the dressing that may have separated from its attachment site. Other variations of carrier elements, release handles, release liners, and any support layers are described in pending application Ser. No. 12/626,426, filed on Nov. 25, 2009, which has been previously incorporated by reference in its entirety.

The protective layer (302) may comprise a central opening or may optionally comprise an inner layer (310) and a fold-sealing region (304), which may be any of the fold-sealing regions previously described. The inner layer (310) comprises an opening (306) and may or may not comprise an adhesive on its lower surface. In some examples, the opening (306) is a vacuum opening. In further variations, opening (3060 may also be used to insert scissors or other cutting instrument to facilitate trimming of the inner layer (310) and increase exposure of underlying wound to the sealant layer 312). In some variations, the inner layer (310) may comprise a flexible or plastically moldable material that may be cut or deformable to the edge shape or other contour of the wound bed. For example, the inner layer (310) may comprise a thinner material that is easier to trim and accommodate the wound size and geometry, or may be pre-configured to accommodate most wound geometries. Optionally, the inner layer (310) may comprise a transparent or translucent sheet or material (308). In other variations, the sealant layer (312) may be configured to attach to the inner region (308) rather than the upper surface (318) of the outer layer (320) of the protective layer (302), or to both the inner region (308) and the outer layer (320). The outer layer (320) and/or inner layer (310) may be uniformly thick, or may have regions of different thicknesses, i.e., the inner layer may be thicker or thinner than the outer layer. In the example depicted in FIG. 3A, the inner layer (310) is recessed from the upper surface (318) of the outer layer (320), but in other examples the inner layer may protrude or may be in continuity with the upper surface (318) of the outer layer (320). The thickness of the protective layer (302), the inner layer (310), and adhesive properties may depend on a number of factors, for example, the size of the wound and the condition of the peri-wound skin.

FIG. 3B depicts an anterior perspective view of the dressing (300) with the sealant layer (312) positioned over the protective layer (302) for attachment. As stated previously, the sealant layer (312) may be shaped and sized with an adhesive edge that is greater in size and shape to the size and shape of the inner layer (310). This configuration permits the sealant layer (312) to seal to the upper surface (318) of the protective layer (302), and to provide fluid communication with the opening (306) of the inner layer (310). In other variations, the sealant layer may be configured to seal against the inner layer or a combination of the inner layer and outer layer. The port (314) may be positioned at any suitable location on the sealant layer, and may be configured to rotate with respect to the sealant layer (312). Both the tubing (316) and the port (314) may have a low profile which may help to reduce any pressure points to the sacral region when the patient is in a sitting or prone position. Additional description of ports and tubing that may be used with a dressing for RPWT may be found in pending application Ser. No. 12/626, 426, filed on Nov. 25, 2009, which has been previously incorporated by reference in its entirety.

While the protective layer (302), its inner layer (308), and the sealant layer (312) illustrated in FIGS. 3A and 3B are generally rectangular, any shape that be used for each of the structures. For example, the protective layer, inner layer, and/ or sealant layer may be generally triangular, elliptical, rounded with two or more indentations, and the like. Some variations of the protective layer, the transparent inner layer, and the sealant layer may also have slits or pre-formed creases to help accommodate the different contours of the sacral region.

Figure 3C:
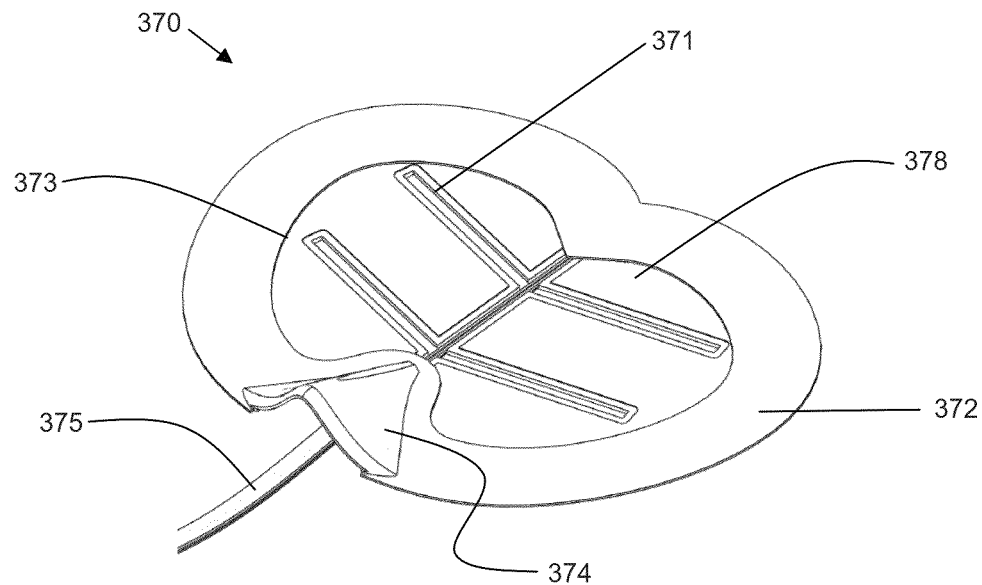
FIG. 3C is an anterior perspective view of another example of a multilayer dressing system with a rounded bi-lobular geometry.
Figure 3D:
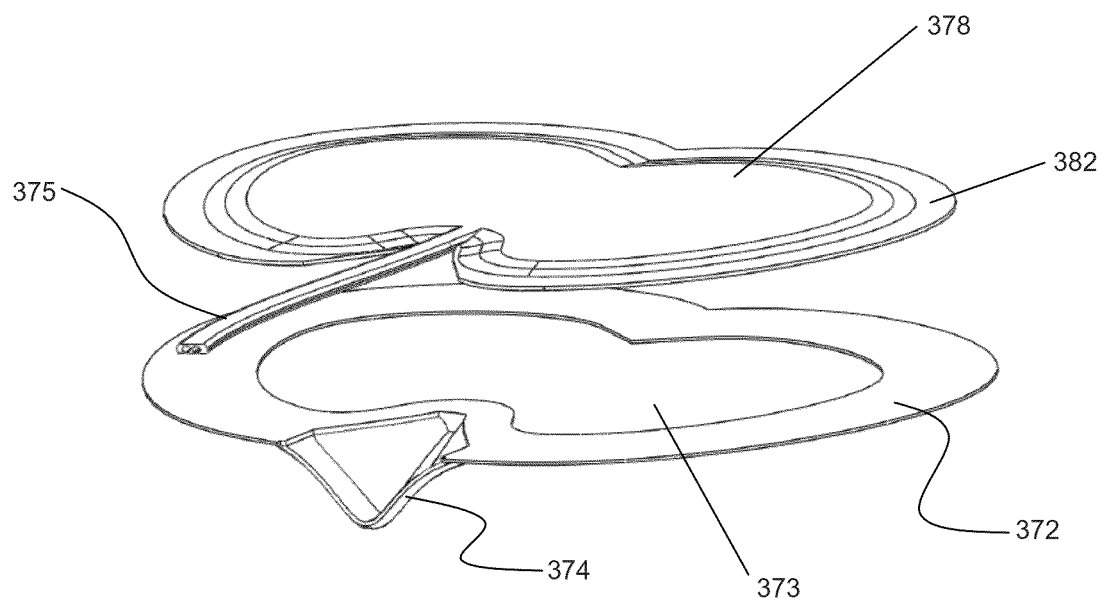
FIG. 3D is a posterior perspective component view of the dressing system in FIG. 3C.

In another example, the RPWT dressing (370) may comprise a rounded configuration with two opposing indentations, e.g., apple-shaped, as shown in FIGS. 3C and 3D. The dressing (370) may comprise a protective layer (372) configured on its lower surface to adhere to the skin and to seal to the sealant layer (382) on its upper surface. The protective layer (372) may comprise a fold-sealing region (374) along one outer edge and a central opening (373) or an optional inner layer in place of the central opening. The fold-sealing region (374) may have an open cavity or recess that permits passage of tubing (375) of the sealant layer (382) through it when the sealant layer (382) is attached. The anterior surface of the recess and/or the tubing (375) may comprise an adhesive to further secure the tubing (375) to the recess. In other examples, adhesive tape may be applied to the tubing and the recess after the sealant layer is attached to the protective layer. The sealant layer (382) may comprise a peripheral region (391) and an inner layer (378), with a conduit system (371) in fluid communication with the tubing (375) and a wound bed. In this particular example, the conduit system (371) comprises a branched conduit system with open grooves or recesses. Other variations of conduit systems are described later.

Figure 3E:
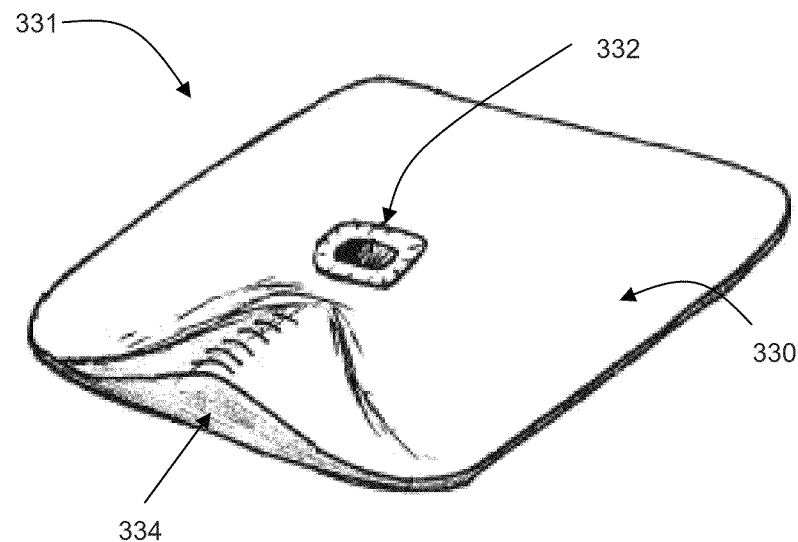
FIGS. 3E and 3F are anterior and posterior perspective views of a variation of a dressing system with low-profile tubing.
Figure 3F:
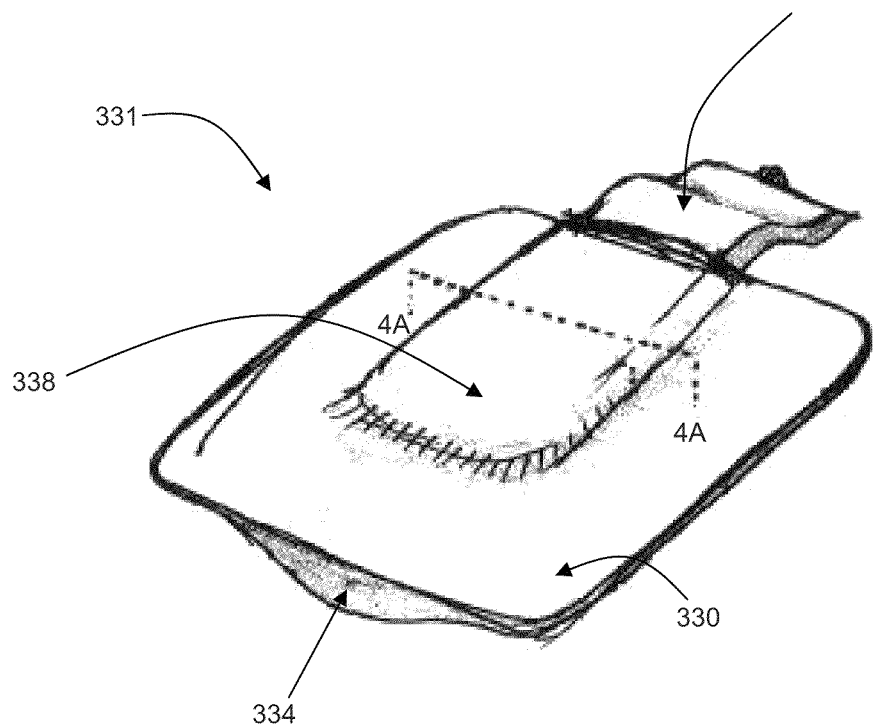

While some of the dressing systems described above comprise multiple separate layers, other dressing may have a unibody or monolithic configuration. One variation of a unibody dressing (331) is shown in FIGS. 3E and 3F. As depicted in FIG. 3E, the dressing (331) may comprise a generally planar cover (330) that has an opening (332) and a fold-sealing region (334). The fold-sealing region (334) may be deformable or moldable (e.g. a moldable polymer or foam), so that its size and shape may be modified to form an airtight seal with the skin of the intergluteal cleft. The opening (332) provides communication between a wound bed and tubing (336) via a dressing port (338). The dressing port (338) and tubing (336) are shown on the other side of the sheet (330) in FIG. 3F. This configuration permits reduced pressure to be applied to the wound bed via the tubing (336) and dressing port (338). In some variations, the port, tubing, and other devices may be embedded in or integral with the dressing.

The dressing layers described above, e.g., the protective layer, the transparent region, the sealant layer, occlusive cover, etc., may be made of any elastic or flexible materials that allow the dressing to form a seal with various anatomical contours of the sacral region. The protective layer, the transparent region, and the sealant layers may each comprise any variety of materials, including but not limited to polyurethane, silicone, vinyl, polyvinyl chloride, polyisoprene, latex, rubber, thermoplastic elastomers, hydrogels, hydrocolloids, and the like. The materials may also have a solid, lattice, open-cell foam, closed-cell foam or matrix configuration, for example.

Figure 4A:
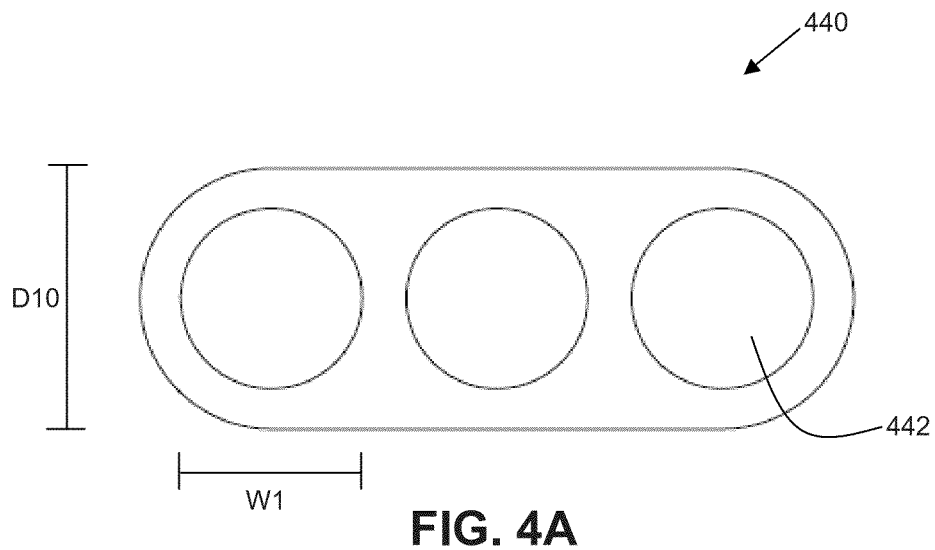
FIGS. 4A-4C are exemplary cross-sectional views various low-profile tubing configurations that may be used with a dressing system.
Figure 4B:
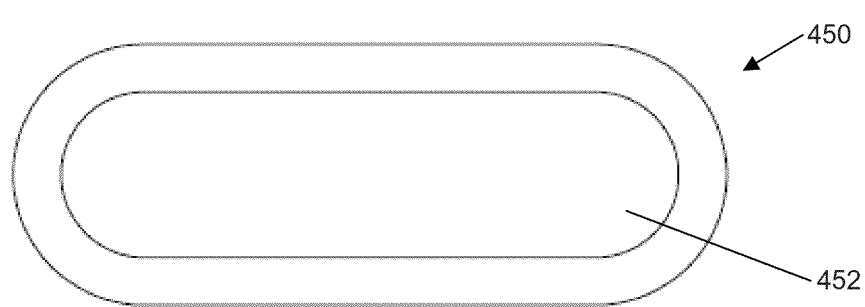
Figure 4C:
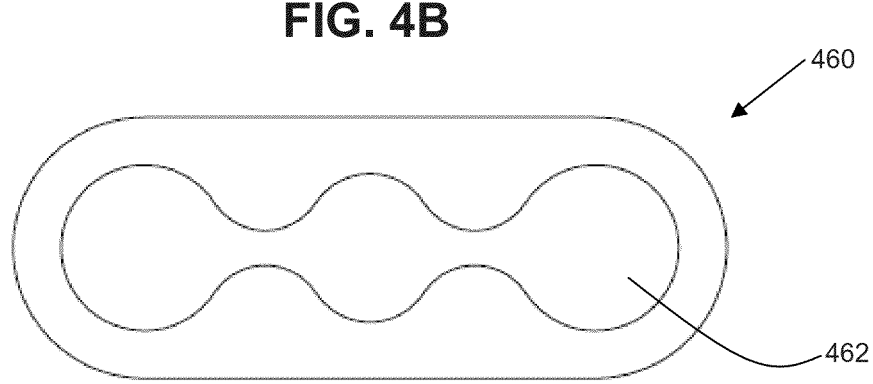

The tubing used with the dressings described above may be configured to reduce the possibility of further pressure-induced tissue necrosis due to load-bearing of these elements against the patient's body. For example, the tubing and the conduits therein may have a wider and lower profile relative to the skin or wound surface than similar traditional circular RPWT conduits, serving to reduce adverse loading to the body surface when the tubing is located in a weight-bearing position, e.g., when the patient is in a sitting or prone position. For example, low-profile luminal cross-sections of the tubing may be oblong, such that the tubing is wider than it is deep. Examples of different configurations of low-profile tubing may be viewed by taking a luminal cross-section along the line 4A-4A in FIG. 3G. FIGS. 4A-4C depicts some examples of low-profile conduit configurations that may be used for applying reduced pressure to wounds in the sacral region. In general, the conduits may have a flat profile to distribute loading and reduce pressure points on the skin of the sacral region. For example, the depth (D10) of a conduit may be less than or equal to the width (W1) of the conduit in cross-section. The depth (D10) of a conduit may be from about 2 millimeters to about 5 millimeters, for example, from about 1 millimeter to about 3.5 millimeters, or from about 3 millimeters to about 5 millimeters. As shown in FIG. 4A, tubing (440) may have multiple longitudinal conduits (442), where the adjacent conduits are arranged side by side. This arrangement may help to ensure that reduced pressure is maintained at the wound bed in the event one of the conduits becomes occluded (e.g., occluded with fluid build-up, tissue matter, etc.). In another variation shown in FIG. 4B, tubing (450) may have a single conduit (452) that is shaped according to the flattened profile of the tubing (450), e.g., elliptical shaped. In yet another variation depicted in FIG. 4C, tubing (460) may have a single conduit (362) that has rounded and tapered portions.

Figure 5A:
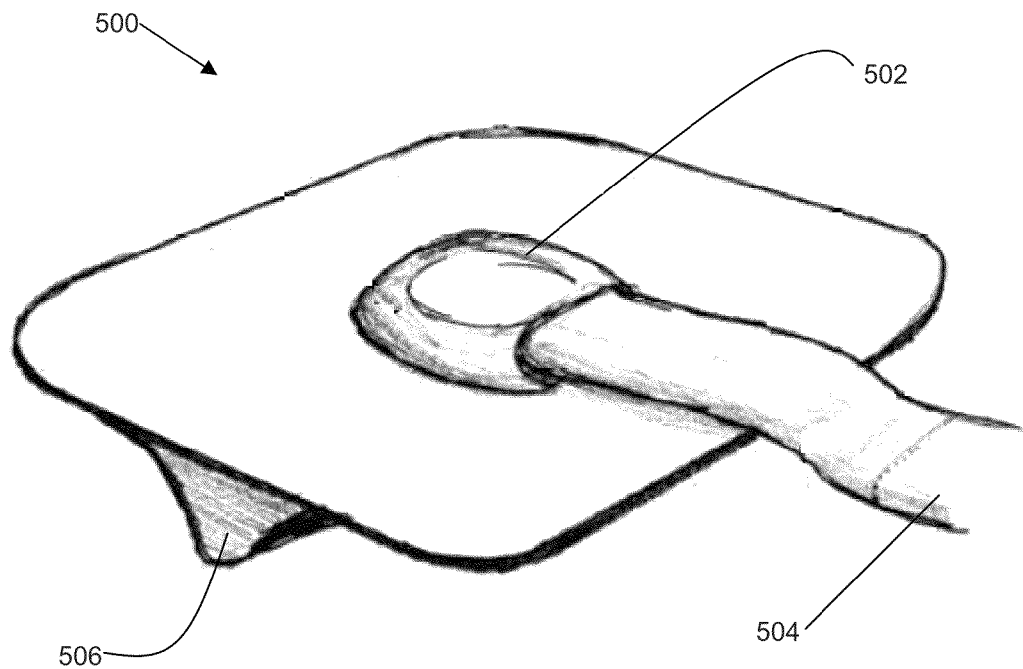
FIGS. 5A-5C depict various dressing port configurations that may be used with a dressing system.

FIG. 5A depicts a variation of a dressing (500) comprising a low-profile port (502) attached on the outer surface of the dressing, tubing (504) connected to the port (502), and a fold-sealing region (506) configured to form an airtight seal with the skin in the intergluteal cleft. The width of the port (502) is preferably a multiple of the height of the port, e.g., at least about 2 times greater than the height of the port (502), and in other examples may be as much as 3 times, 4 times, or 5 times or more greater than the height. The tubing (504) extends away from the dressing (500) across an edge of the dressing that is perpendicular to the edge that has the fold-sealing region (506), or laterally when applied to the patient. In other examples, the tubing may be oriented on the opposite edge or same edge as the fold-sealing region (506). Indeed, the tubing may have any angular orientation from about 0 degrees to about 359 degrees relative to the center of the fold-sealing region (506), and/or comprise a relative position that is generally parallel but laterally offset to the superior/inferior orientation of the fold-sealing region (506).

Figure 5B:
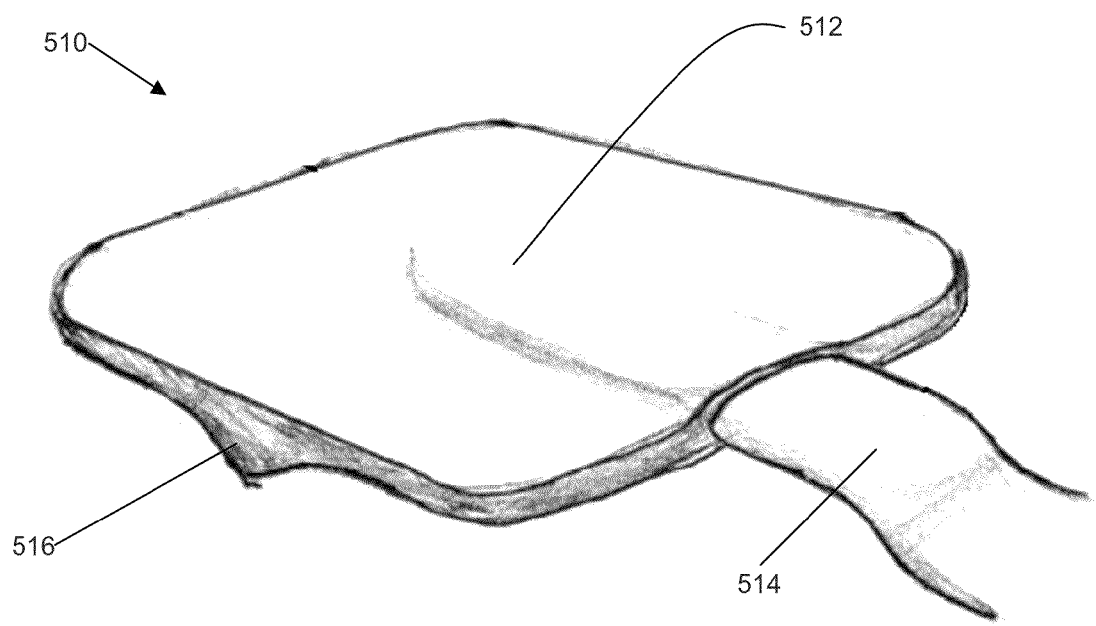

FIG. 5B depicts another variation of a dressing (510) comprising a port (512) that is embedded within the dressing, embedded tubing (514) that is connected to the port (512) within the dressing, and a fold-sealing region (516). As seen in this variation, the port (512) and the tubing (514) may be directly integrated into the dressing itself, or may be embedded beneath the surface of the dressing. In certain variations of a dressing for RPWT of the sacral region, the tubing may be embedded in a gel-filled or otherwise soft material support. The material support may be substantially wider than the tubing. These configurations may lower the profile of the dressing by reducing any protrusions above the dressing surface, which may help reduce tissue pressure when a patient's weight is placed over the tubing. The tubing (514) extends away from the dressing (510) along an edge that does not have the fold-sealing region (516).

Figure 5C:
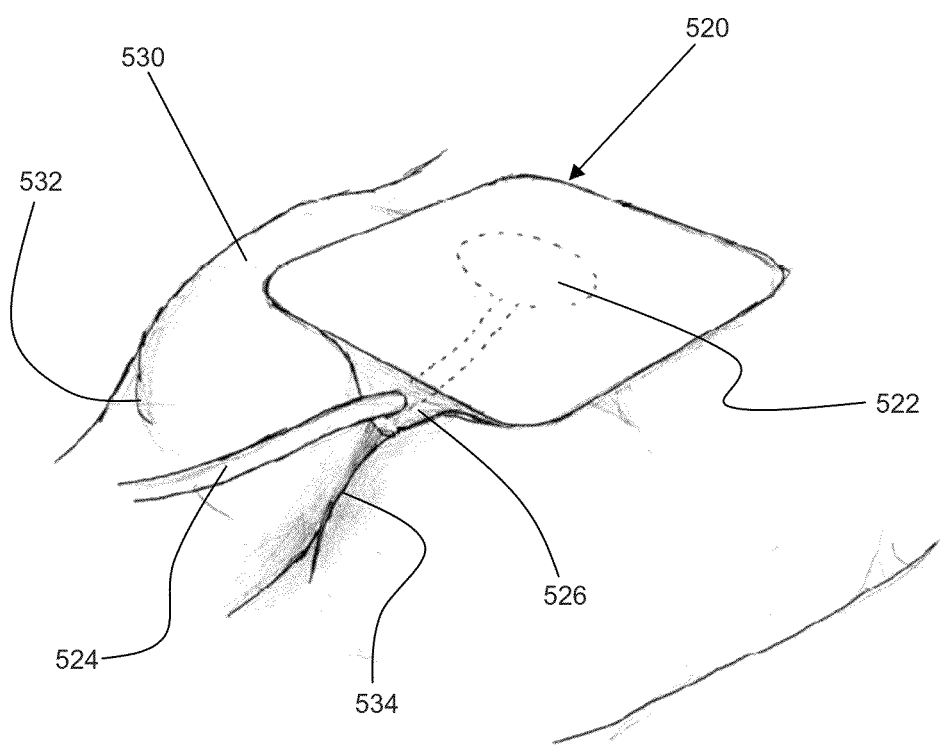

In some variations, the tubing may extend away from the dressing along or within the fold-sealing region. An example of a dressing (520) where the tubing (524) extends from the dressing through the fold-sealing region (526) is shown in FIG. 5C. The port (522) and the tubing (524) may be embedded within the dressing (520). Once the tubing (524) exits the dressing (520) via the fold-sealing region (526), it may extend through the intergluteal cleft (534), between the gluteal regions (530), and may curve along the gluteal crease (532). Threading the tubing (524) along these anatomical contours may help to reduce localized pressure points that may be introduced by the dressing, and may reduce the patient loading on the tubing, which may help promote sufficient air flow to the wound bed for RPWT.

Figure 6C:
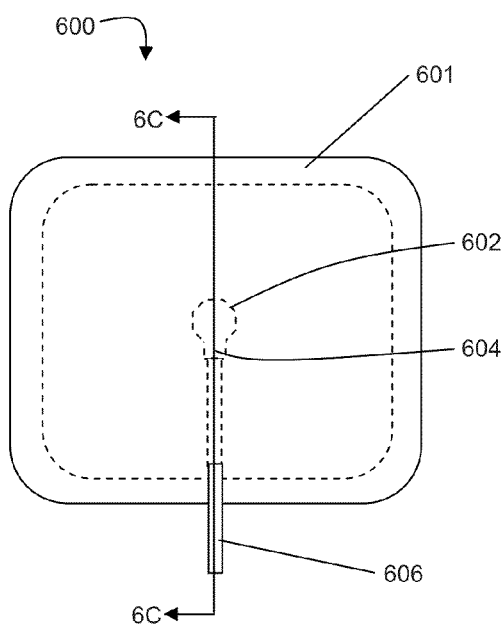
FIG. 6C is a schematic cross-sectional view of the dressing system of FIGS. 6A and 6B being applied to a treatment site.
Figure 6C:
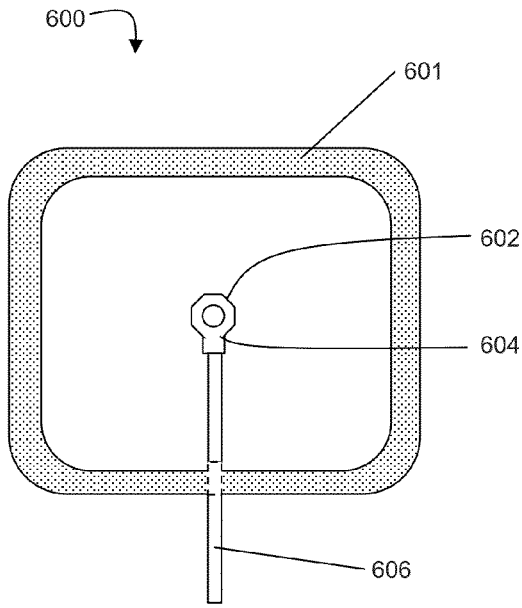
Figure 6C:
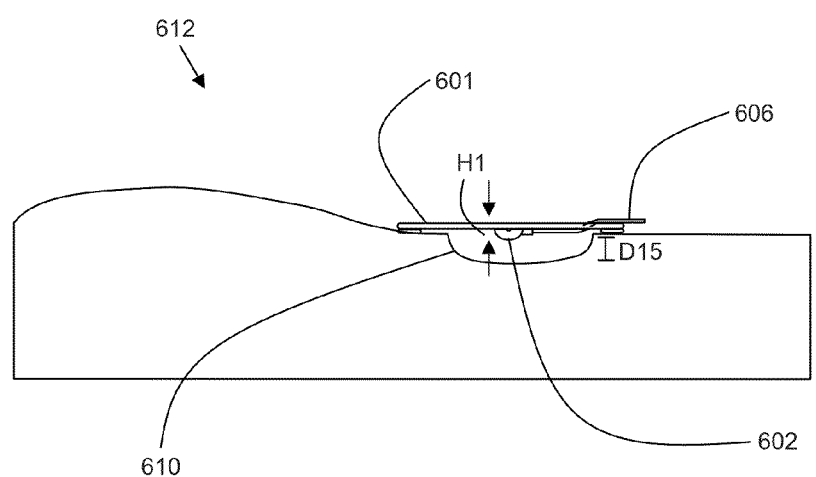

Another variation of a dressing that is configured to reduce pressure points in the sacral region due to dressing ports and tubing is shown in FIGS. 6A-6C. Dressing (600) comprises a base layer (601) with an opening (604) that provides access to a wound bed (610) for tubing (606) via a port (602). FIG. 6A depicts a top view of the dressing (600), which shows that the tubing (606) may be partially embedded in the dressing. FIG. 6B depicts an underside, i.e., the tissue-contacting side, of the dressing (600), which shows that the port (602) may be located on the surface of the tissue-contacting side. FIG. 6C show a cross-section of the dressing (600) as it is applied to the sacral region (612) of a patient. As shown there, the depth (D15) of the wound bed is greater than the height (H1) of the port (602), so that port (602) may not directly contact the wound bed (610). Positioning the port (602) within the enclosure of the wound bed (610) may also allow for the infusion of therapeutic agents to the wound bed (610) via the tubing (606).

Figure 7A:
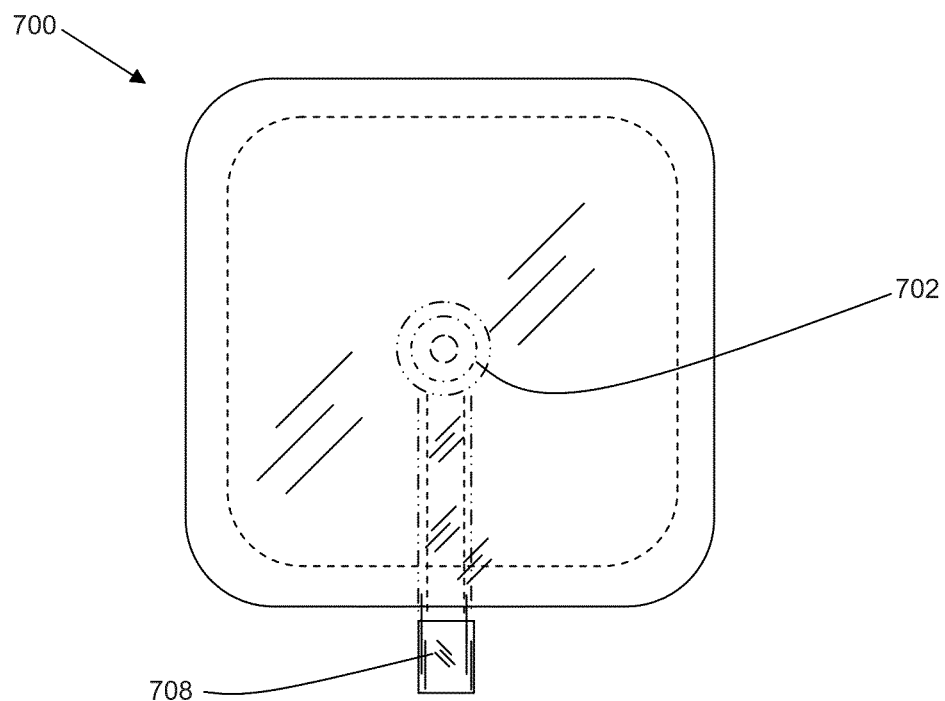
FIG. 7A is a posterior view of another variation of dressing comprising tubing integrated into the dressing layer.
Figure 7B:
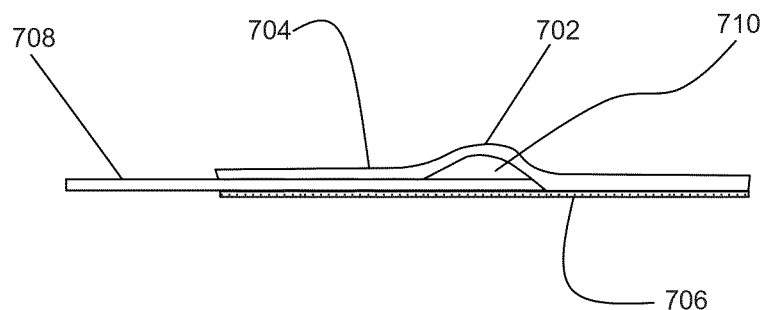
FIG. 7B is a cross-sectional view of the dressing in FIG. 7A.

FIGS. 7A and 7B depict another variation of a dressing (700) with a port (702) that is molded from a top layer (708) of the dressing (700). The port (702) may be molded from the top layer (708) such that it protrudes from the generally planer surface of the dressing (700). The port (702) may be in fluid connection to tubing (708), which may be any low-profile tubing as previously described. As shown in cross-section in FIG. 7B, the bottom layer (706) of the dressing (700) may have an opening (710) that may be positioned over a wound for RPWT. Molding the port (702) from a layer of the dressing (700) may help to ensure an airtight connection to the dressing, and may reduce air leakage as compared to ports that are separately formed and later joined to the dressing. In some variations, a support frame or other structure may be provided in the port or on a surface of the port to maintain its shape.

Figure 8A:
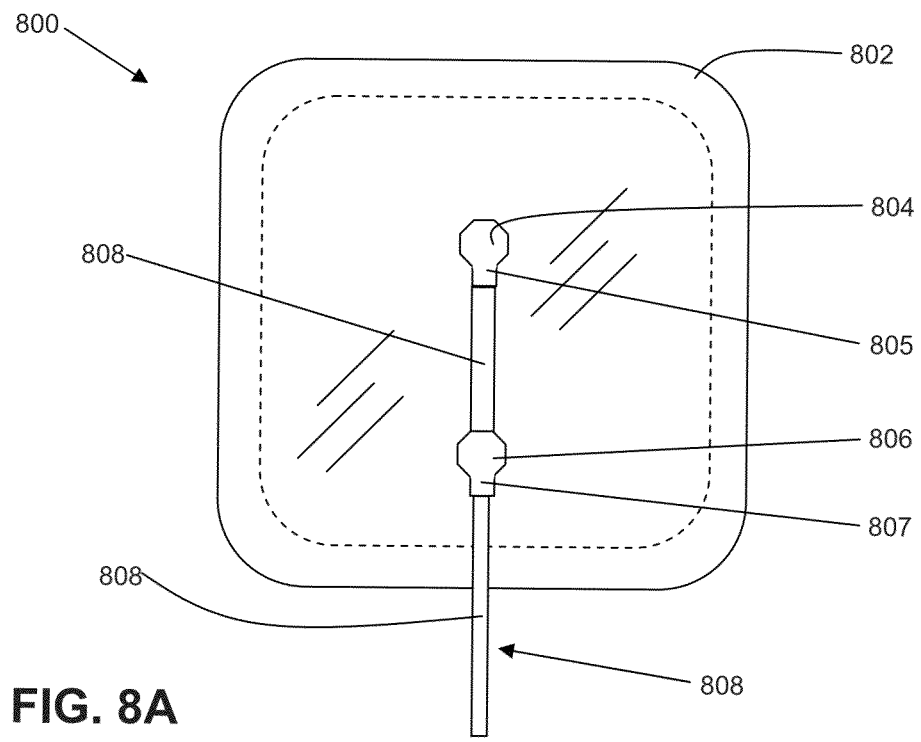
FIGS. 8A and 8B depict a variation of a dressing system comprising multiple ports.
Figure 8B:
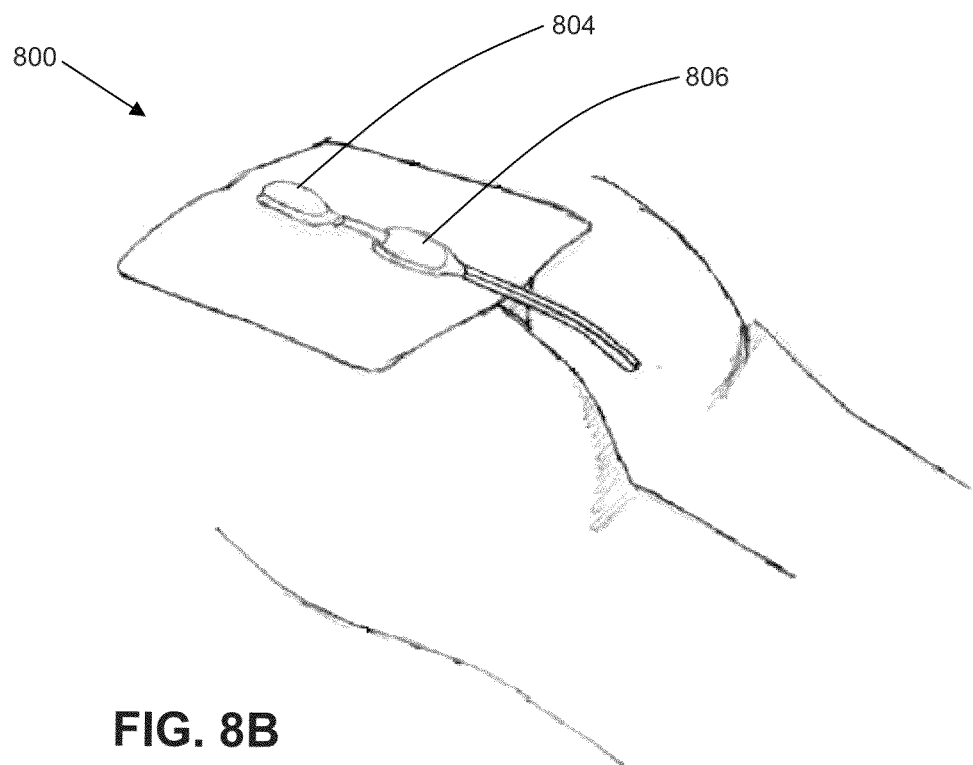

While dressings for RPWT of the sacral region may comprise one port and one opening for accessing a wound bed, other suitable dressings may have a plurality of ports and openings through with RPWT may be applied to a sacral wound. Multiple ports may be provided to provide RPWT to multiple sacral wounds, or may provide a level of redundancy to ensure that the wound bed continues to receive treatment in the event one pressure source is occluded. There may be 2, 3, 4, 5, 6, 7, 8, 9, or more etc. ports provided in the dressing to treat one or more wounds. Examples of dressings with multiple ports are shown in FIGS. 8A and 8B. Dressing (800) may comprise a base layer (802) with a first opening (805) connected to a first port (804), and a second opening (807) connected to a second port (806). The first and second ports may be connected to a single tube that passes through the second port and terminates at the first port, or by separate tubes. In other variations, the first and second ports may be separately connected to one or more vacuum sources. In some variations, the dimensions of the tubing may vary to help distribute the applied pressure across the one or more ports. For example, a first tubing segment (810) may be wider than a second tubing segment (811) to help ensure that the pressure applied at the first port (804) is generally similar to the pressure applied at the second port (806). FIG. 8B depicts how the dressing (800) may be applied to the sacral region of a patient. The first port (804) and the second port (806) may be any of the ports as previously described, and both ports and the tubing (808) may be low profile to reduce pressure points in the sacral region. Additional description of low-profile tubing and ports, as well as the assembly of low-profile dressings may be found in pending application Ser. No. 12/626,426, filed on Nov. 25, 2009, which has been previously incorporated by reference in its entirety.

Figure 9:
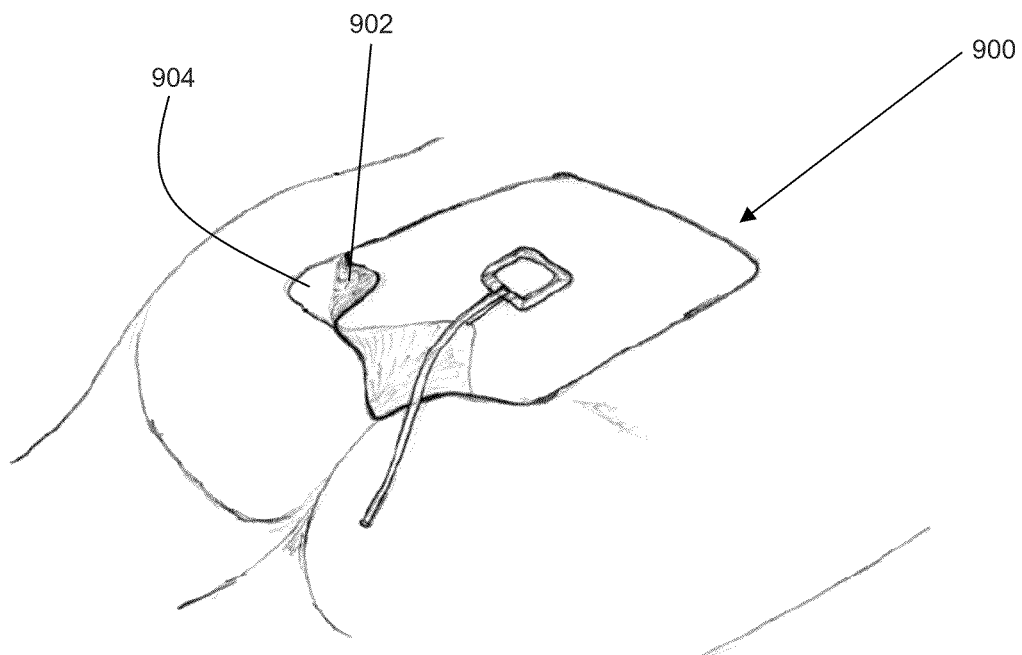
FIG. 9 depicts one variation of a dressing system comprising multiple peel-away layers.

As described above, a dressing for RPWT may form an airtight seal at the surface of the skin by using one or more adhesives. In examples where an adhesive with a high bond-strength is used to create an airtight seal with the skin surface, it may be desirable to provide a clean dressing without having to replace the dressing, which may cause damage to the peri-wound skin. On the other hand, prolonged attachment of a dressing to a sacral region may lead to moisture accumulation (e.g., sweat, urine, interstitial fluid, etc.) and the possible accumulation of fecal matter, which may damage skin not covered by the dressing. In one variation, shown in FIG. 9, the dressing (900) has one or more layers that may be peeled off as the top layer is dirtied. For example, once the top layer (902) is dirtied, it may be peeled away to reveal a dressing layer (904) that is under the top layer. Since the dressing layer (904) has been occluded from moisture and fecal exposure by the top layer (902), removing the top layer may restore the cleanliness and sterility of the sacral dressing (900). In other variations, the surface of the dressing may be amenable to rinsing during normal body cleansing in the sacral area.

Figure 11:
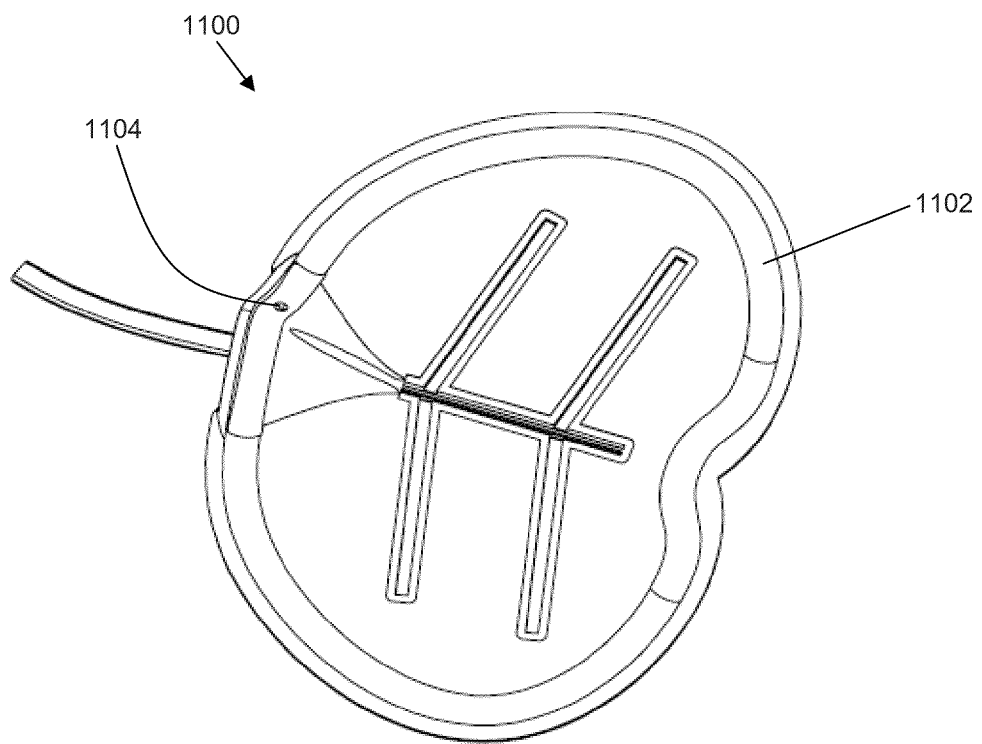
FIG. 11 shows another variation of a dressing configured for use with an injectable adhesive.

In some variations, instead of a dressing with a pre-configured adhesive layer, the adhesive between the dressing and the skin of the sacral region may be injected, as shown in FIGS. 10A-10C. This may permit, for example, positioning and repositioning of a dressing before finally adhering the dressing to the patient. Dressing (1000) may comprise a base layer (1002) with an adhesive channel (1004) along the perimeter of the dressing, where the adhesive channel (1004) is in fluid communication with an adhesive port (1006) and contacts the skin surface. The adhesive channel (1004) may comprise a porous surface that permits controlled leakage of an injected adhesive out of the channel (1004) and adhere to the skin. The dressing (1000) may have any size and shape as described above, and may have a narrow sealing region (1008) to accommodate anatomical contours of the sacral region, e.g., the tail bone. The adhesive channel (1004) may substantially follow the perimeter of the base layer (1002), or may enclose an area that is smaller than the area of the base layer (1002). For example, the adhesive channel (1004) may be adjusted to outline the perimeter of the sacral wound. The adhesive port (1006) may also comprise a valve mechanism, e.g., a one-way valve, and may be configured to interface with standard syringe and/or tubing connectors. Another variation of a dressing (1020) with a rectangular geometry is shown in FIGS. 10B and 10C. The dressing (1020) comprises a base layer (1022) with an adhesive channel (1024) that is connected to an adhesive port (1026). FIG. 11 depicts a dressing (1100) comprising an adhesive conduit (1102) and adhesive port (1104) that has a rounded, elliptical shape. Examples of injectable adhesives include cyanoacrylates, silicone, silicone gels, hydrocolloid, hydrogel, urethanes and other liquid adhesives.

Figure 12A:
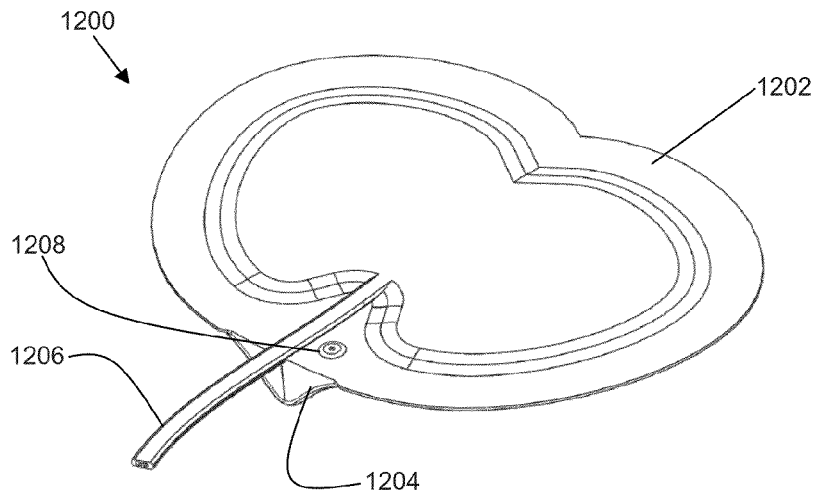
FIGS. 12A and 12B are posterior and anterior perspective views of a dressing, respectively, comprising a fillable fold-sealing region and configurable conduit system in a fully opened state.
Figure 12B:
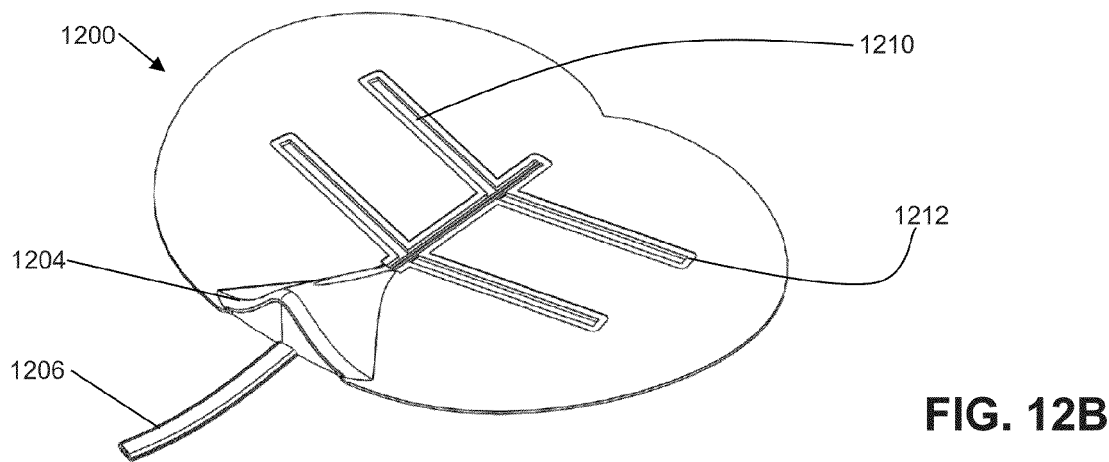
Figure 12C:
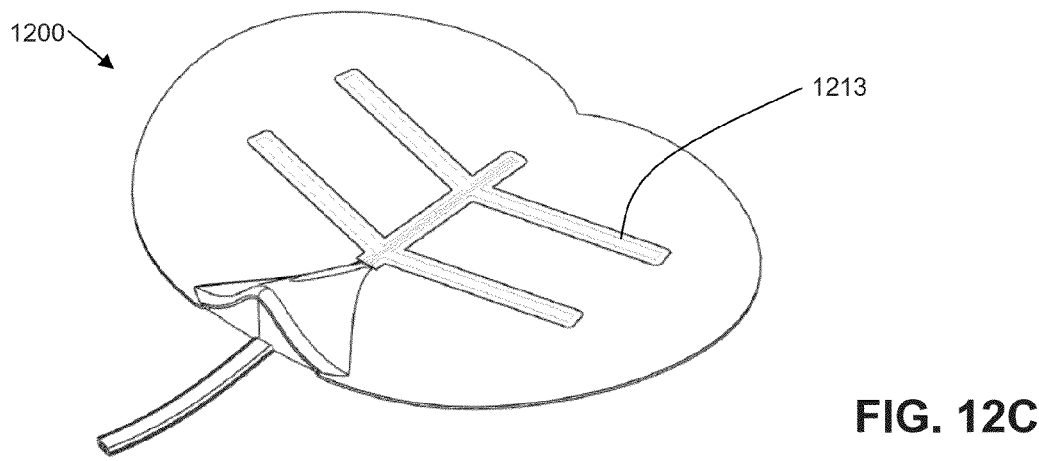
FIG. 12C depicts the dressing of FIG. 12B with the configurable conduit system in a pre-configured state.

One variation of a dressing (1200) is shown in FIGS. 12A-12C. The dressing (1200) comprises a sealant layer (1202) with a rounded geometry, that may be characterized as two intersecting elliptical lobes, with indentations at their intersection, as depicted from a top perspective view in FIG. 12A. The dressing (1200) may also have a fold-sealing region (1204), where the size and shape of the fold-sealing region (1204) may be adjusted by injecting a fluid through an inflation port (1208). A tubing (1206) may be partially embedded into the dressing (1200) to provide a channel between a reduced pressure source and a wound bed. The tubing (1206) of the dressing (1200) in FIGS. 12A-12C extends away from the dressing via the inflatable fold-sealing region (1204), and may be partially or wholly embedded in the fold-sealing region. For example, the fold-sealing region may be filled with a gel or other similarly compliant material, with the tubing embedded therein to provide a low-profile dressing. FIG. 12B illustrates the underside of the dressing (1200), e.g., the tissue-contacting side. In this variation, the dressing (1200) also comprises an arrangement of conduits (1210) that may be connected to a reduced pressure source via the tubing (1206) to provide reduced pressure to a wound site. The conduits (1210) depicted in FIG. 12B comprise an open configuration, i.e., the conduits (1210) have an open geometry along their longitudinal length such that the interior surface of the conduits are exposed. In other examples, depicted in FIG. 12C, the conduits (1210) may comprise a removable or trimmable occlusion structure (1213) there within, that may be used to selectively open or expose portions of the conduit (1210), and may be used to customize the conduit pathways in communication with the tubing (1206). The occlusion structure (1213) may comprise, for example, a fitted elongate silicone or polymeric member that may be removably inserted or provided within the conduit (1210) or a selectively removable adhesive layer. The occlusion structure may comprise a unibody design, or may be segmented at preselected locations to facilitate certain conduit configurations (e.g. at branch points of the conduit). In other examples, occlusive tape may be applied to seal off portions of the conduit where a vacuum pathway is not desired. These configurations may allow for the treatment of off-center wounds relative to body planes and treatment of multiple wounds with the same dressing.

Figure 13A:
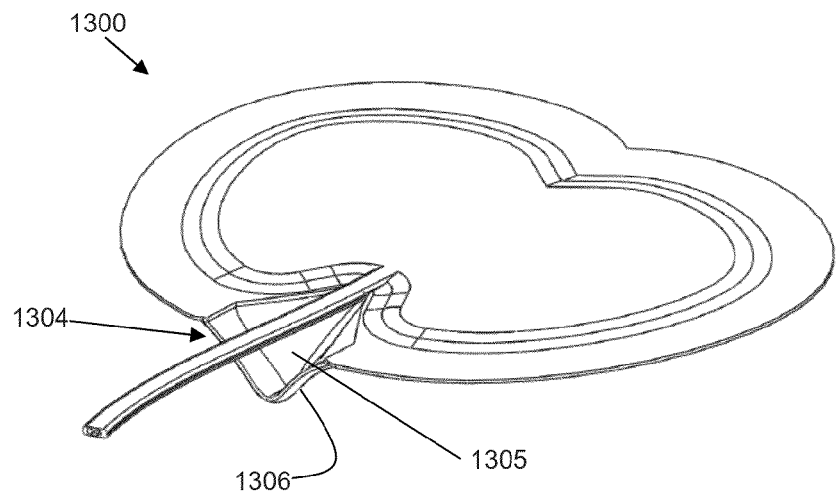
FIGS. 13A and 13B are posterior and anterior perspective views of another dressing comprising a configurable conduit system in a fully opened state.
Figure 13B:
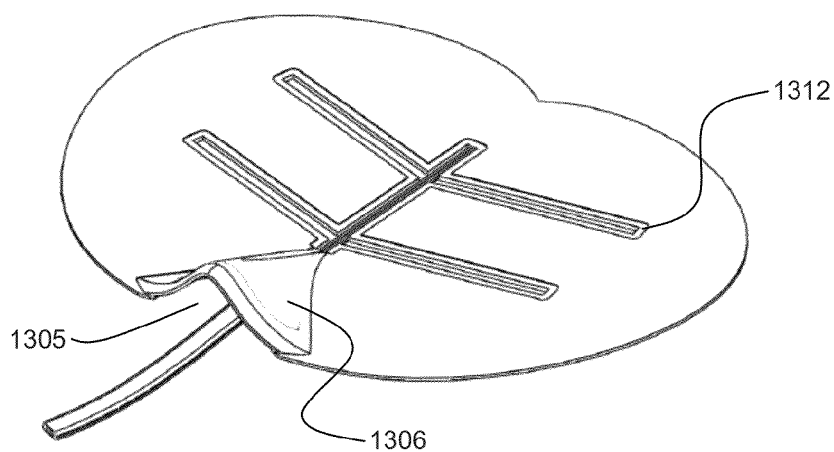
Figure 13C:
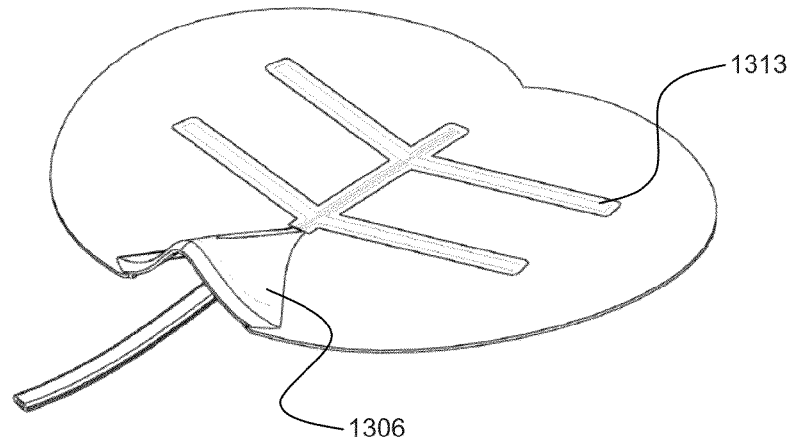
FIG. 13C depicts the dressing of FIG. 13B with the configurable conduit system in a pre-configured state.

In another variation, a dressing (1300) shown in FIGS. 13A-13C comprises a fold-sealing region (1304) that comprises an open or exposed recess or cavity (1305), as depicted along the inferior and anterior surfaces of FIGS. 13A-13C. In some variations, this may allow the user to press an adhesive surface (1306) of the fold-sealing region (1304) onto the skin of an intergluteal cleft. The adhesive surface (1306) may be pressed onto the skin to form an airtight seal by running a finger along the surface of the fold-sealing region (1304) to contact the intergluteal skin. In other variations, the dressing may be provided with a suture within the volume (1305), which may be tensioned and pressed such that the length of the tensioned suture is drawn along the surface of the dressing contacting the skin of the intergluteal cleft. This may help to smooth the adhesive surface (1306) against the skin. FIGS. 13B and 13C also depict how adhesive regions (1312) may be occluded by a support element (1313), which may be removed prior to applying the dressing to the sacral region.

Figure 14:
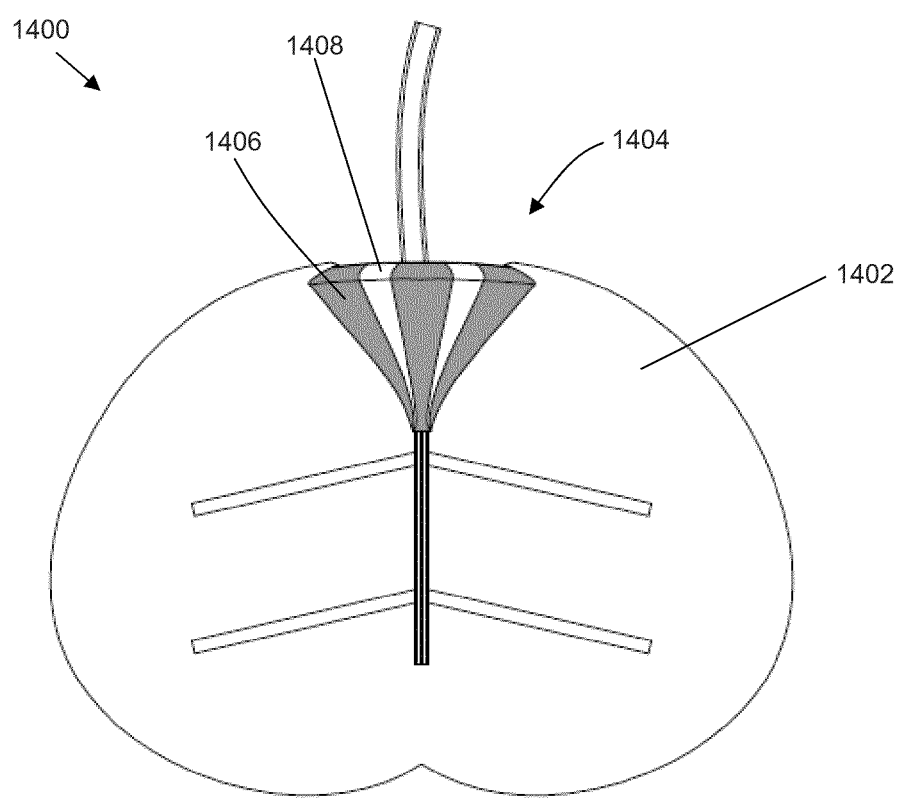
FIG. 14 illustrates an anterior view of a dressing system with a fold-sealing region comprising multiple elastic regions.

Another variation of a dressing for RPWT of the sacral region is illustrated in FIG. 14. As shown there, the dressing (1400) may comprise a base layer (1402) that is shaped as two intersecting ellipses, as well as a fold-sealing region (1404) that may have a first elastic region (1406) and a second elastic region (1408), as previously described. The elasticity of the first elastic region (1406) may be different from the second elastic region (1408), and the elastic properties of these two regions (1406) and (1408) may be different than the base layer (1402). In other variations, the fold-sealing region may comprise a single triangular or tapered elastic region. Fold-sealing regions with portions of different elastic characteristics may help the dressing to form a substantially airtight bond with the skin in the intergluteal cleft.

The dressings described above may also be configured with support mechanisms that redistribute contact forces acting on the wound bed and/or peri-wound skin, and may also serve to help maintain the airtight seals of the dressings. For example, a substantially airtight seal around a wound may be maintained by increasing the mechanical forces pushing or acting on the adhesive when the patient sits or lies on the dressing, thereby increasing the seal of the adhesive to the skin. In some variations of dressings for RPWT of the sacral region, a secondary device may be adhered to the skin the sacral region over the wound dressing to help divert any body weight off the dressing, and to the periphery of the wound dressing. Examples of devices that may help redistribute body weight from the dressing to the periphery of the dressing are shown in FIGS. 15A-15C, 16A and 16B, and 17A-17D. These devices may have a raised structure whose border sits outside the wound area, e.g., over the unwounded region. This raised structure may be, for example, inflatable, foam-filled, and/or gel-filled. Such compliant raised structures or protrusions may act to shield the wound bed from additional pressure while helping the dressing to maintain skin contact around the wound when the patient is in a sitting or prone position. The raised structure may have any suitable geometry that substantially surrounds the wound bed.

Figure 15A:
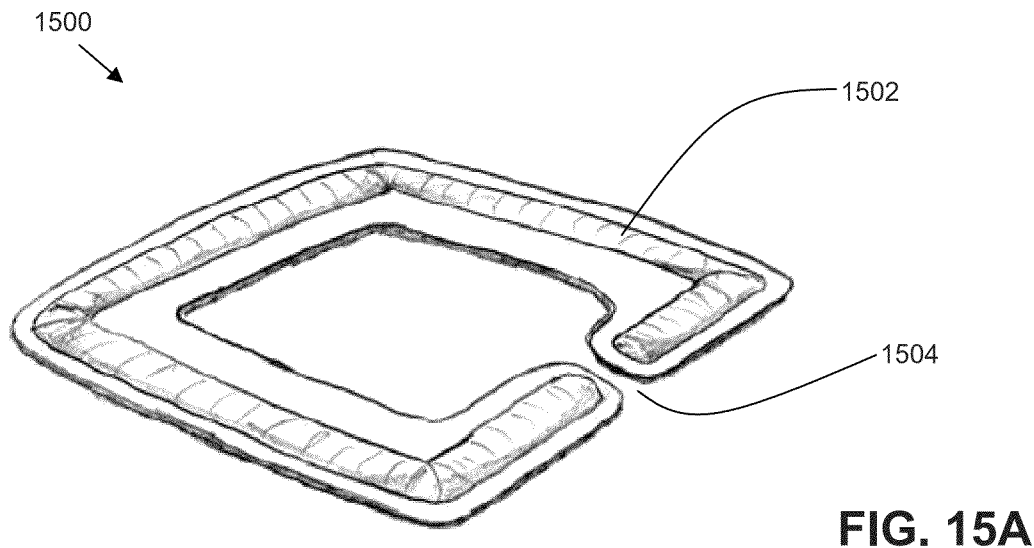
FIG. 15A depicts a posterior perspective view of a cushion device that may be used with the dressing systems described herein.
Figure 15B:
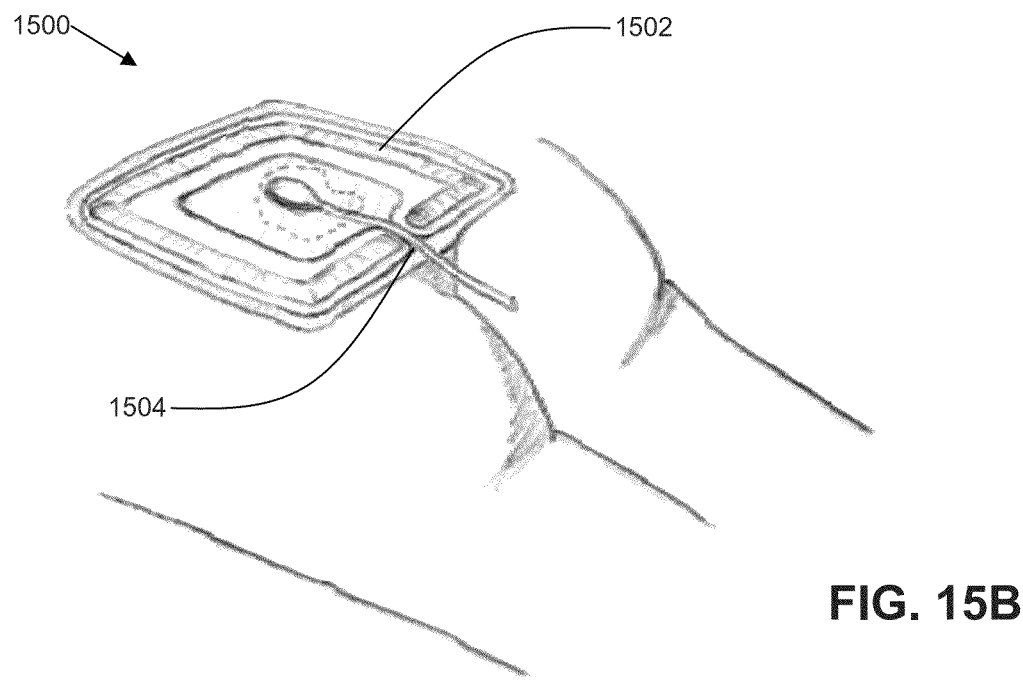
FIG. 15B depicts the cushion device of FIG. 15A used with a dressing on a patient.
Figure 15C:
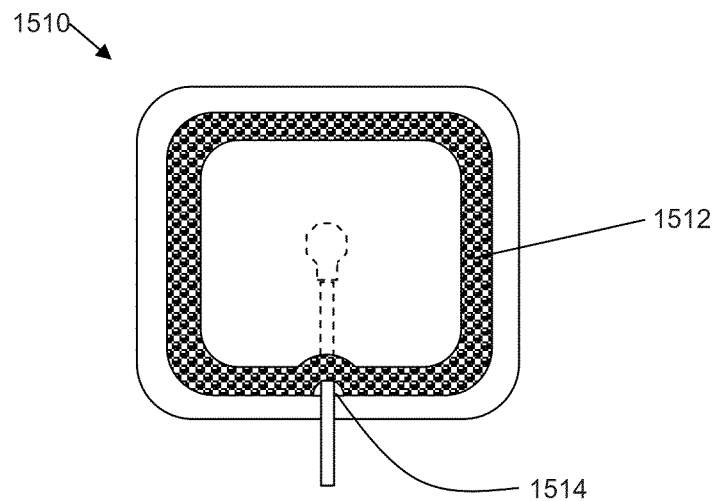
FIG. 15C is a superior view of a dressing system with an integrated cushion.
Figure 15D:
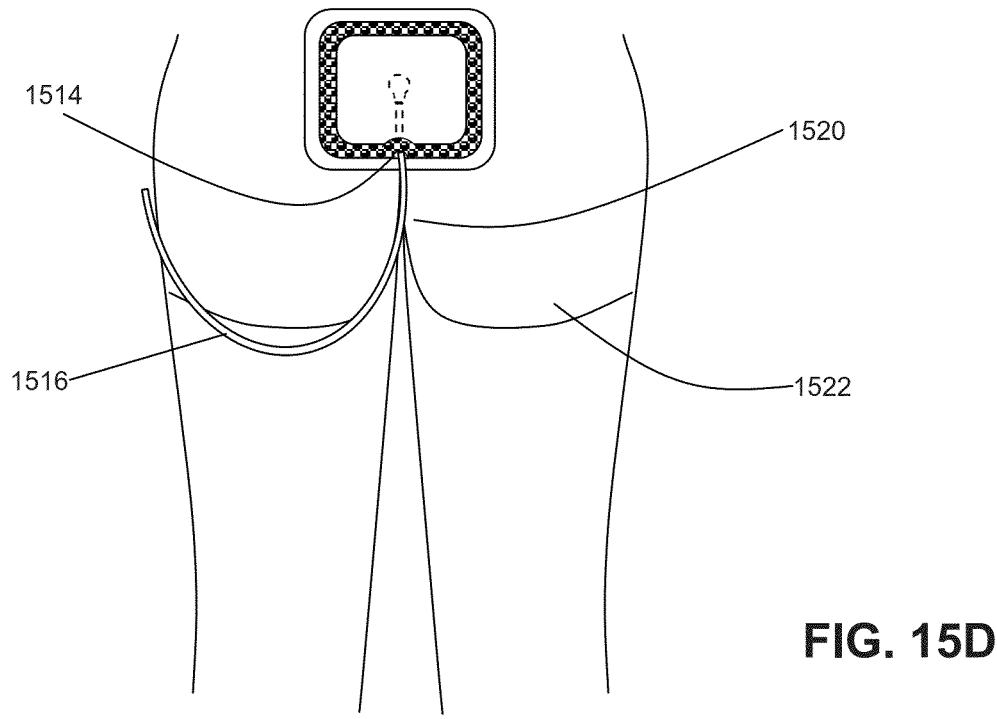
FIG. 15D depicts the use of the dressing system in FIG. 15C on a patient.

FIGS. 15A and 15B depict a supportive device (1500) that may comprise a raised structure (1502) with a rectangular geometry. As shown there, the raised structure (1502) has an opening (1504) that may be configured to allow tubing to pass therethrough. FIG. 15B illustrates one example how supportive device (1500) may be applied on top of a dressing for RPWT of the sacral region, where the tubing extending from the dressing passes through the opening (1504). Alternatively, the raised structure may have a closed-shape, such as in the supportive device (1510) shown in FIGS. 15C and 15D. The raised structure (1512) has a closed geometry, but may comprise an elevated region (1514) that may be suitable for the dressing tubing to pass therethrough. The elevated region (1514) may also be shaped to help guide the tubing in a certain direction. For example, FIG. 15D shows that the tubing (1516) is guided through the elevated region (1514), along the intergluteal cleft (1520), and curving along the gluteal crease (1522). This may help to reduce any pressure points in the sacral region that may arise from the tubing (1516).

Figure 16A:
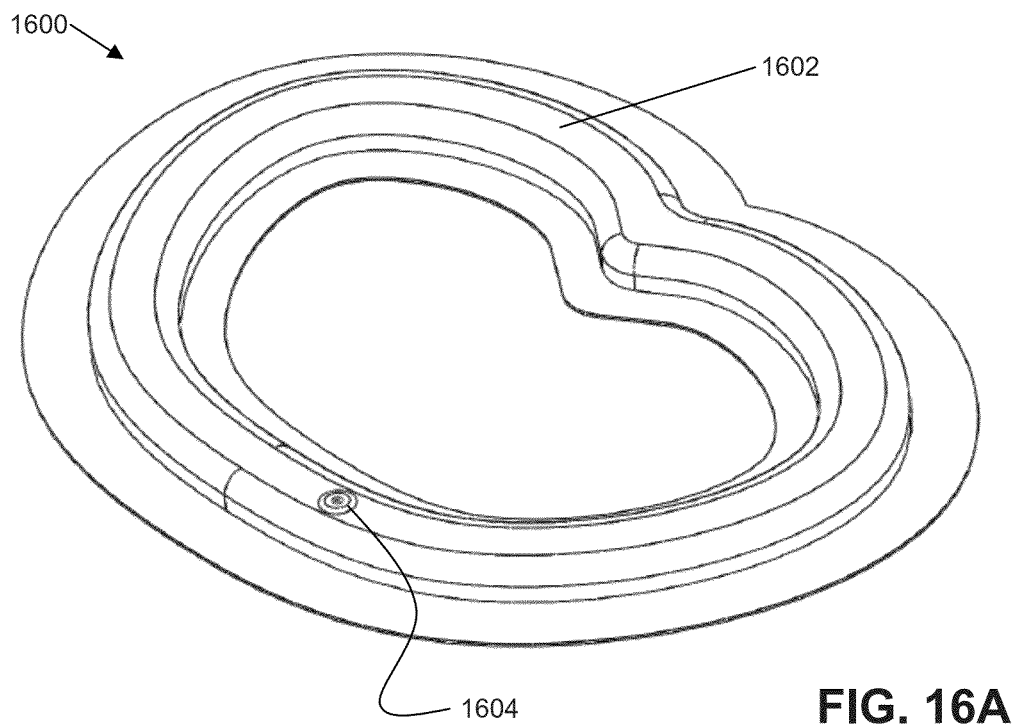
FIGS. 16A and 16B are posterior perspective views depicting additional examples of dressing systems with cushion regions.
Figure 16B:
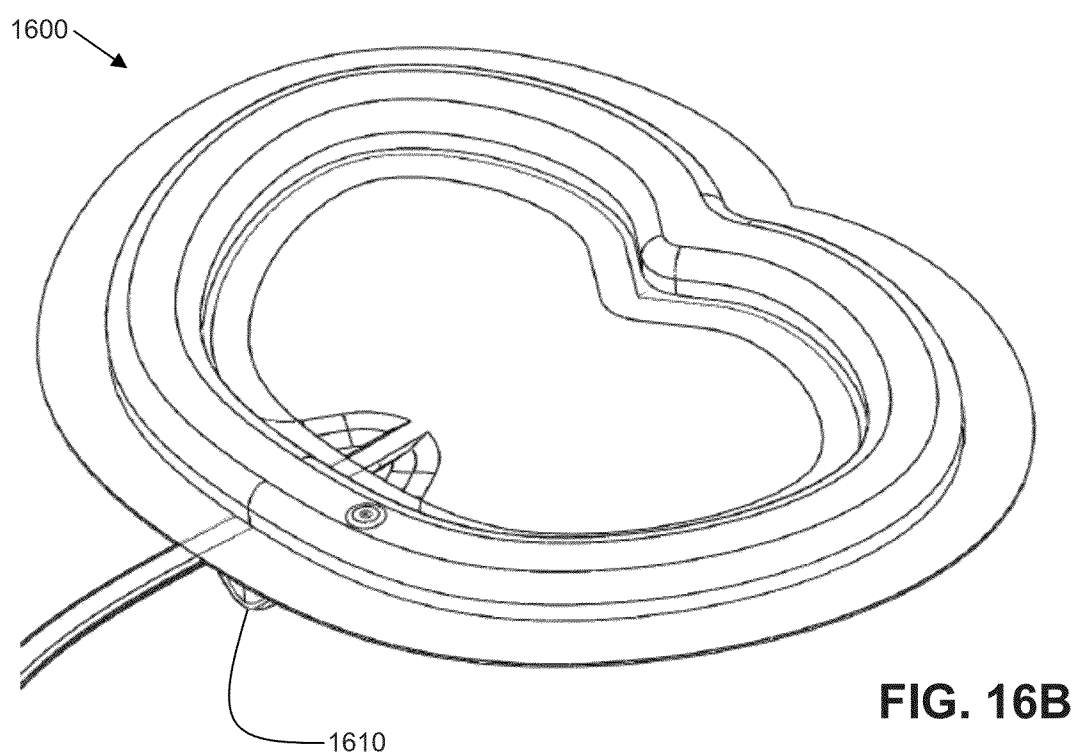
Figure 17A:
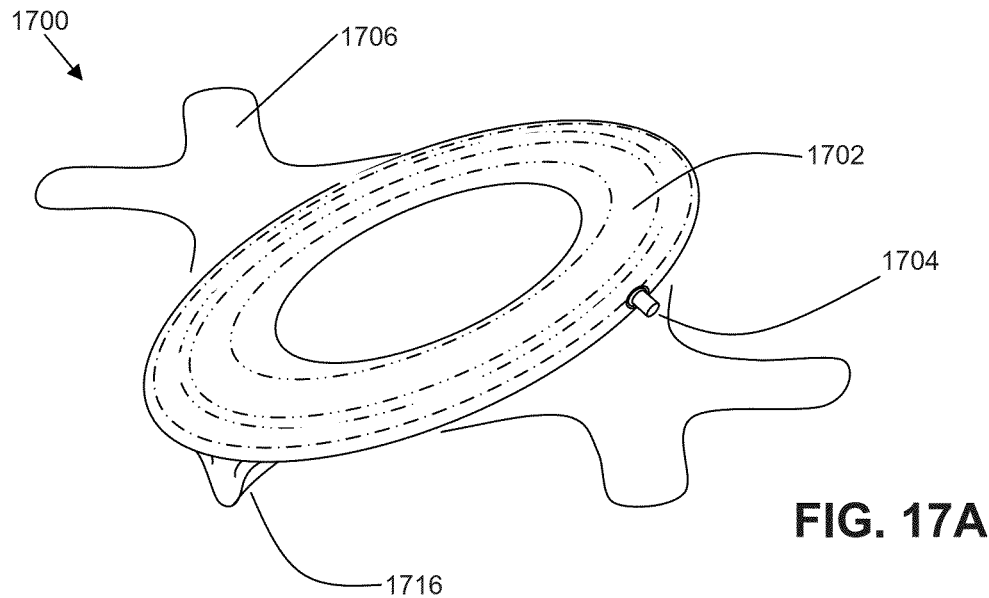
FIG. 17A depicts another variation of a dressing system with a cushion and handles.
Figure 17B:
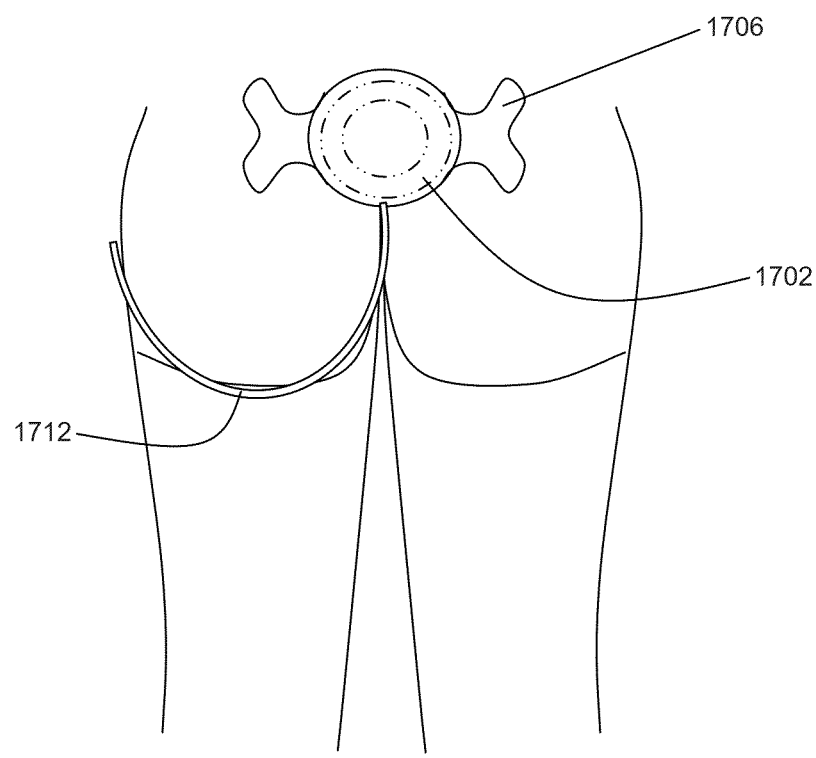
FIG. 17B depicts the dressing system of FIG. 17A used on a sacral region of a patient.
Figure 17C:
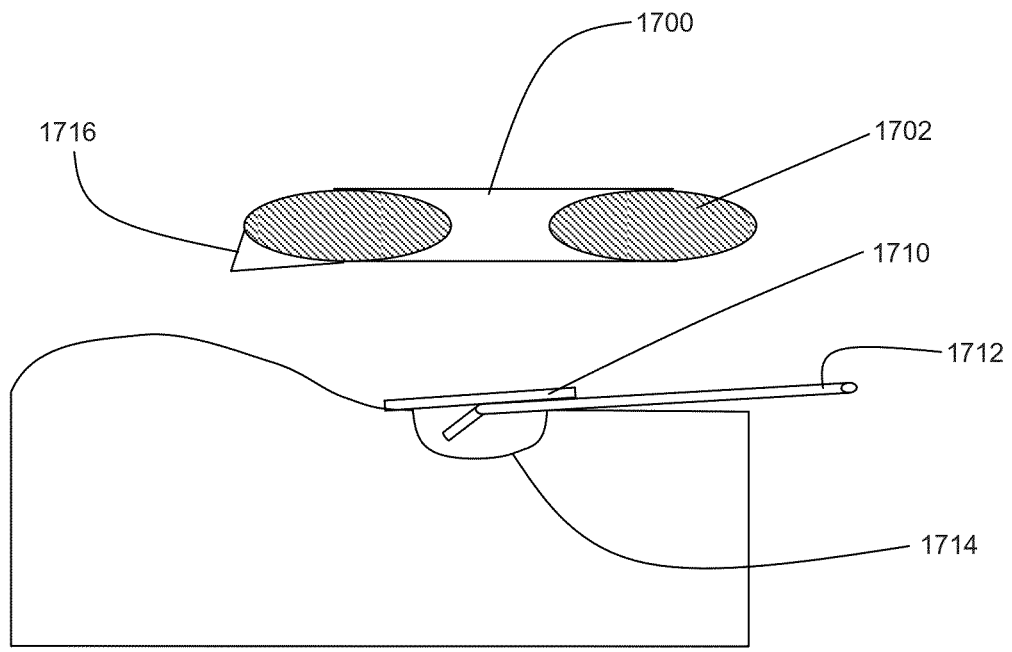
FIGS. 17C and 17D are schematic cross-sectional views of the use of the dressing system of FIG. 17A.
Figure 17D:
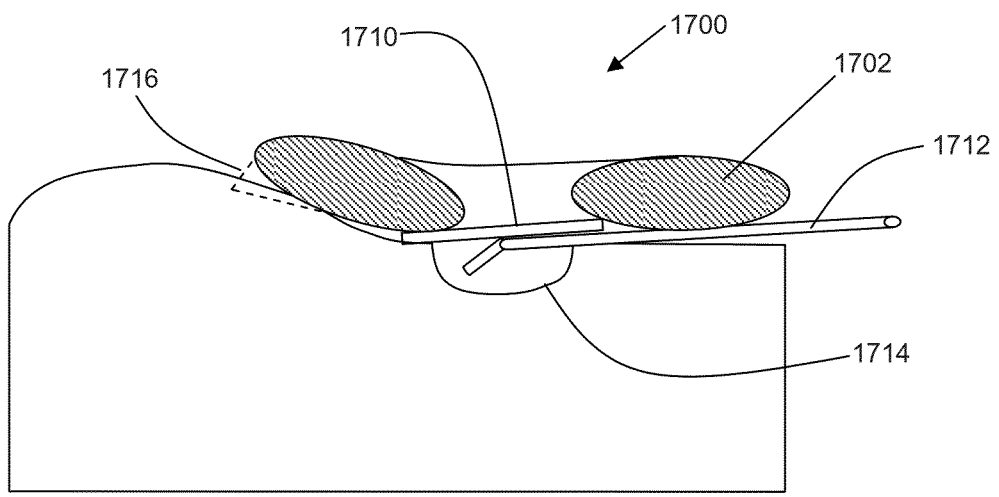

Supportive devices may also have round geometries, as shown in FIGS. 16A and 16B. Supportive device (1600) may have an elliptical shape with an indentation along the perimeter of the ellipse. The supportive device (1600) may have a raised structure (1602) that may be shaped to match the overall shape of the supportive device. The raised structure (1602) may be expanded by injecting fluids through a port (1604), where the fluids may be substantially conformable, compliant, and may have shape-memory properties. The supportive device (1600) may have attachment features such as adhesives, notches, snaps, and the like to interface with a dressing (1610). FIG. 16B illustrates one variation of a dressing that may be configured to attach with the supportive structure (1600). A supportive structure may also have an oval or circular geometry, as depicted in FIGS. 17A-17D. Supportive device (1700) may comprise a circular inflatable raised structure (1702), and one or more adhesive tabs (1706). The adhesive tabs (1706) may be shaped according to the contours of the sacral region, and may be arranged opposite each other, or distributed around the raised structure (1702) to securely attach the supportive structure (1700) in the sacral region. The raised structure (1702) may be inflated via a port (1704). FIG. 17B depicts the supportive structure (1700) attached to the sacral region over a dressing for RPWT. As seen there, the tubing (1712) of the dressing extends from the dressing along the intergluteal cleft and curves along the gluteal crease. FIGS. 17C and 17D depict cross-sections of the supportive structure (1700) and the dressing (1710) before and after the supportive structure is applied onto the dressing. FIG. 17C shows the dressing (1710) enclosing a wound bed (1714) with the tubing (1712) extending from the dressing. FIG. 17D shows the supportive structure (1700) applied over the dressing (1710) such that the raised structure (1702) presses the edges of the dressing (1710) against the skin surface. This may help the dressing (1710) maintain a sufficiently airtight bond with the skin in the sacral region for RPWT of the wound bed (1714). The supportive device (1700) may be applied to the dressing (1710) where the raised structure (1710) is initially deflated. The adhesive tabs (1706) may be used to attach the deflated supportive device (1700) to the skin of the sacral region. Then, the raised structure (1702) may be inflated, e.g., with a syringe, so that the raised structure presses the edge of the dressing against the skin. The supportive device may include pressure sensors, volume indicators and the like to help the user to consistently apply the same degree of inflation.

Figure 18A:
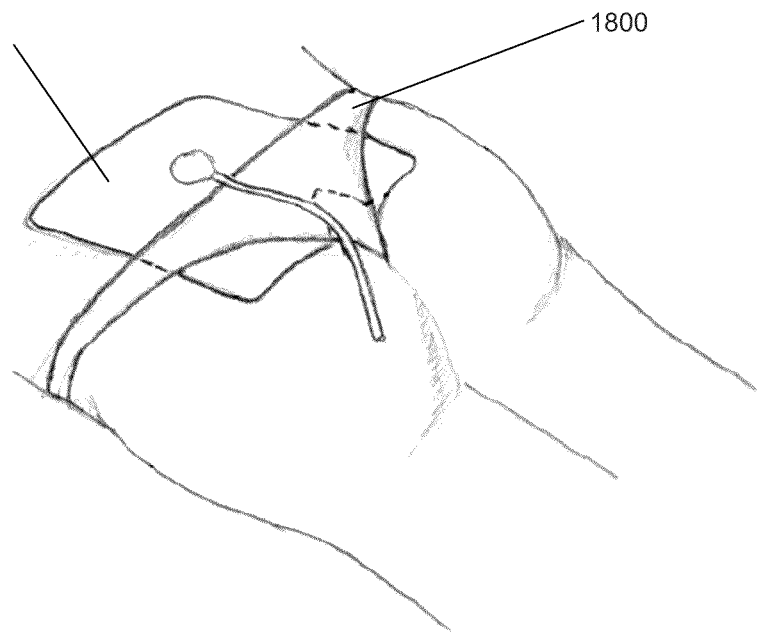
FIGS. 18A-18D depict examples of support garments that may be used with a sacral dressing.
Figure 18B:
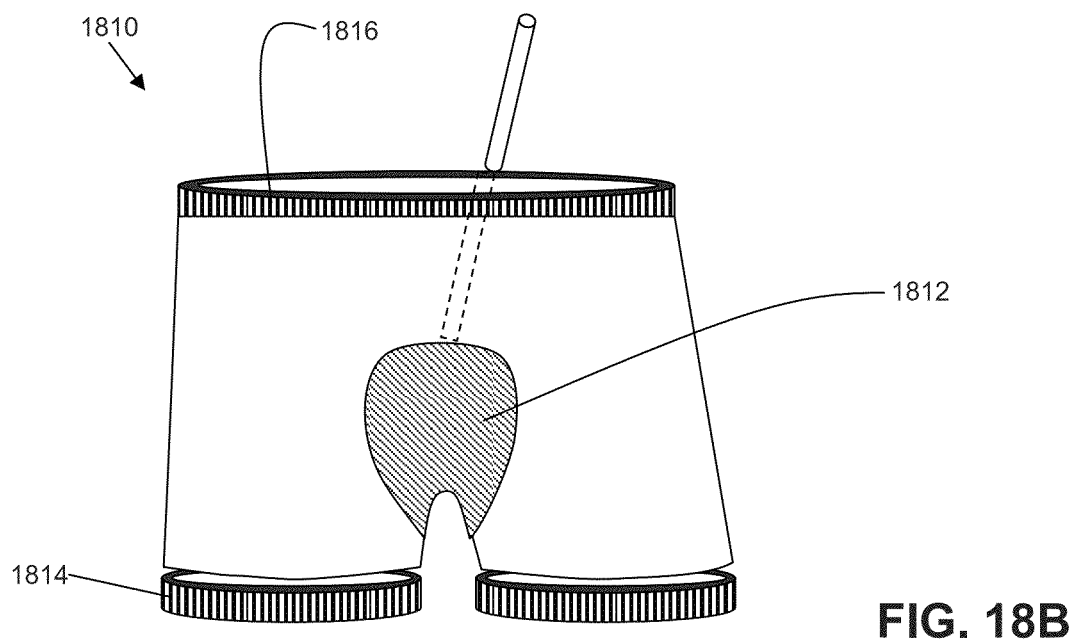
Figure 18C:
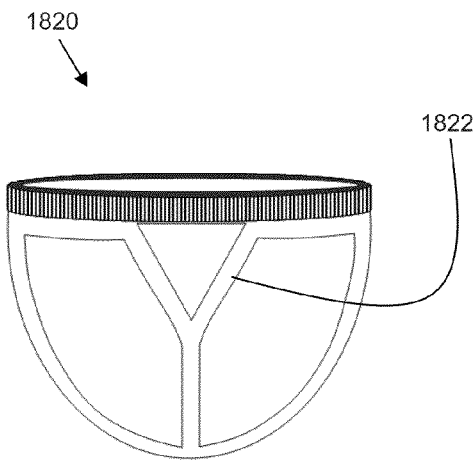
Figure 18D:
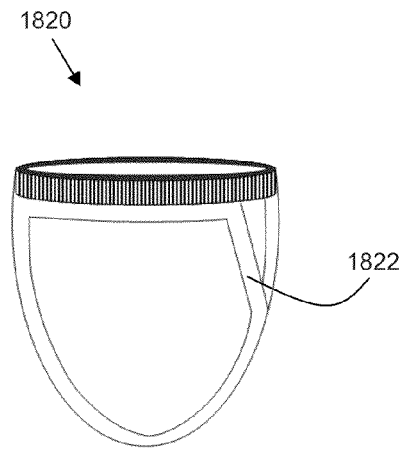

Other devices may also be applied to a dressing for RPWT of the sacral region to help the dressing maintain a substantially airtight seal with the skin surface. FIGS. 18A-18D depict various elastic support garments that may be configured to help keep the edges of the dressing from lifting off the skin surface, and may apply sufficient force to the dressing to help maintain its adhesion during normal patient activity. These supportive garments may provide separate support to the sacral dressing for RPWT. FIG. 18A depicts a supportive undergarment (1800) that may be placed over the dressing (1802). The supportive undergarment (1800) may provide a distributed pressure across regions of the dressing (1802) to help it maintain secure contact with the skin. FIG. 18B depicts one variation of a supportive boxer (1810) that may comprise a super-elastic region (1812) in the proximity of the sacral region where the dressing may be applied to press the dressing against the skin. Optionally, the boxer (1810) may comprise an elastic waistband (1816) and elastic leg bands (1814) that may create a sufficiently airtight seal for reduced pressure to be applied to the entire region enclosed by the boxer (1810). The waistband and leg bands may also comprise an adhesive to provide sealing. FIGS. 18C and 18D depict a supportive strap-based undergarment (1820) that may provide more localized pressure along the perimeter or outer edges of the dressing using straps (1822). The arrangement of straps (1822) may be varied and adjusted according to the geometry and size of the dressing.

Figure 19A:
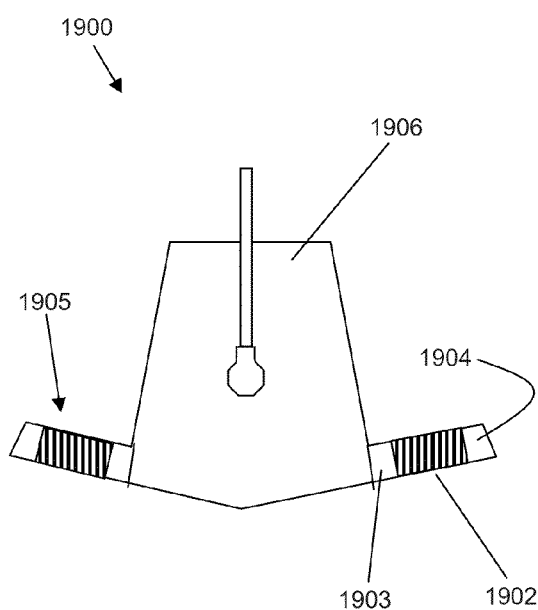
FIGS. 19A and 19B depict a variation of a dressing that may be used to flatten a skin fold and seal a treatment site.
Figure 19B:
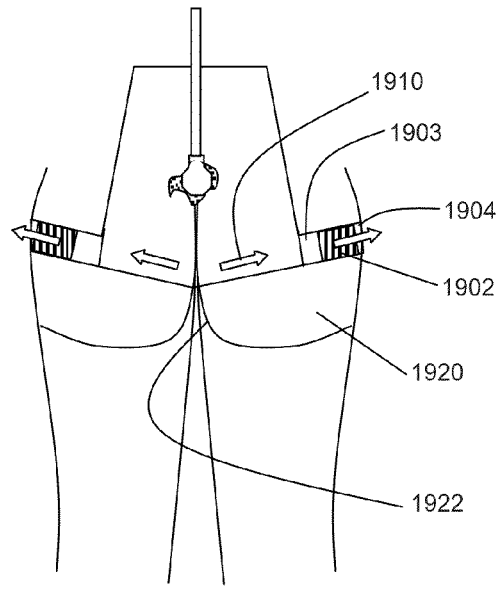

The application of a dressing for RPWT of the sacral region such that a substantially airtight seal is created may be challenging due to the variable contour of the gluteal regions and the intergluteal cleft. In some variations, flattening out the gluteal regions about the intergluteal cleft may facilitate a better seal between the dressing and the skin. For example, stretching out the skin in the sacral region as depicted in FIGS. 19A and 19B may help with applying the dressing to the sacral region. The device (1900) may have a dressing (1906), and at least two tabs (1905) extending from the dressing (1906). The tabs (1905) may extend from each other in opposite directions, and may each comprise a central adhesive region (1907), elastic region (1902), intermediate adhesive region (1903), lateral adhesive region (1904). The tabs facilitate the application lateral forces by the dressing (1906) to flatten the contour between the two gluteal regions (1920), i.e., by increasing the width of the intergluteal cleft (1922), as shown in FIG. 19B. The width of the intergluteal cleft (1922) may be increased because the elastic region (1902) and the adhesive region (1904) act to pull the gluteal regions (1920) in the direction of the arrows (1910). For example, the first adhesive region (1903) may be adhered to each of the gluteal region (1920). Then, the tabs (1905) may be pulled in the direction of arrows (1910), which may increase the width or otherwise spread the intergluteal cleft (1922) and stretch the skin surface of the sacral region. To retain this stretched configuration, the second adhesive regions (1904) may be adhered more laterally, e.g., adhered to the skin toward the lateral portions of the buttocks or hips. The central adhesive region (1907) of the dressing (1906) may then be applied to the stretched sacral region. After the dressing (1906) has been applied, the stretched skin surface may be released by releasing the second adhesive region (1904), and optionally, the first adhesive region (1903). The tabs may also be cut or otherwise separated from the dressing (1906) if desired. The first and/or second adhesive regions may also remain adhered laterally to the patient's skin if it is desirable to retain the stretched skin surface. In general, increasing the width of the intergluteal cleft (1922) may allow better access to the skin within and along the cleft, so that the dressing may be pressed against the skin to form a substantially airtight seal. In some variations, the width of the intergluteal cleft may be increased by using retractor instruments with traction or adhesive surfaces that may be inserted within the intergluteal cleft inferior to the desired dressing site, and used to widen or flatten the cleft as the dressing is applied. The instrument is then withdrawn after the dressing has been securely sealed to the skin surface.

Figure 20A:
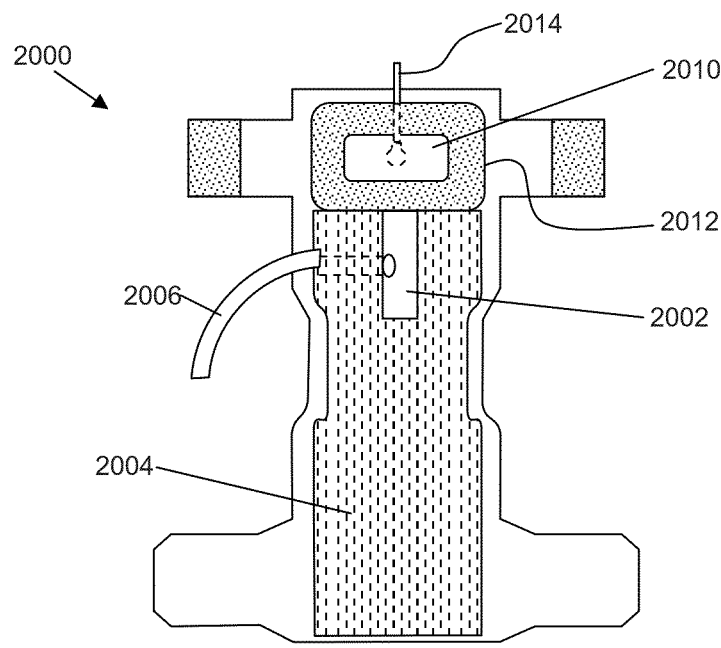
FIG. 20A illustrates a schematic anterior view of a diaper system with an RPWT dressing, and a vacuum tube to remove fecal matter.
Figure 20B:
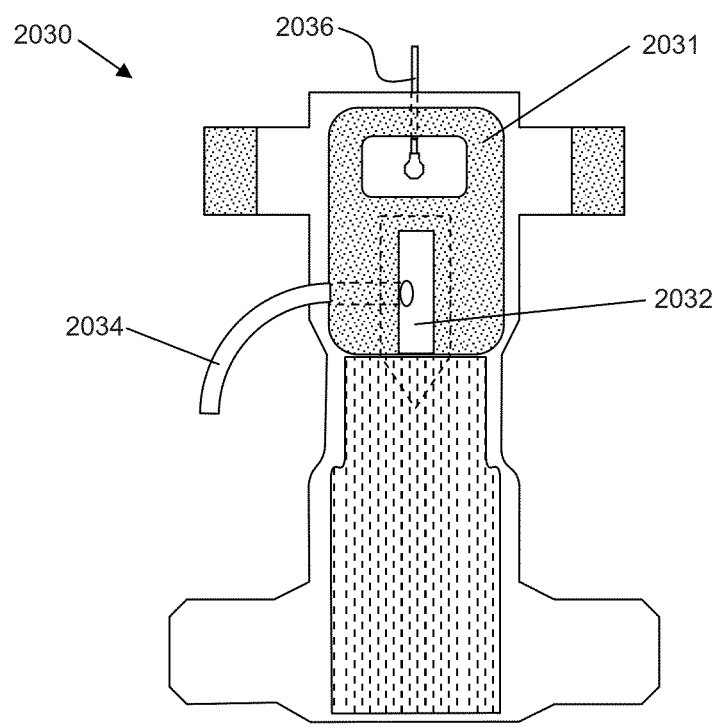
FIGS. 20B and 20C are anterior and cross-sectional views of another variation of a diaper system with an RPWT dressing and a vacuum tube to remove fecal matter.
Figure 20C:
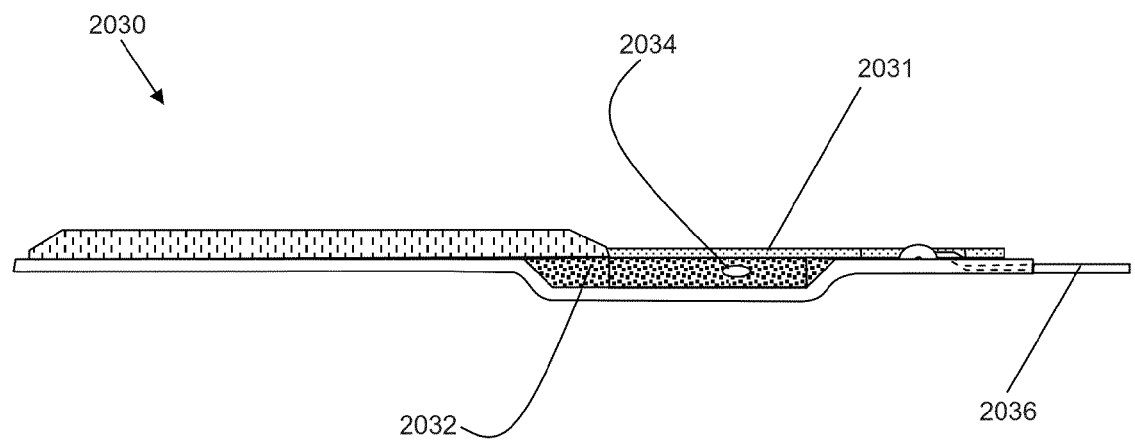

Another device that may be used with a dressing for RPWT of the sacral region is shown in FIGS. 20A and 20B. Device (2000) may comprise a dressing (2012), dressing tubing (2014), a foam or sponge region (2002), and a vacuum tube (2006) connected to the sponge region (2002), and an absorbent material (2004) around the sponge region (2002). The device (2000) may be worn by a patient similar to a diaper, where the sponge region (2002) may be used to capture fecal matter that may be drawn away from the patient via the tube (2006). The absorbent material (2004) may be positioned as shown to absorb and wick away urine and excrement. These features may help to keep the dressing (2012) and dressing adhesive (2010) clean and dry, which may help to maintain and prolong an airtight seal between the dressing (2012) and the skin of the sacral region. As previously described, a dressing tubing (2014) may be provided separately from the vacuum tube (2006) to provide reduced pressure to the area under the dressing (2012). FIG. 20B depicts another variation of a device (2030) where the adhesive portion (2031) of the dressing is larger and surrounds the sponge region (2032). The sponge region (2032) may have a three-dimensional shape, and one or more tapers, such as a triangular prism. This sponge region (2032) may be connected to a vacuum tube (2034) to help remove fecal matter, which may help to maintain a substantially airtight seal between the skin and the dressing, while a dressing tubing (2036) may provide reduced pressure to the area under the dressing. FIG. 20C is a cross-section of the device (2030) shown in FIG. 20B.

Figure 22:
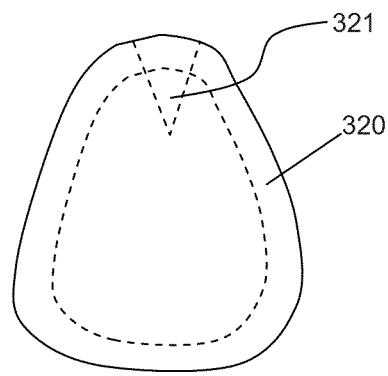
FIGS. 22-24 illustrate a variety of other configurations of a sacral dressing system.
Figure 23:
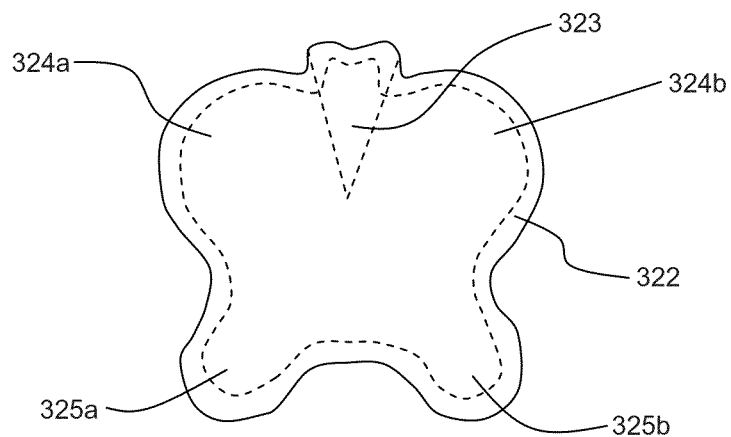
Figure 24:
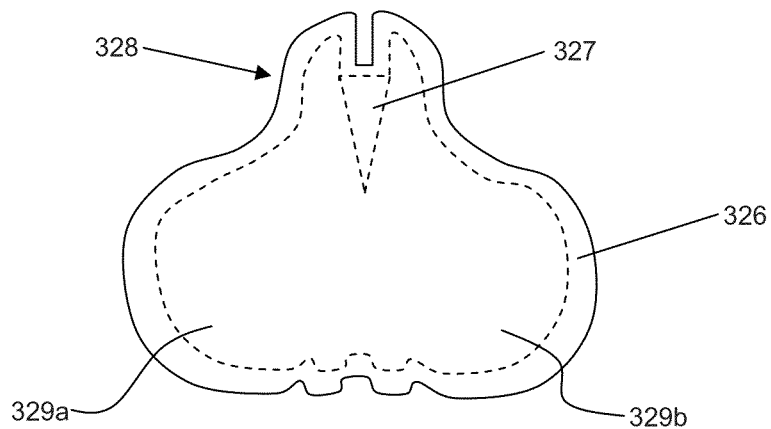

Dressings may have different geometries and shapes to accommodate a variety of anatomical contours. FIG. 22 depicts a dressing that is oval-shaped or ellipse-shaped with a tapered end. The outer edge (320) of the dressing may have adhesive properties to enclose the central region of the dressing for RPWT. The fold-sealing region (321) may be located at the tapered end. Dressings may have a shape that has one, two, three or more lobular regions. For example, FIG. 23 depicts a quad-lobular dressing, with a first lobular region (324a), a second lobular region (324b), a third lobular region (325a), and a fourth lobular region (325b). Dressings may also have lobular regions that are not symmetric across any axis, or lobular regions that are symmetric across one axis but not other axes, e.g., bilaterally symmetric. The outer edge (322) of the dressing may have adhesive properties as previously described. The fold-sealing region (323) may be located along a central axis of the dressing. FIG. 24 depicts a tri-lobular dressing, with a first lobular region (328), a second lobular region (329a), and a third lobular region (329b). The first lobular region (328) may have a notch along the outer edge (326) of the dressing, and the fold-sealing region (327) may be located adjacent to the notch.

Figure 25:
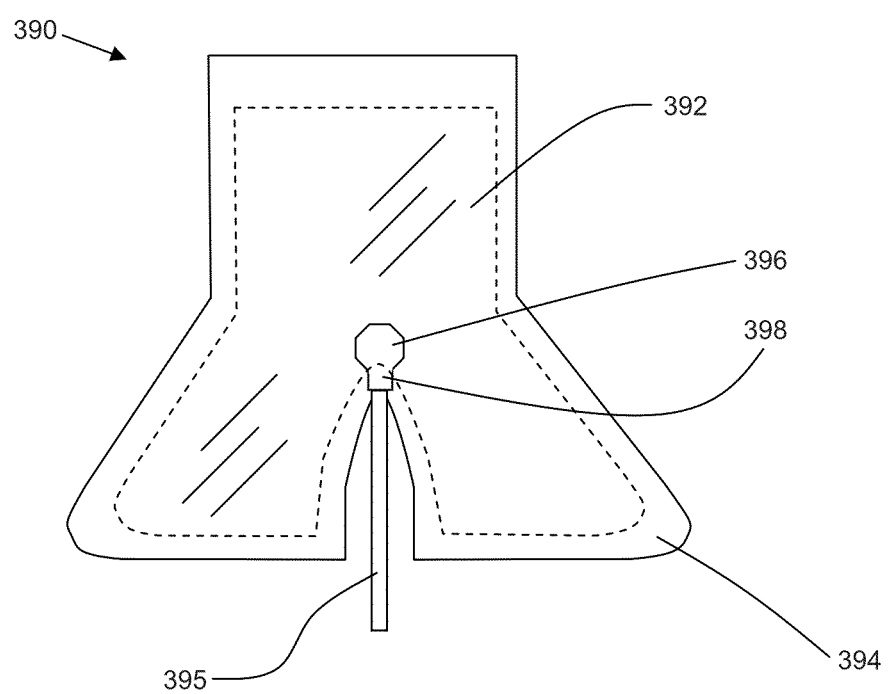
FIG. 25 depicts an example of a tri-flap dressing system.

Another example of a dressing (390) that may be used for RPWT in the sacral region is shown in FIG. 25. As shown there, the dressing (390) may be shaped so that it flares outwardly to help create an airtight seal with the gluteal regions, e.g., the dressing may have a shape similar to a trapezoid where the base is divided by an elongate notch that may align along the length of the intergluteal cleft. The dressing (390) may have a base layer (394) with a transparent region (392) therein so that a sacral wound may be observed in the course of RPWT. The dressing (390) may also comprise an opening (398) that provides fluid access to the wound bed via tubing (395), which may be attached to a dressing port (396).

Methods of applying dressings and devices for RPWT of the sacral region are also described herein. Any of the dressings described above may be configured to work in a system in which a first dressing layer, e.g., a base layer, is placed over the wound first to provide a protective layer to the surrounding healthy skin while a second dressing layer may be placed subsequently. The base layer may comprise a fold-sealing region for creating an airtight seal between the dressing and the skin of the intergluteal cleft. The base layer may also comprise a trimmable wound-contacting region such that the sealing surfaces of the base layer cover the region around the wound, and the trimmable wound-contacting region may be positioned over the wound. This arrangement may promote focal application of RPWT to the wound bed, with reduced impact on the peri-wound tissue. Applying RPWT primarily to the wound bed and not the peri-wound regions may help to protect the surrounding healthy skin from degrading, e.g., by maceration. Once the base layer has been applied to the sacral region, a second dressing layer, e.g., a sealant layer, may be attached on top of the base layer to deliver reduced pressure to the wound bed. The attachment junction of the sealant layer to the base layer may be substantially airtight.

Figure 21:
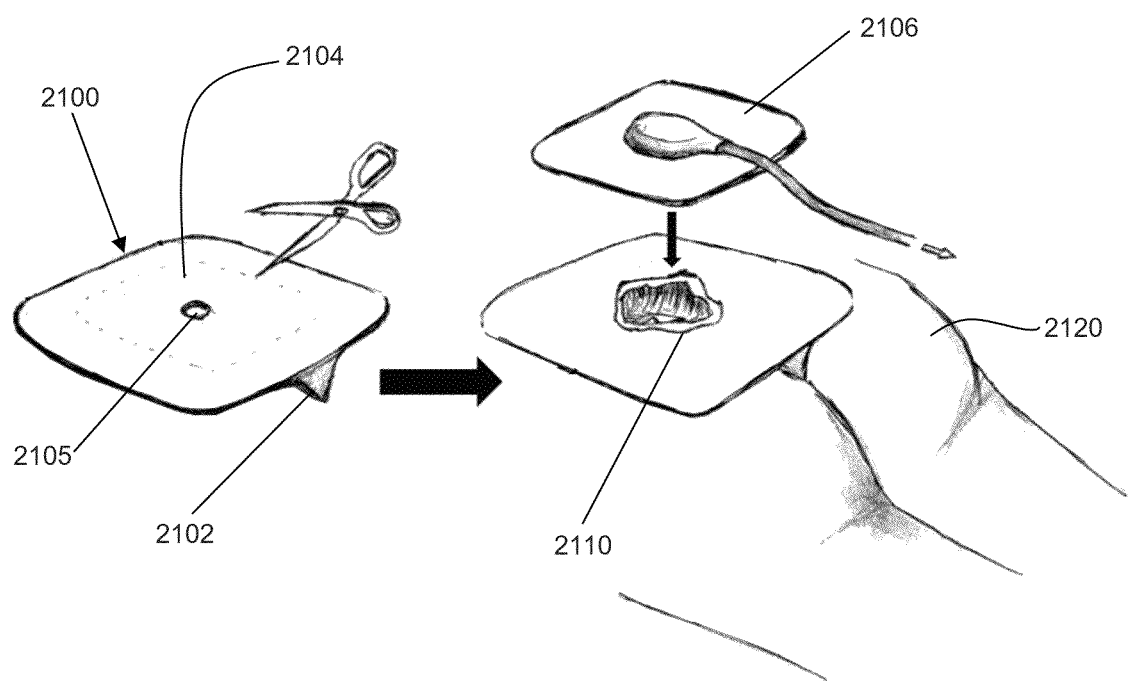
FIG. 21 depicts another variation of a protective layer of a multi-layer dressing system.

One example of a method of applying a dressing to a sacral region for RPWT is shown in FIG. 21. In this variation, a first dressing layer, e.g., base layer (2100), comprising a wound-contacting region (2105) and a fold-sealing region (2102) may be prepared to accommodate the sacral wound (2110). Preparing the base layer (2100) may comprise trimming the wound-contacting region (2105) so that the trimmed aperture approximates the perimeter of the wound (2110), and allows a sufficient wound bed surface to be exposed to reduced pressure. In some variations of a wound-contacting layer, one or more pre-made apertures or perforations may be provided to help facilitate trimming the base layer to a shape that approximates the shape of the wound. For example, a pre-made hole (2105) may be located in a central portion of the wound-contacting region (2104), and may be expanded by cutting away portions of the wound-contacting region to conform to the geometry of the wound. The base layer (2100) may then be placed on the patient and secured to form a substantially airtight seal with the skin surface. The base layer (2100) may be applied such that the fold-sealing region (2102) is first applied to create a sufficiently airtight bond with the skin of the intergluteal cleft. Spreaders and devices as previously described may be used to facilitate sealing with the intergluteal cleft. For example, in some variations of a dressing, a suture may be used to thread the tapered portion of the fold-sealing region (2102) into the intergluteal cleft. Then, the substantially planar portion of the base layer (2100), which may include the wound-contacting region, may be applied over the gluteal regions (2120). Optionally, an additional dressing layer may be applied on top of the base layer (2100), where the additional dressing layer may be foam or gauze. Once it has been confirmed that a sufficiently airtight bond has been created between the base layer (2100) and the skin, a second dressing layer, e.g., a sealant layer (2106), may be applied over the dressing base layer. Once the sealant layer (2106) has been attached to the dressing base layer (2100) and is confirmed to be substantially airtight, RPWT of the wound (2110) may commence.

Methods of removing the dressing (e.g., for cleaning, sterilizing, positional adjustments, etc., or at the completion of the therapy) may vary according to the mechanism(s) by which the dressing is applied to the skin. In some variations, the first dressing layer, may remain attached to the skin, while additional dressing layer above the first layer may be removed. This may reduce the likelihood of damaging peri-wound skin, which may be easily macerated as the dressing is pulled away. Some dressing layers may be attached to each other and/or to the skin surface using differential strength adhesives or other mechanical fixation techniques may allow for easy removal of any of the dressing layers, e.g., the sealant layer (2106) from the base layer (2100). In some variations, the seal between the dressing layers and/or between the dressing and the skin is a temperature-sensitive adhesive. Removal of a dressing layer that is attached using a temperature-sensitive adhesive material may comprise heating the dressing to weaken the bond between the dressing layers, and subsequently removing the top dressing layer once has been loosened. While bonding between the base layer and the sealant layer as described above may be facilitated by pressure-sensitive adhesives, other bonding mechanisms may be used, including bonding by electrostatic forces, self-sealing materials, magnetic interactions, vacuum-gasket seals, or any other mode that enables an airtight juncture to be formed between the two elements. In general, techniques that allow for the removal of a dressing layer without damaging the skin surface as the layer is pulled away may be used.

It is to be understood that this invention is not limited to particular exemplary embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a blade" includes a plurality of such blades and reference to "the energy source" includes reference to one or more sources of energy and equivalents thereof known to those skilled in the art, and so forth.

The publications discussed herein are provided solely for their disclosure. Nothing herein is to be construed as an admission that the present invention is not entitled to antedate such publication by virtue of prior invention. Further, the dates of publication provided, if any, may be different from the actual publication dates which may need to be independently confirmed.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims. For all the embodiments described herein, the steps of the method need not be performed sequentially.

What is claimed as new and desired to be protected by Letters Patent of the United States is:

1. A device to treat a region of a patient having a skin fold, comprising:
   a multi-lobular base layer comprising a first surface, a second surface, an interior region, and an outer perimeter, wherein each lobular region of the base layer comprises a curve that converges at a central axis of the base layer;
   wherein the base layer further comprises a branched conduit system; and
   an adhesive conduit located on the base layer, wherein the adhesive conduit encloses an area of the base layer.

2. The device of claim 1, further comprising an adhesive port in fluid connection with the adhesive conduit.

3. The device of claim 1, further comprising an oblong tubing attached to the base layer, wherein the oblong tubing is embedded in a soft material support or in a gel-filled support.

4. The device of claim 1, wherein the multi-lobular base layer has at least four lobular regions.

5. The device of claim 1, wherein the multi-lobular base layer has at least two lobular regions.

6. The device of claim 1, wherein the multi-lobular base layer is asymmetric across any axis.

7. The device of claim 1, wherein the multi-lobular base layer is symmetric across at least one axis.

8. The device of claim 1, further comprising a fold-sealing region located about the central axis of the base layer.

9. The device of claim 3, wherein the oblong tubing is orthogonal to the central axis of the base layer.

10. The device of claim 3, wherein the oblong tubing is configured to resist occlusion.

11. The device of claim 3, wherein the oblong tubing is directly attached only to the first or second surface of the base layer.

12. The device of claim 3, wherein the oblong tubing is embedded between the first and second surface of the base layer.

13. The device of claim 3, wherein the oblong tubing is directly attached to both the first and second surface of the base layer.

14. A method of treating a wound having a skin fold, comprising:
   providing a device comprising a multi-lobular base layer comprising a first surface, a second surface, an interior region, and an outer perimeter, wherein each lobular region of the base layer comprises a curve that converges at a central axis of the base layer; and an adhesive conduit located on the base layer, wherein the adhesive conduit encloses an area of the base layer;
   placing the device along the skin fold of the wound such that the central axis of the device is aligned with the skin fold; and
   adhering the device to the wound such that a substantially airtight seal is formed between the wound and the device.

15. The method of claim 14, further comprising an adhesive port in fluid connection with the adhesive conduit.

16. The method of claim 14, further comprising:
   providing oblong tubing; and
   placing the oblong tubing in an orthogonal direction to the central axis of the base layer.

17. The method of claim 14, wherein the multi-lobe base layer has at least two lobular regions, further comprising placing a first of the at least two lobular regions on a first side of the skin fold, and a second of the at least two lobular regions on a second side of the skin fold.

18. The method of claim 14, wherein the device further comprises a fold-sealing region located about the central axis of the base layer, further comprising aligning the fold-sealing region with the skin fold.

19. The method of claim 14, further comprising providing oblong tubing, wherein the oblong tubing is directly attached only to the first or second surface of the base layer.

20. The method of claim 14, further comprising providing oblong tubing, wherein the oblong tubing is directly attached to both to the first and second surface of the base layer.

* * * * *